(12) United States Patent
Hernell et al.

(10) Patent No.: US 8,986,682 B2
(45) Date of Patent: *Mar. 24, 2015

(54) METHOD TO INCREASE THE ABSORPTION OF UNSATURATED FATTY ACIDS BY HUMAN INFANTS

(75) Inventors: Olle Hernell, Umeå (SE); Birgitta Olsson, Stenhamra (SE); Patrik Strömberg, Sollentuna (SE); Lennart Svensson, Solna (SE); Kristina Timdahl, Tullinge (SE); Mårten Vågerö, Saltsjö-Boo (SE); Maria Öhman, Piteå (SE)

(73) Assignee: Swedish Orphan Biovitrum AB (publ), Solna (SE)

( * ) Notice: Subject to any disclaimer, the term of this patent is extended or adjusted under 35 U.S.C. 154(b) by 287 days.

This patent is subject to a terminal disclaimer.

(21) Appl. No.: 13/278,682

(22) Filed: Oct. 21, 2011

(65) Prior Publication Data

US 2012/0100127 A1    Apr. 26, 2012

Related U.S. Application Data

(60) Provisional application No. 61/405,297, filed on Oct. 21, 2010.

(51) Int. Cl.
*A61P 27/02* (2006.01)
*C12N 9/20* (2006.01)
*A23C 9/20* (2006.01)
*A23L 1/03* (2006.01)
*A23L 1/29* (2006.01)
*A61K 38/46* (2006.01)
*A23C 9/12* (2006.01)

(52) U.S. Cl.
CPC .............. *A23C 9/206* (2013.01); *A23L 1/034* (2013.01); *A23L 1/296* (2013.01); *A61K 38/465* (2013.01); *A23C 9/1216* (2013.01); *A23V 2002/00* (2013.01)
USPC ......................................... 424/94.6; 435/198

(58) Field of Classification Search
None
See application file for complete search history.

(56) References Cited

U.S. PATENT DOCUMENTS 4,944,944 A * 7/1990 Tang et al. ............... 424/94.6
5,200,183 A * 4/1993 Tang et al. ............... 424/94.6
5,716,817 A    2/1998 Tornell

FOREIGN PATENT DOCUMENTS

| CA | 662815 | 5/1963 |
|---|---|---|
| EP | 0317355 | 5/1989 |
| EP | 0605913 | 7/1994 |
| JP | 2001112468 A | 4/2001 |
| JP | 2009-149550 A | 7/2009 |
| JP | 2010-220627 A | 10/2010 |
| WO | WO-91/15234 | 10/1991 |
| WO | WO 91/18923 | 12/1991 |
| WO | WO 93/25669 | 12/1993 |
| WO | WO 94/20610 | 9/1994 |
| WO | WO 99/54443 | 10/1999 |

OTHER PUBLICATIONS

Forsyth et al Nutr Res Rev 1998, 11 pp. 255-278.*
Lindquist et al. "Lipid digestion and absorption in early life: an update", Curr. Opin. Clin. Nutrition Metabolic Care, May 2010, 13(3):314-320.
Maggio, L. et al. A prospective, randomized, double-blinded crossover study comparing rhBSSL (recombinant human Bile Salt Stimulated Lipase) added to infant formula versus placebo during one week of treatment in preterm infants born before 32 weeks of gestational age: preliminary results, May 6, 2010. http://sobi.test.dropit.se/PageFiles/356/Kiobrina_poster_20100506.pdf.
Swedish Orphan Biovitrum, "Press Release. Swedish Orphan Biovitrum first positive Kiobrina clinical phase II data", May 6, 2010. http://sobi.test.dropit.se.PageFiles/356/Kiobrina_20100506.pdf.
Swedish Orphan International, "Investor presentation. Background information: key products and development pipeline", Nov. 2009. http://www.biovitrum.com/Global/Presentations/interim%20report%20presentations/Background_information_v2.pdf.
U.S. National Institutes of Health: "Efficacy and safety of bile salt stimulated lipase (BSSL) as replacement therapy in infant formula for preterm infants", Aug. 5, 2009. http://clinicaltrials.gov/ct2/show/NCT00659243.
U.S. National Institutes of Health: "Efficacy and safety of bile salt stimulated lipase (BSSL) as replacement therapy in infant formula for preterm infants", Aug. 4, 2009. http://clinicaltrials.gov/ct2/show/NCT00658905.
"Biovitrum Full Year Report 2009", released Feb. 18, 2010.

(Continued)

*Primary Examiner* — Tekchand Saidha
*Assistant Examiner* — Md. Younus Meah
(74) *Attorney, Agent, or Firm* — Morrison & Foerster LLP

(57) ABSTRACT

The present invention relates to a method to increase the absorption by a human infant of at least one unsaturated fatty acid, said method comprising the enteral administration to said infant of recombinant human bile-salt-stimulated lipase (rhBSSL). In another aspect the invention also relates to a method to improve the visual and/or cognitive development of a human infant, said method comprising the enteral administration to said infant of rhBSSL. Such methods have particular utility for preterm human infants, particular those in medical need of increasing their absorption of or availability to such unsaturated fatty acids. In further aspects, the invention relates to kits, packaged-pharmaceutical-products, recombinant human bile-salt-stimulated lipase and pharmaceutical compositions, in each case useful for increasing the absorption by a human infant of at least one unsaturated fatty acid, or for increasing the visual and/or cognitive development of a human infant.

10 Claims, 2 Drawing Sheets

(56) References Cited

OTHER PUBLICATIONS

Swedish Orphan Biovitrum Press Release, "Swedish Orphan Biovitrum has decided to move Kiobrina® into phase III development", released Apr. 21, 2010.
Biovitrum "Interim financial report for the period Jan. 1 to Mar. 31, 2010", released Apr. 27, 2010.
Swedish Orphan Biovitrum poster at "The Power of Programming 2010, an international conference on developmental origins of health and disease" conference, Maggio, L. et al., "A prospective, randomized, double-blind crossover study comparing rhBSSL (recombinant human Bile Salt Stimulated Lipase) added to infant formula versus placebo during one week of treatment in preterm infants born before 32 weeks of gestational age: preliminary results", released on May 6, 2010.
Swedish Orphan Biovitrum press release, "Swedish Orphan Biovitrum presents first positive Kiobrina® clinical phase II data", relating to poster session, released May 6, 2010.
Swedish Orphan Biovitrum "Interim financial report for the period Apr. 1 to Jun. 30, 2010".
Sidisky et al., "Comparison of new 37 component FAME standard on four capillary columns of different polarities," Supelco Reporter (1996) 15(1):1-4.
International Preliminary Report on Patentability for PCT/EP2010/065916, issued Apr. 23, 2013, 8 pages.
International Preliminary Report on Patentability for PCT/EP2010/065915, issued Apr. 23, 2013, 6 pages.
Abouakil et al., "Human milk bile-salt stimulated lipase: further investigations on the amino-acids residues involved in the catalytic site," Biochim Biophys Acta (1989) 1002:225-230.
Alemi et al., "Fat digestion in very low-birth-weight infants: effect of addition of human milk to low-birth-weight formula," Pediatrics (1981) 68:484-489.
Andersson et al., "Pasteurization of mother's own milk reduces fat absorption and growth in preterm infants," Acta Paediatr (2007) 96:445-1449.
Baba et al., "Structure of human milk bile salt activated lipase," Biochem (1991) 30:500-510.
Bernback et al., "The complete digestion of human milk triacylglycerol in vitro requires gastric lipase, pancreatic colipase-dependent lipase, and bile salt-stimulated lipase," J Clin Invest (1990) 85(4):1221-1226.
Beyerlein et al., "Infant formula supplementation with long-chain polyunsaturated fatty acids has no effect on Bayley developmental scores at 18 months of age—IPD meta-analysis of 4 large clinical trials," J Pediatr Gastro Nutr (2010) 50(1):79-84.
Birch et al., "A randomized controlled trial of early dietary supply of long-chain polyunsaturated fatty acids and mental development in term infants," Dev Med Child Neurol (2000) 42(3):174-181.
Bjorksten et al., "Collecting and banking human milk: to heat or not to heat?," Br Med J (1980) 281(6243):765-769.
Blackberg and Hernell, "The bile-salt-stimulated lipase in human milk. Purification and characterization," Eur J Biochem (1981) 116:221-225.
Blackberg et al., "The bile salt-stimulated lipase in human milk is an evolutionary newcomer derived from a non-milk protein," FEBS Lett (1980) 112(1):51-54.
Blackberg et al, "Recombinant human-milk bile-salt-stimulated lipase. Functional properties are retained in the absence of glycosylation and the unique proline-rich repeats," Eur J Biochem (1995) 228:817-821.
Blackberg et al., "Bile-salt-stimulated lipase in human milk: evidence for its synthesis in the lactating mammary gland," FEBS Lett (1987) 217:37-41.
Boehm et al., "Docosahexaenoic and arachidonic acid content of serum and red blood cell membrane phospholipids of preterm infants fed breast milk, standard formula or formula supplemented with n-3 and n-6 long-chain polyunsaturated fatty acids," Eur J Pediatr (1996) 155(5):410-416.

Byard et al., "Sudden infant death syndrome: effect of breast and formula feeding on frontal cortex and brainstem lipid composition," J Paediatr Child Health (1995) 31(1):14-16.
Carey and Hernell, "Digestion and absorption of fat," Semin Gastrointest Dis (1992) 3(4):189-208.
Carlson et al., "Visual acuity and fatty acid status of term infants fed human milk and formulas with and without docosahexaenoate and arachidonate from egg yolk lecithin," Pediatr Res (1996) 39(5):882-888.
Carnielli et al., "Intestinal absorption of long-chain polyunsaturated fatty acids in preterm infants fed breast milk or formula," Am J Clin Nutr (1998) 67(1):97-103.
Chappell et al., "Fatty acid balance studies in premature infants fed human milk or formula: effect of calcium supplementation," J Pediatr (1986) 108(3):439-447.
Chen et al., "Digestion of triacylglycerols containing long-chain polyenoic fatty acids in vitro by colipase-dependent pancreatic lipase and human milk bile salt-stimulated lipase," Biochem Biophys Acta (1994) 1210:239-243.
Cooke, "Are there critical periods for brain growth in children born preterm?," Arch Dis Child Fetal Neonatal Ed (2006) 91(1):F17-F20 (published online Oct. 13, 2005).
Foulder-Hughes and Cooke, "Motor, cognitive, and behavioural disorders in children born very preterm," Dev Med Child Neurol (2003) 45(2):97-103.
Fredrikzon et al., "Bile salt-stimulated lipase in human milk: evidence of activity in vivo and of a role in the digestion of milk retinol esters," Pediatr Res (1978) 12(11):1048-1052.
Freed et al., "Diurnal and within-feed variations in lipase activity and triglyceride content of human milk," J Pediatr Gastroenterol Nutr (1986) 5(6):938-942.
Freed et al., "Bile salt-stimulated lipase in non-primate milk: longitudinal variation and lipase characteristics in cat and dog milk," Biochim Biophys Acta (1986) 878:209-215.
Freudenberg, "A lipase in the milk of the gorilla," Experientia (1966) 22(5):317.
Hall and Muller, "Studies on the bile salt stimulated lipolytic activity of human milk using whole milk as source of both substrate and enzyme. I. Nutritional implications," Pediatr Res (1982) 16(3):251-255.
Hamosh, "Lingual lipase and fat digestion in the neonatal period," J Ped Gastro Nutr (1983) 2(Suppl 1):S236-S241.
Hamosh at "Symposium: Bioactive Components in Milk and Development of the Neonate: Does Their Absence Make a Difference?," Reported in J Nutr (1997) 127:971S-974S.
Hansson et al., "Recombinant human milk bile salt-stimulated lipase. Catalytic activity is retained in the absence of glycosylation and the unique proline-rich repeats," J Biol Chem (1993) 268(35):26692-26698.
Hernell et al., "Breast milk composition in Ethiopian and Swedish mothers. IV. Milk lipases," Am J Clin Nutr (1977) 30:508-511.
Hernell et al., "Does the bile salt-stimulated lipase of human milk have a role in the use of the milk long-chain polyunsaturated fatty acids?," J Pediat Gastro Nutr (1993)16:426-431.
Hernell, "Human milk lipases. III. Physiological implications of the bile salt-stimulated lipase," Eur J Clin Invest (1975) 5(3):267-272.
Hernell, "Assessing fat absorption," J Pediatr (1999) 135(4):407-409.
Howles et al., "Carboxyl ester lipase activity in milk prevents fat-derived intestinal injury in neonatal mice," Am J Physiol (1999) 277(3 Pt 1):G653-G661.
Hui et al., "Sequence identity between human pancreatic cholesterol esterase and bile salt-stimulated milk lipase," FEBS Lett (1990) 276(1-2):131-134.
Innis, "Omega-3 Fatty acids and neural development to 2 years of age: do we know enough for dietary recommendations?," J Pediatr Gastroenterol Nutr (2009) 48 Suppl 1:S16-S24.
Jensen et al., "Specificity of human milk bile salt-stimulated lipase," J Pediatr Gastroenterol Nutr (1985) 4(4):580-582.
Jump et al., "Docosahexaenoic acid (DHA) and hepatic gene transcription," Chem Phys Lipids (2008) 153(1):3-13.
Koletzko et al., "Global standard for the composition of infant formula: recommendations of an ESPGHAN coordinated international expert group," J Ped Gastro Nutr (2005) 41(5):584-599.

(56) References Cited

OTHER PUBLICATIONS

Koletzko et al., "The roles of long-chain polyunsaturated fatty acids in pregnancy, lactation and infancy: review of current knowledge and consensus recommendations," J Perinat Med (2008) 36(1):5-14.
Landberg et al., "Glycosylation of bile-salt-stimulated lipase from human milk: comparison of native and recombinant forms," Arch Biochem Biophys (1997) 344(1):94-102.
Larroque et al., "Neurodevelopmental disabilities and special care of 5-year-old children born before 33 weeks of gestation (the EPIPAGE study): a longitudinal cohort study," Lancet (2008) 371(9615):813-820.
Lee et al., "A biochemical and pharmacological comparison of enzyme replacement therapies for the glycolipid storage disorder Fabry disease," Glycobiology (2003) 13(4):305-313.
Li et al., "Bile salt-stimulated lipase and pancreatic lipase-related protein 2 are the dominating lipases in neonatal fat digestion in mice and rats," Pediatr Res (2007) 62(5):537-541.
Lindquist et al., "Ontogeny of pancreatic lipases," J Pediatr Gastroenterol Nutr (2007) 44:e335.
Linthorst et al., "Enzyme therapy for Fabry disease: neutralizing antibodies toward agalsidase alpha and beta," Kidney Int (2004) 66(4):1589-1595.
Lombardo, "Bile salt-dependent lipase: its pathophysiological implications," Biochim Biophys Acta (2001) 1533(1):1-28.
Manson and Weaver, "Fat digestion in the neonate," Arch Dis Child Fetal Neonatal Ed. (1997) 76(3):F206-211.
Marlow et al., "Neurologic and developmental disability at six years of age after extremely preterm birth," N Engl J Med (2005) 352(1):9-19.
Martinez, "Tissue levels of polyunsaturated fatty acids during early human development," J Pediatr (1992) 120(4 Pt 2):S129-138.
McCann and Ames, "Is docosahexaenoic acid, an n-3 long-chain polyunsaturated fatty acid, required for development of normal brain function? An overview of evidence from cognitive and behavioral tests in humans and animals," Am J Clin Nutr (2005) 82(2):281-295.
Miller and Lowe, "Carboxyl ester lipase from either mother's milk or the pancreas is required for efficient dietary triglyceride digestion in suckling mice," J Nutr (2008) 138(5):927-930.
Morgan et al., "Fatty acid balance studies in preterm infants fed formula milk containing long-chain polyunsaturated fatty acids (LCP) II," Acta Paediatr (1998) 87(3):318-324.
Nilsson, "cDNA cloning of human-milk bile-salt-stimulated lipase and evidence for its identity to pancreatic carboxylic ester hydrolase," Eur J Biochem (1990) 192(2):543-550.
Nosarti, "Adolescents who were born very preterm have decreased brain volumes," Brain (2002) 125(Pt 7):1616-1623.
Pasqualini et al., "Molecular cloning of the oncofetal isoform of the human pancreatic bile salt-dependent lipase," J Biol Chem (1998) 273(43):28208-28218.
Reue et al., "cDNA cloning of carboxyl ester lipase from human pancreas reveals a unique proline-rich repeat unit," J Lipid Res (1991) 32(2):267-276.
Sarkadi-Nagy et al., "The influence of prematurity and long chain polyunsaturate supplementation in 4-week adjusted age baboon neonate brain and related tissues," Pediatr Res (2003) 54(2):244-252.
Serhan et al., "Resolvins, docosatrienes, and neuroprotectins, novel omega-3-derived mediators, and their endogenous aspirin-triggered epimers," Lipids (2004) 39(11):1125-1132.
Serhan et al., "Resolving inflammation: dual anti-inflammatory and pro-resolution lipid mediators," Nat Rev Immunol (2008) 8(5):349-361.
Sinclair and Elliot, "Glycoengineering: the effect of glycosylation on the properties of therapeutic proteins," J Pharm Sci (2005) 94:1626-1635.
Strandvik et al., Recombinant human bile salt-stimulated lipase improves lipid uptake and reduces the pancreatic enzyme supplementation in patients with cystic fibrosis, Poster from 18th North American Cystic Fibrosis Conference, St Louis, Missouri-Abstr. 413 (presented on Oct. 14-17, 2004,) Pediatr Pulmonol Suppl (2004) S27:333.
Stromqvist et al., "Differences in the glycosylation of recombinant and native human milk bile salt-stimulated lipase revealed by peptide mapping," J Chromatogr (1995) 718(1):53-58.
Stromqvist et al., "Recombinant human bile salt-stimulated lipase: an example of defective O-glycosylation of a protein produced in milk of transgenic mice," Transgenic Res (1996) 5(6):475-485.
Stromqvist et al., "Naturally occurring variants of human milk bile salt-stimulated lipase," Arch Biochem Biophys (1997) 347(1):30-36.
Torres et al., "Bile salt-stimulated lipase in the milk of Fulani and Kanuri women in Nigeria and native Nepalese women," J Natl Med Assoc (2001) 93(6):201-207.
Trimble et al., "Characterization of N- and O-linked glycosylation of recombinant human bile salt-stimulated lipase secreted by *Pichia pastoris*," Glycobiol (2004) 14(3):265-274.
Uauy and Dangour, "Fat and fatty acid requirements and recommendations for infants of 0-2 years and children of 2-18 years," Ann Nutr Metab (2009) 55(1-3):76-96.
Venter et al., "The sequence of the human genome," Science (2001) 291:1304-1351.
Wainwright, "Do essential fatty acids play a role in brain and behavioral development?," Neurosci Biobehav Rev (1992) 16(2):193-205.
Wang and Johnson, "Purification of human milk bile salt-activated lipase," Anal Biochem (1983) 133(2):457-461.
Wang et al., "Bile-salt-activated lipase: effect on kitten growth rate," Am J Clin Nutr (1989) 49(3):457-463.
Wang et al., "Isolation and characterization of human milk bile salt-activated lipase C-tail fragment," Biochemistry (1995) 34(33):10639-10644.
Weaver et al., "Upper intestinal mucosal proliferation in the newborn guinea pig: effect of composition of milk feeds," Pediatr Res (1987) 22(6):675-678.
Wilcox et al., "Long-term safety and efficacy of enzyme replacement therapy for Fabry disease," Am J Hum Genet (2004) 75:65-74.
Willatts et al., "Effect of long-chain polyunsaturated fatty acids in infant formula on problem solving at 10 months of age," Lancet (1988) 352(9129):688-691.
Williamson et al., "Effect of heat treatment of human milk on absorption of nitrogen, fat, sodium, calcium, and phosphorus by preterm infants," Arch Dis Child (1978) 53(7):555-563.
Swedish Orphan Biovitrum AB (Sobi) Press Release, "Sobi: Kiobrina pivotal phase 3 study did not meet primary endpoint," released Mar. 26, 2014.
Biovitrum press release, "Kiobrina shows positive phase II results in preterm infants", dated Nov. 25, 2009.
Office Action in Japanese Patent Application No. JP-2013-534173, issued Sep. 22, 2014, 10 pages (English translation included).

\* cited by examiner

Figure 1.1
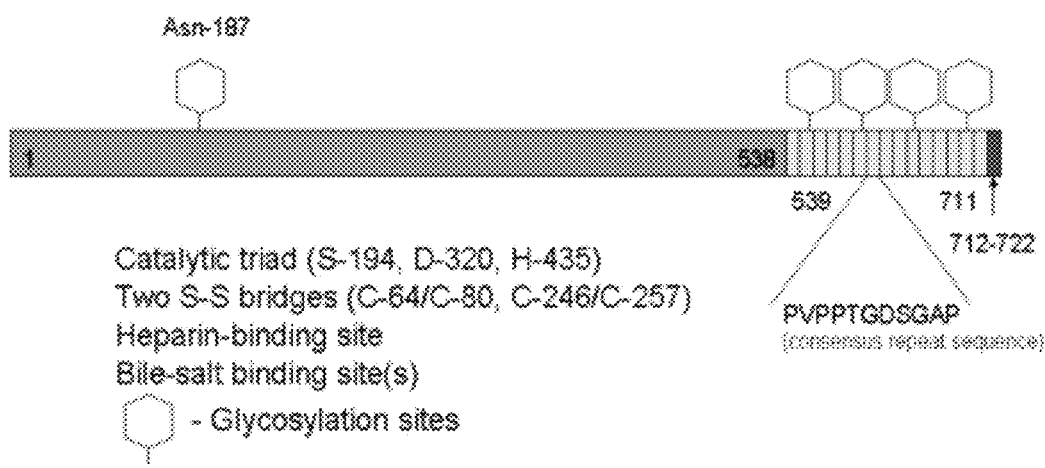
Figure 2.1
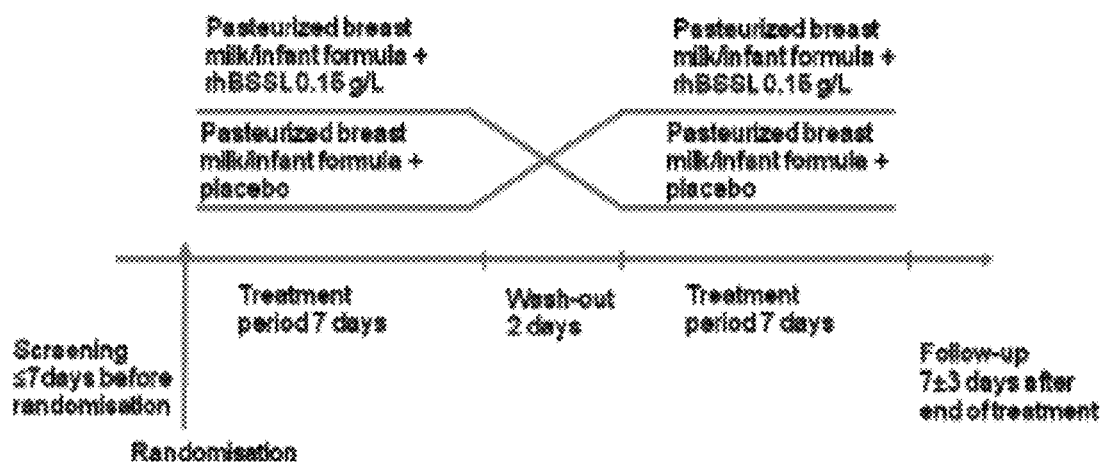

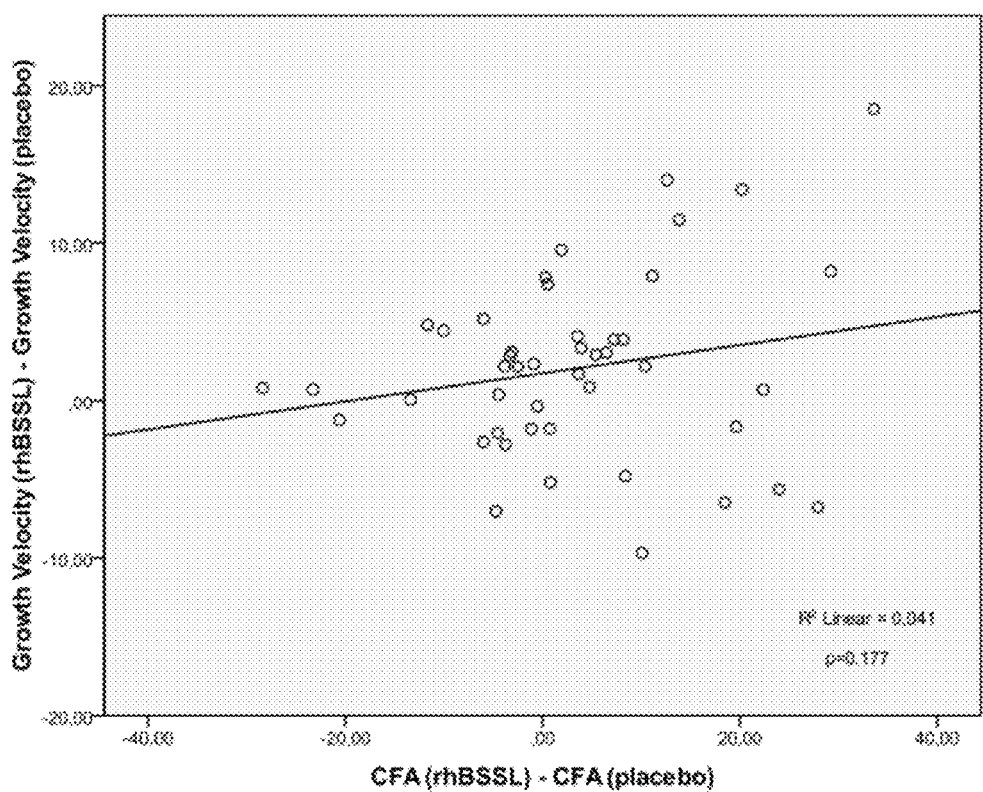
Figure 2.2

US 8,986,682 B2

METHOD TO INCREASE THE ABSORPTION OF UNSATURATED FATTY ACIDS BY HUMAN INFANTS

CROSS-REFERENCE TO RELATED APPLICATIONS

This application claims the benefit of U.S. Provisional Application Ser. No. 61/405,297, filed on Oct. 21, 2010, entitled "Method to Increase the Absorption of Unsaturated Fatty Acids by Human Infants," and is incorporated herein by reference in its entirety.

SEQUENCE LISTING

Incorporated by reference herein in its entirety is the Sequence Listing co-submitted with the instant application, entitled "Sequence_Listing_ST25.txt", created Oct. 17, 2011, size of 10 kilobytes.

TECHNICAL FIELD

The present invention relates to a method to increase the absorption by a human infant of at least one unsaturated fatty acid, said method comprising the enteral administration to said infant of recombinant human bile-salt-stimulated lipase (rhBSSL). In another aspect the invention also relates to a method to improve the visual and/or cognitive development of a human infant, said method comprising the enteral administration to said infant of rhBSSL. Such methods have particular utility for preterm human infants, particular those in medical need of increasing their absorption of or availability to such unsaturated fatty acids. In further aspects, the invention relates to kits, packaged-pharmaceutical-products, recombinant human bile-salt-stimulated lipase and pharmaceutical compositions, in each case useful for increasing the absorption by a human infant of at least one unsaturated fatty acid, or for increasing the visual and/or cognitive development of a human infant.

BACKGROUND

At birth the human fetus switches from a glucose-dominated to a lipid-dominated energy supply since fat, or more specifically triglycerides (TG), that constitutes half of the total energy in human milk and most infant formulae, serves as the dominating energy substrate for newborn infants. Therefore, efficient digestion and absorption of dietary TG is crucial to infant growth and development.

In adults, colipase-dependent pancreatic lipase (PTL) is the main enzyme responsible for the digestion of dietary TG. In the newborn infant, and particularly in the preterm infant, exocrine pancreatic functions are not fully developed (Manson & Weaver, 1997; Arch Dis Child Fetal Neonatal Ed, 76: 206-211). Hence, in the infant, expression of pancreatic lipases is low compared to adult pancreas (Lombardo, 2001; Biochim Biophys Acta, 1533: 1-28; Li et al 1007; Pediatr Res, 62: 537-541), the intraluminal PTL activity during established fat digestion is much lower compared to adults (Fredrikzon et al, 1978; Paediatr Res, 12: 138-140) and fat malabsorption is not uncommon (Carnielli et al, 1998; Am J Clin Nutr 67: 97-103; Chappell et al, 1986; J Pediatr, 108: 439-443). In the breastfed infant, low PTL activity is compensated for by a broad-specificity lipase, bile-salt-stimulated lipase (BSSL) (EC 3.1.1.13), which is secreted both from the lactating mammary gland into the milk and from the exocrine pancreas. In preterm infants, the milk seems to provide the major part of BSSL in duodenal content during a breast milk meal (Fredrikzon et al, 1978).

Whereas fat absorption is an efficient process in healthy human adults with less than 5% of the dietary lipids excreted with the stool (Carey & Hernell, 1992, Semin Gastrointest Dis, 3: 189-208), as much as 20-30% (or more) of the dietary fat may be excreted in preterm infants for no reason other than immaturity. It is of note, however, that the extent of fat malabsorption varies considerably between studies and type of feed, with coefficient of fat absorption (CFA) having been reported as varying from 68% to 91% (see for review, Lindquist & Hernell, 2010; Curr Opin Clin Nutr Met Care, 13: 314-320). Several studies have shown that the CFA from heat-treated (pasteurized) human milk is lower than from raw milk Andersson et al, 2007; Acta Paediatr 96: 1445-1449). Furthermore, CFA from infant formulas is lower than from raw human milk given that the fat composition is similar in formula and milk (Chappell et al, 1986). However, since CFA has been reported to decrease with increasing chain length, from C10:0 to C18:0, of a fatty acid (FA) and increases with increasing number of double bonds, C18:0, C18:1 and C18:2 n-6, of the FA (Andersson et al, 2007, reported in, Lindquist & Hernell, 2010), high concentrations of medium-chain triglycerides (MCTs) or of long-chain triglycerides rich in polyunsaturated FA are used in some formulas to increase overall CFA. Of note is that the reported range of CFA, both from human milk and from formulas are wide. This can partly be explained by the amount and composition of fat given, and partly by large interindividual differences in the capacity to utilize dietary fat in preterm newborns, but it also reflects a considerable difficulty in correctly assessing CFA (Hernell, 1999; J Pediatr, 136: 407-409).

Although lipids in human milk and infant formulas are used mainly as an energy substrate, they are also the carrier of indispensible fat-soluble vitamins and provide essential fatty acids of the n-6 and n-3 series; that is linoleic acid (LA) and alpha-linolenic acid (LNA), respectively. Human milk and most formulas intended for preterm infants also provide conditionally essential fatty acids, that is the long-chain polyunsaturated fatty acids (LCPUFAs) derived from LA and LNA, for example arachidonic acid (AA) and docosahexaenoic acid (DHA), respectively.

Some lipids such as cholesterol, phospholipids and LCPUFAs, as constituents of phospholipids, serve as structural components of cell membranes, and the availability and metabolism of them as membrane components directly affect membrane functions. The retina and brain grey matter are particularly rich in LCPUFA, and neural development and functions may depend on their provision by the diet (Uauy & Dangour, 2009; Ann Nutr Metab 55: 76-96; Innis et al, 2009; J Pediatr Gastroenterol Nutr, 48s1: S16-S24], although this has recently been questioned (Beyerlein et al, 2010; J Pediatr Gastroenterol Nutr, 50: 79-85). Certain LCPUFAs regulate gene expression (Jump et al, 2008: Chem Phys Lipids, 153: 3-13) and are precursors of eicosanoids such as prostaglandins, leukotrienes, thromboxanes, and the more recently discovered docosanoids such as resolvins, docosatrienes and neuroprotectins (Serhan et al, 2004; Lipids, 39: 1125-1132; Serhan et al, 2008; Nat Rev Immunol, 8: 349-361). It is therefore evident that both the quantity of dietary lipids used as energy substrate and the quality of dietary structural lipid supply impact on growth, development and function of the newborn infant.

There have been numerous analyses, studies and reviews published that discuss the link between unsaturated fats, especially LCPUFAs, and visual and/or cognitive development or function, for example as summarized by McCann & Ames in 2005 (Am J Clin Nutr, 82: 281-295). Indeed, on the basis of all available evidence, it has been recommended that infant formulas be supplemented with the LCPUFAs docosahexaenoic acid (DHA) and arachidonic acid (AA), and for pregnant and lactating women to include some food sources of DHA in the diet in view of their assumed increase in LCPUFA demand and the relationship between maternal and fetal/infant DHA status (Koletzko et al, 2008; J Perinat Med, 36:36:5-14).

During the last trimester of fetal life and the first 2 years of childhood, the brain undergoes a period of rapid growth termed the "brain growth spurt". LCPUFAs, particularly DHA and AA, as they are highly concentrated in cell membranes of the retina and brain, accumulate rapidly during the brain growth spurt (Martinez, 1992; J Pediatrics, 120: 129-138). Reduced visual acuity has consistently been observed in primate and rodent offspring subjected to dietary conditions during gestation that result in significant reductions in retinal concentrations of DHA. Human autopsy studies reported significant differences of ~11% to 40% in DHA concentrations in brain gray matter between breastfed and unsupplemented formula-fed infants (for example, Byard et al, 1995; J Pediatric Child Health 31: 14-16). Direct autopsy evidence that compares brain DHA concentrations in human infants fed unsupplemented and LCPUFA-supplemented formulas is not available. However, an autopsy study in nonhuman primates reported ~30% lower concentrations of DHA in the visual cortex of preterm infants fed unsupplemented formula than in those fed LCPUFA supplemented formula (Sarkadi-Nagy et al, 2003; Pediatric Res 54: 244-252). In humans, significant differences in plasma concentrations of DHA and AA between unsupplemented and supplemented formula comparison groups are well documented (for example, Boehm et al, 1996; Eur J Pediatr 155: 410-416).

Many experimental studies that investigated the relationship between mental performance and LCPUFAs have been conducted using rodents. Many early studies suggested an association between a diet severely restricted in n-3 fatty acids during development and poorer performance of offspring in tests designed to measure cognitive or behavioral ability (for example, reviewed in Wainright, 1992; Neurosci Behav Res 16: 193-205). Furthermore, McCann & Ames reviewed eight studies that supplemented n-3-restricted animals with DHA, DHA+AA, DHA-rich oils, or DHA and additional n-6 fatty acids and compared the animals' performance with that of n-3-restricted controls. All of these studies reported that performance was significantly enhanced in the supplemented groups.

McCann & Ames also considered five systematic reviews published since 1999 that critically evaluated partially overlapping subsets of breastfeeding studies spanning over 20 years. Most of the studies included in these reviews compared the performance of children who were breastfed or formula-fed. Before adjustment for covariables, most of these studies reported higher scores on performance tests for children who were breastfed.

Information on the question of causality provided by observational breastfeeding studies, although relevant, is limited. Randomized controlled trials offer much greater opportunity than do observational studies for the control of experimental variables, including the quantity and composition of LCPUFA supplements. In addition, this design affords the opportunity to avoid many of the potential confounding factors that complicate the interpretation of observational breastfeeding studies. In a randomized clinical trial, Willatts and coworkers (1998; The Lancet, 352: 688-691) observed that infants who received LCPUFA-supplemented formula until age 4 months had significantly more intentional solutions when tested at age 10 months than those who received unsupplemented formula. Based on these results, the authors suggested that infants may benefit from LCPUFA supplementation and that the effects persist beyond the period of supplementation. Furthermore, since higher-problem-solving scores in infancy are related to higher IQ scores, they speculated that supplementation may be important for the development of childhood intelligence. In another randomized clinical trial (Birch et al, 2000; Devel Med Child Neurol, 42: 174-181), supplementation of infant formula with DHA+ AA was associated with a mean increase of 7 points on the Mental Development Index (MDI) of the Bayley Scales of Infant Development, 2nd edition test (BSID-II). Both the cognitive and motor subscales of the MDI showed a significant developmental age advantage for DHA- and DHA+AA-supplemented groups over the control group. While a similar trend was found for the language subscale, it did not reach statistical significance. Significant correlations between plasma and red blood cell-DHA at 4 months of age but not at 12 months of age and MDI at 18 months of age suggest that early dietary supply of DHA was a major dietary determinant of improved performance on the MDI. Recently however, a meta-analysis of 4 large clinical trials showed no effect on infant development, as assessed by the Bayley test at 18 months, of formulae supplemented with DHA as compared to unsupplemented formulae (Bayerlein et al, 2010).

A normal human pregnancy lasts for about 40 weeks (38-42 weeks), and the WHO defines prematurity as a baby born before 37 full-weeks from the first day of the last menstrual period. Premature babies are susceptible to a number of health problems and many require specialized care in Newborn Intensive Care Units (NICUs). Of particular significance however, has been the suggestion that normal uterine growth may be very important in terms of early growth of the brain, and premature birth may lead to poor IQ and developmental skills (Cook, 2006; Arch Dis Child Fetal Neonatal Ed, 91: 17-20). Individuals who were born before 33 weeks gestation continue to show noticeable decrements in brain volumes and striking increases in lateral ventricular volume into adolescence (Nosarti et al, 2002; Brain, 125: 1616-1623). Whether such neurological changes are causative remains disputed. However, during follow-up in school life, it has been seen that cognitive and neuromotor impairments at 5 years of age increase with decreasing gestational age. Many of these children need a high level of specialised care (Larroque et al, 2008; Lancet, 8; 371: 813-820). In particular, about half of infants born at 24-28 weeks of gestation have such a disability at 5 years, and in the infants born later (29-32 weeks' gestation), about a third have such a disability at 5 years (Marlow et al, 2005; N Engl J Med, 352: 9-19). Furthermore, other studies have seen association between gestational birth age and behavioral and psychomotor problems. For example, a study from Liverpool (UK) has looked at children of age 7 and 8 who were born before 32 weeks and who were well enough to attend mainstream school, compared with full-term children of similar postpartum age in their class at school (Foulder-Hughes & Cooke, 2003; Dev Med Child Neurol, 45: 97-103). This study suggested that: (i) the preterm children had a higher incidence of motor impairment and this affected how well they did at school even when their intelligence was normal; (ii) over 30% had developmental coordination disorder (DCD) compared with 6% of classmates; (iii) the preterm children were significantly more likely be overactive, easily distractible, impulsive, disorganized and lacking in persistence. They also tended to overestimate their ability; (iv)

attention deficit hyperactivity disorder (ADHD) was found in 8.9% of the preterm children and only 2% of controls. Of note however, was that the children who had been the most premature were not necessarily those with the lowest scores and, in comparison to historical studies, although major disabilities have been reduced, the levels of those disabilities tested in this study did not seem lower than those found in children born 10 or 20 years earlier, despite improvements in care of the newborn.

As described above, pancreas and liver functions are not fully developed at birth, and in premature infants this is particularly notable. Lindquist and Hernell (1990; Curr Opin Clin Nutr Metab Care, 13: 314-320) have recently reviewed the subject of lipid digestion and absorption in early life. Breast-fed infants digest and absorb fat (and importantly LCPUFAs) more efficiently than formula-fed infants (Bernback et al, 1990; J Clin Invest, 85:1221-1226; Carnielli et al, 1998). In addition to infant formulas of similar fat composition, mother's milk also contains a broad-specificity lipase, bile-salt stimulate lipase (BSSL) (EC 3.1.1.13) that promotes highly efficient fat absorption from human milk.

BSSL is believed to have a broader substrate specificity than most lipases. Not only is the enzyme capable of completely hydrolyzing all three fatty acids of TG, but also fat soluble vitamin esters such as vitamin A as well as cholesteryl esters. Thus, BSSL drives the intraluminal lipolysis toward completion and results in the formation of glycerol and free fatty acids (FFAs), including long-chain polyunsaturated fatty acids (Hernell, 1975; Eur J Clin Invest, 5: 267-272; Bernback et al, 1990; Hernell et al, 1993; J Pediat Gastro Nutr, 16: 426-431; Chen et al, 1994; Biochem Biophys Acta, 1210: 239-243). BSSL shows optimal activity at a pH of 8-8.5 and is more stable in acid environments than pancreatic lipase. BSSL is resistant to degradation by pepsin at physiological concentrations. BSSL accounts for about 1% of the total protein in milk and is present at concentrations from 0.1-0.2 g/L (Blackberg et al, 1987; FEBS Lett, 217: 37-41; Wang & Johnson, 1983; Anal Biochem, 133: 457-461; Stromqvist et al, 1997; Arch Biochem Biophys, 347: 30-36). The levels of BSSL in human milk are similar throughout the day (Freed et al, 1986; J Pediatr Gastroenterol Nutr, 5: 938-942) and BSSL production in human milk is maintained for at least 3 months (Hernell et al, 1977; Am J Clin Nutr, 30: 508-511) although concentrations of BSSL may decline with duration of lactation (Torres et al, 2001; J Natl Med Assoc, 93: 201-207). Triglycerides comprise about 98% or more of all lipids in human milk or formula and thereby account for about 50% of the energy content.

Using fresh human milk as a (realistically) complex source of TGs and BSSL, Hall & Muller (1982; Pediatr Res 16: 251-255) concluded that BSSL showed little specificity for different fatty acids of TG. In contrast, using (an artificial system of) an equimolar mixture of monoacid TGs, Wang & coworkers (1983; J Biol Chem, 259: 9197-9202) suggested that BSSL hydrolyzed the short chain TGs more readily than long-chain, and that C18:2 fatty acids were hydrolyzed faster than C18:1 and C18:0. Jensen & coworkers (1985; J Pediatr Gastroenterol Nutr, 4: 580-582) obtained evidence of biased hydrolysis of an asymmetric TG in favor of hydrolysis of C18:2 fatty acid. Using radiolabeled rat-derived chylomicrons, Hernell and coworkrs (1993; J Pediatr Gastroenterol Nutr, 16: 426-431) concluded that BSSL did not differentiate between the hydrolysis of LA (C18:2 n-6) or AA (C20:4 n-6) or between that of AA and eicosapentaenoic acid (C20:5 n-3). In a similar assay, Chen and coworkers (1994; Biochim et Biochphys Acta, 1210: 239-243) obtained evidence that BSSL hydrolyzed DHA fatty acids (C22:6 n-3), but less efficiently than C18:1 or AA, and speculated that BSSL may have a physiological role in completing duodenal hydrolysis of milk TG containing DHA or AA esters to free fatty acids and glycerol.

The superiority of human milk as a nutritional source for term as well as preterm infants has been manifested in many studies and expert group recommendations. Accordingly, the recommended feeding method world-wide is breastfeeding. Neither is however, breastfeeding nor feeding the mother's own breast milk always possible or recommended for medical reasons—and breastfeeding may not be practiced for a number of other reasons—in each case as discussed elsewhere herein. In cases where the infant is not breast-fed, infant formula or banked and non-banked pasteurized and/or frozen breast milk is often used. All are, however, in some respects nutritionally suboptimal for newborn infants.

Due to risks of viral infection (human immunodeficiency virus [HIV], cytomegalovirus [CMV], hepatitis) and to a lesser degree transmission of pathogenic bacteria, donor milk used in so-called milk banks is generally pasteurized before it is used. However, BSSL is inactivated during pasteurization of human milk (Björksten et al, 1980; Br Med J, 201: 267-272); nor is it present in any of the many different formulas that exist for the nutrition of pre- or full-term neonates. It has been shown that fat absorption, weight gain and linear growth is higher in infants fed fresh compared to pasteurized breast milk (Andersson et al. 2007; Williams et al, 1978; Arch Dis Child 43: 555-563). This is one reason why it has been advocated that newborn infants, particularly preterm infants, that cannot be fed their own mothers milk should be fed non-pasteurized milk from other mothers (Bjorksten et al, 1980).

Hamosh (1983; J Ped Gastro Nutr, 2: 248-251) reported that BSSL enzyme activity is present in fresh breast milk of women who delivered at 26 to 30 weeks. This report further described that milk specimens stored at −20 or −10° C. showed a slow loss in BSSL activity, but a more dramatic loss of bile-salt dependency on activity after only three weeks storage at −10° C. which may contribute to hydrolysis of milk lipids even during storage of breast milk at −20° C.

Milk bile-salt-stimulated lipase has been found only in the milk of certain species, namely humans, gorillas, cats and dogs (Freed, et al, 1986; Biochim Biophys Acta, 878: 209-215). Milk bile-salt-stimulated lipase is not produced by cows, horses, rats, rabbits, goats, pigs or Rhesus monkeys (Blackberg et al, 1980; Freudenberg, 1966; Experientia, 22: 317).

Native human milk BSSL (hBSSL-MAM) has been purified to homogeneity, as reported by Blackberg and Bernell (1981; Eur J Biochem, 116: 221-225) and Wang & Johnson (1983), and the cDNA sequence of human BSSL was identified by Nilsson (1990; Eur J Biochem, 192: 543-550) and disclosed in WO 91/15234 and WO 91/18923. Characterization and sequence studies from several laboratories concluded that the proteins hBSSL-MAM and the pancreas carboxylic ester hydrolase (CEH) (also known as pancreatic BSSL) are both products of the same gene (for example, Baba et al, 1991; Biochem, 30: 500-510 Hui et al, 1990; FEBS Lett, 276: 131-134; Reue et al, 1991; J Lipid Res, 32: 267-276).

Following the isolation of the cDNA sequence, recombinant human BSSL (rhBSSL), as well as variants thereof, has been produced including in transgenic sheep (rhBSSL-OVI); such as described in U.S. Pat. No. 5,716,817, WO 94/20610 and WO 99/54443. Production of proteins for therapeutic use using transgenic animals has been met with significant safety, scientific, regulatory and ethical resistance. Indeed, to date there is no approved therapeutic product on the US or EU market that has been produced from transgenic sheep, and only two medical products produced from other transgenic animals have so far been approved: ATRYN (recombinant antithrombin) produced from transgenic goats, and RUCONEST (recombinant component 1 esterase inhibitor) produced from transgenic rabbits. Proteins produced in such a manner (to be expressed in mammary tissue and excreted in milk) can be contaminated with components naturally found in the milk of these animals, such as whey or non-human milk or whey proteins, which may cause safety issues if such proteins are used for human use in certain individuals, such as those intolerant or allergic to milk-based components or products.

It has long been promoted that fresh human breast milk is the most suitable feed for human infants. This is based on studies such as the early work by Williams et al (1978) who showed that heat-treatment of human milk reduced fat absorption by approximately one-third (compared to raw human milk) in an experimental study of seven VLBW preterm infants (less than 1.3 Kg) aged between 3 and 6 weeks, fed for three consecutive weeks with raw, pasteurized and boiled human milk, each for one week. This study made the suggestion that the improvement in fat absorption may be related to the preservation of milk lipases in the raw, compared to the heat-treated, human milk. Of note is that this study described that all infants gained weight most rapidly during the week in which they were fed raw milk; with the mean weight gain (reported in g gained per week per 100 mL milk consumed) during this period approximately one third greater than the similar periods during which pasteurized or boiled milk was administered. In a larger (but shorter) study reported by Alemi (1980; Pediatrics. 68: 484-489), fat excretion was studied in 15 VLBW infants, born with a birth-weight of between 660 and 1,695 g and a gestational age of 26 to 33 weeks, and the study started at 7 to 44 days after birth. Fat excretion was lower in those infants fed a mixture of human milk and formula for 72 hours compared to the infants fed formula only. More recently, Andersson & coworkers (2007) reported in a randomized study that pasteurization of mother's own milk reduced fat absorption and growth in preterm infants, and proposed that these effects were due to inactivation of milk-based BSSL by pasteurization. Of note is that the reported range of coefficient of fat absorption (CFA) from a number of studies, including those above, are wide; both from human milk and from formulas. This can partly be explained by the amount and composition of fat given, and partly by large interindividual differences in the capacity to utilize dietary fat in preterm newborns, but it also reflects a considerable difficulty in correctly assessing CFA (Hernell, 1999; J Pediatr, 136: 407-409).

One animal model study has attempted to investigate the effects on infant growth by the addition on exogenous BSSL to neonatal food (Wang et al, 1989; Am J Clin Nutr, 49: 457-463. This study involved the addition of purified human BSSL (0.1 mg/mL) to kitten-formula (mixed three to one with cow milk) and then fed to to six bottle-fed kittens for 5 days. This study reported that kittens fed with kitten-formula supplemented with hBSSL had a growth rate of twice that of those fed with formula alone. Of note is that the formula was supplemented with cow milk, the kittens were not preterm or of low birth weight, they were breast fed for the first 48 hours of their life and the study was conducted with purified native hBSSL. The authors suggested that the kitten could be utilized as an animal model in the investigation of the functional role of BSSL, and on the basis of this study related patent applications were filed (including, U.S. Pat. No. 4,944,944, EP 0317355 and EP 0605913) that disclose (amongst other aspects): a method for fortifying a fat-containing infant formula which is poor in bile-salt-activated lipase comprising adding to the formula an effective amount of an isolated bile-salt-activated lipase selected from the group consisting of milk bile-salt-activated lipase [BSSL] and bile-salt-activated pancreatic carboxylesterase [now known to also be BSSL] to increase fat absorption from the formula and growth of the infant; and a method for feeding an infant a dietary base from a first source comprising fats consisting of administering an isolated bile-salt-activated lipase selected from the group consisting of milk bile-salt-activated lipase [BSSL] and bile-salt-activated pancreatic carboxylesterase [also BSSL] to the infant in an amount sufficient to improve the infant's digestion and absorption of the fats in the base and increase the growth of the infant, wherein the lipase is derived from a second source. No data supporting an improvement in fat absorption were disclosed, not any data obtained from any study that involved human infants. Another study (Lindquist et al, 2007; J Pediatr Gastroenterol Nutr 44: E335) has been reported by Lindquist & Hernell (2010) as artificially feeding purified human BSSL to BSSL-knock-out mice pups nursed by BSSL-knock-out dams to restore normal fat absorption and preventing the formation of intestinal lesions.

Following the cloning of the hBSSL cDNA and the disclosure of various approaches to produce large quantities of recombinant human BSSL (rhBSSL), numerous disclosures have been made, and claims to, various infant formulas comprising rhBSSL (for example, U.S. Pat. No. 5,200,183, WO 91/15234, WO 91/18923, and U.S. Pat. No. 5,716,817) and various methods or uses of such formula or rhBSSL, including as an infant supplement, for the improvement of dietary lipids, treatment of fat malabsorption, certain pancreatic abnormalities and cystic fibrosis (for example, WO 91/18923, WO 94/20610 and WO 99/54443). However, as with the earlier suggestive studies, no supporting data obtained from experiments supplementing human infants with recombinant bile-salt-stimulated lipase are disclosed. Indeed, in 1996 after all these suggestions, associative studies and disclosures, leading workers in the area were still questioning: "Should bioactive components of human milk [such as BSSL] be supplemented to formula-fed infants?"; and further stating that: "There are no data on attempts to supplement digestive enzymes [such as BSSL]" (Hamosh, at *Symposium: Bioactive Components in Milk and Development of the Neonate: Does Their Absence Make a Difference?* Reported 1997, in J Nutr, 12: 971-974). More recently, Andersson and coworkers (2007) have speculated that supplementing pasteurized milk with recombinant human milk BSSL may restore endogenous lipolytic activity of the milk.

The 722 amino-acid native BSSL is heavily glycosylated (30-40% carbohydrate) (Abouakil et al, 1989; Biochem Biophys Acta, 1002: 225-230), with extensive O-glycosylation sites within the C-terminal portion of the molecule that in its most abundant form contains 16 proline-rich repeats of 11 residues with O-linked carbohydrates (Hansson et al, 1993; J Biol Chem, 268: 26692-26698). The role of the extensive O-glycosylation is unproven, but based on its sequence composition the large C-terminal tail is predicted to be very hydrophilic and accessible (Wang et al, 1995; Biochemistry, 34: 10639-10644).

Differences in glycosylation patterns can have dramatic differences in the activity or other properties of many proteins, especially proteins used in medicine. For example, ARANESP (darbepoetin alpha) is a specifically engineered variant of erythropoietin that differs from PROCRIT (epoetin alpha) by 2 amino acids that provides the molecule with 5 N-linked oligosaccharide chains rather than 3, and which significantly alter the pharmacokinetic properties; with darbepoetin showing a threefold increase in serum half-life and increased in vivo activity compared to epoetin (Sinclair and Elliot, 2005; J Pharm Sci 94: 1626-1635).

Different recombinant production systems (such as mammalian cell, yeast, transgenic animal), and even seemingly minor changes in production process from the same expression system, can lead to changes in the glycosylation of the same protein/polypeptide sequence. For example, recombinant human alpha-galactosidase A is used in enzyme replacement therapy for Fabry's disease, and the commercial drug product is produced in two ways, having the same amino acid sequence but each having a different glycosylation pattern: REPLAGAL (agalsidase alfa) and FABRAZYME (agalsidase beta). REPLAGAL is produced in a continuous line of human fibroblasts while FABRAZYME produced in Chinese hamster ovary (CHO) cells, and each product has different glycosylation. In common with other proteins produced from CHO cells, FABRAZYME is a sialyated glycoprotein, and has differences in the degree of sialyation and phosphorylation compared to REPLAGAL (Lee et al, 2003; Glycobiology, 13: 305-313). The qualitative and quantitative differences in the sialylation of glycoproteins produced in CHO cells in comparison with natural human glycoproteins have consequences for both the level of biodistribution and immunogenic potency. In fact, the presence of IgG has been reported in almost all patients treated with agalsidase beta compared to only 55% of patients treated with agalsidase alfa (Linthorst et al, 2004; Kidney Int, 66: 1589-1595). Moreover, in some cases, an allergic type reaction to treatment with agalsidase beta has been recorded, with the presence of IgE in the circulation and/or a positive intradermal reaction (Wilcox et al, 2004; Am J Hum Genet, 75: 65-74).

Indeed, while their peptide maps are very similar, the glycosylation patterns of native BSSL does differ substantially from that of rhBSSL produced in mouse C127 and hamster CHO cell lines, and also in the ability to bind to certain lectins including concanavalin, *Ricinus communis* agglutinin and *Aleuria aurantia* agglutinin suggesting that native BSSL contains considerably more fucose and terminal beta-galactose residues than the recombinant forms (Stromqvist et al, 1995; J Chromatogr, 718: 53-58). Landberg et al (1997; Arch Biochem Biophys 344: 94-102) further characterized these two recombinant forms, and reported that both recombinant forms had a lower molar percent of total monosaccharide (20% and 15% for C127- and CHO-produced rhBSSL, respectively, compared to 23% for native hBSSL), and that while native hBSSL reacted to certain Lewis antigen-detecting antibodies, the C127-rhBSSL did not.

Although the C127- and CHO-produced rhBSSL reported above were generally similar to each other in terms of molecular mass, glycosylation and lectin binding, in contrast, the rhBSSL isolated from the milk of transgenic mice showed a lower apparent molecular mass on size-exclusion chromatography (SEC) and no detectable interactions with a panel of lectins, indicating a significantly lower degree of O-glycosylation of rhBSSL in milk from transgenic mice than found for the other recombinant forms (Stromqvist et al, 1996; Transgen Res 5: 475-485).

Clinical studies in specific indications conducted with one particular form of rhBSSL have been reported; namely early-phase exploratory studies of exocrine pancreatic insufficiency (PI) due to chronic pancreatitis or cystic fibrosis (CF). In 2004, a phase II trial was reported that showed that CF patients (aged 12 to 39 years) with PI had a more rapid and efficient lipid uptake when supplemented with rhBSSL at a single dosing of 0.2 g or 1 g as a complement to 25% of their regular Creon dosing, as compared to Creon alone given at their regular does, or at 25% dosage (Strandvik et al, 2004; 18th North American Cystic Fibrosis Conference, St Louis M I; abstract published in Pediatr Pulmonol, S27: 333), and in 2005 the results of a second phase II trial were reported as rhBBSL showing a greatly improved ability of a group of Swedish patients with CF suffering from PI to digest fat (press release from Biovitrum, reporting Strandvik et al, 2005; 28th European Cystic Fibrosis Society (ECFS) Conference, Crete). In both clinical trials, these clinical results were obtained using rhBSSL-OVI. More recently, it has been announced that a further phase II trial with an oral suspension of rhBSSL (described therein as "bucelipase alpha"), dosed at 170 mg 3 times daily for 5-6 days, to evaluate the effect on the fat absorption in adult patients with CF and PI has been completed, but no efficacy results from this have to date been published (clinicaltrials.gov identifier NCT00743483).

It has been disclosed since at least 2008 that two phase II trials using rhBSSL were planned and ongoing, each to investigate the coefficient of fat absorption, and change in length and body weight, in preterm infants born before 32 weeks gestational age treated with 0.15 g/L rhBSSL or placebo for one week each, added to infant formula (clinicaltrials.gov identifier NCT00658905) or to pasteurized breast milk (clinicaltrials.gov identifier NCT00659243).

In light of the prior art, and the long felt need for a solution, it is therefore an object of the present invention to provide a method of increasing the absorption of at least one unsaturated fatty acids, such as essential fatty acids or LCPUFAs, by a human infant, such as a preterm human infant. Said method should overcome one or more of the disadvantages of the prior art, that include: that an active ingredient that can be reliably and/or reproducibly produced in large quantities; that the active ingredient has been manufactured by a scientifically, regulatory and/or ethically acceptable method; and/or that the method or the active ingredient used in the method, has been demonstrated, within a randomized clinical trial involving human infants, to be efficacious and safe.

The solution to the above technical problem is provided by the various aspects and embodiments of the present invention as defined or otherwise disclosed herein and/or in the claims.

SUMMARY

In one aspect, the invention relates to a method to increase the absorption by a human infant of at least one unsaturated fatty acid, said method comprising the step of enteral administration of recombinant human bile-salt-stimulated lipase to said infant.

In another aspect, the invention relates to a therapeutic method to treat a human infant in need of at least one unsaturated fatty acid, said method comprising the step of enteral administration of recombinant human bile-salt-stimulated lipase to an infant in medical need thereof.

In yet another aspect, the invention also relates to a method to improve the visual and/or cognitive development of a human infant, said method comprising the step of enteral administration of recombinant human bile-salt-stimulated lipase to said infant.

Another aspect of the invention relates to a kit for the preparation of a modified infant formula or modified breast milk for use in: (a) increasing the absorption by a human infant of at least one unsaturated fatty acid; and/or for use in (b) improving the visual and/or cognitive development of a human infant; said kit comprising the components:
　a. at least one first container that includes a first amount of recombinant human bile-salt-stimulated lipase, preferably in a lyophilized formulation; and b. at least one second container, which is distinct from the first container, that includes a second amount of unmodified infant formula or unmodified pasteurized breast milk;

where said lipase and said unmodified infant formula, or unmodified pasteurized breast milk, are each in an amount sufficient to prepare a modified infant formula or modified pasteurized breast milk, respectively, that includes an amount of said lipase effective to: (a) increase the absorption of said unsaturated fatty acid by said infant; and/or to (b) improve the visual and/or cognitive development of said infant; when said modified infant formula or modified pasteurized breast milk is fed to said infant, such as is fed to said infant for at least one feed per day over at least around 4 days, for at least one feed per day over at least around 5 days, or for at least one feed per day over at least around 7 days;

said kit further comprising:

c. instructions that describe: (A) that said infant is in need of, or shall be in need of: (a) at least one unsaturated fatty acid; and/or in need of (b) improvement of visual and/or cognitive development; and/or that describe (B) that recombinant human bile-salt-stimulated lipase has been shown to be efficacious and safe in a clinical trial and to increase the absorption by a human infant (or otherwise increase the availability to a human infant) of at least one unsaturated fatty acid.

In yet another aspect, the invention relates to a method to: (a) increase the absorption by a human infant of at least unsaturated fatty acid; and/or to (b) improve the visual and/or cognitive development a human infant; said method comprising the steps of:

i. preparing or otherwise providing a modified infant formula or a modified pasteurized breast milk that comprises recombinant bile-salt-stimulated lipase, or preparing a modified infant formula or a modified pasteurized breast milk by using the kit of the invention;

ii. feeding the modified infant formula or modified pasteurized breast milk so prepared or otherwise provided to said infant; and iii. repeating the preceding steps for at least one feed per day over at least around 4 days, for at least one feed per day over at least around 5 days, or for at least one feed per day over at least around 7 days.

In a yet further aspect, the invention relates to a packaged-pharmaceutical-product comprising a pharmaceutical composition that includes an amount of recombinant human bile-salt-stimulated lipase, wherein said packaged-pharmaceutical-product further comprises instructions that describe the steps of:

i. preparing a modified infant formula or modified pasteurized breast milk that contains an amount of said lipase; and ii. enteral administration of said amount of lipase by feeding said modified infant formula or modified pasteurized breast milk to a human infant, such as for at least one feed per day over at least around 4 days, for at least one feed per day over at least around 5 days, or for at least one feed per day over at least around 7 days;

wherein said instructions describe: (A) that said infant is in need of, or shall be in need of: (a) at least one unsaturated fatty acid; and/or in need of (b) improvement of visual and/or cognitive development; and/or describe (B) that recombinant human bile-salt-stimulated lipase has been shown to be efficacious and safe in a clinical trial and to increase the absorption by a human infant (or otherwise increase the availability to a human infant) of at least one unsaturated fatty acid In a particular aspect, the invention also relates to recombinant human bile-salt-stimulated lipase for use in: (a) increasing the absorption by a human infant of at least one unsaturated fatty acid; and/or for use in (b) improving the visual and/or cognitive development of a human infant.

In another particular aspect, the invention also relates to a pharmaceutical composition comprising recombinant human bile-salt-stimulated lipase, said pharmaceutical composition for use in: (a) increasing the absorption by a human infant of at least one unsaturated fatty acid; and/or for use in (b) improving the visual and/or cognitive development of a human infant.

BRIEF DESCRIPTION OF THE FIGURES

FIG. 1.1 shows a schematic presentation of the structure of rhBSSL, also showing sites for potential glycosylation.

FIG. 2.1 shows a schematic plan of the clinical studies of rhBSSL added to infant formula or to pasteurized breast milk.

FIG. 2.2 shows correlation between differences in growth velocity (g/kg/day) and CFA (%), combined data, for the PP population.

DETAILED DESCRIPTION

In one aspect, the present invention relates to a method to increase the absorption by a human infant of at least one unsaturated fatty acid, said method comprising the step of enteral administration of recombinant human bile-salt-stimulated lipase to said infant. In an alternative aspect of the invention, enteral administration of said lipase is used in a method to increase the availability to a human infant of at least one unsaturated fatty acid. In certain embodiments, this aspect is a non-medical method.

In related aspects of the present invention, the forgoing methods (and any of their respective embodiments) are alternatively represented as: recombinant human bile-salt-stimulated lipase for use in increasing the absorption by a human infant of at least one unsaturated fatty acid, or for use in increasing the availability to a human infant of at least one unsaturated fatty acid, in each case wherein said lipase is enterally administered. In other related aspects of the present invention, the forgoing methods (and any of their respective embodiments) may be also represented as: a use of recombinant human bile-salt-stimulated lipase in the manufacture of a pharmaceutical composition for use in increasing the absorption by a human infant of at least one unsaturated fatty acid, or for use in increasing the availability to a human infant of at least one unsaturated fatty acid, in each case wherein said lipase is enterally administered.

The term "unsaturated fatty acid" will be readily identified by the person of ordinary skill in the art, and for example encompasses any carboxylic acid with an un-branched aliphatic tail (chain) that has at least one double bond between two adjacent carbon atoms in the chain. The two carbon atoms in the chain that are bound next to either side of the double bond can occur in a cis or trans configuration. In certain embodiments of the present invention at least one double bond in said unsaturated fatty acids is in the cis configuration. In further embodiments of the present invention, the unsaturated fatty acids may be further characterized as described elsewhere herein.

Recombinant human bile-salt-stimulated lipase (rhBSSL) useful in the invention is described, defined or referred to herein. For example, it includes polypeptides recognizable by a person of ordinary skill in the art as being human bile-salt-stimulated lipase, wherein said human lipase has been produced by or isolated from a non-human source, such as a non-human organism, adapted or modified (for example by recombinant genetic technology) to produce such polypeptide.

Human bile-salt-stimulated lipase (BSSL) is an enzyme known by various identifiers or aliases; for example, "carboxyl ester lipase (CEL)", "bile-salt-activated lipase (BAL)", "bile-salt-dependent lipase (BSDL)", "carboxylesterase", "carboxylic ester hydrolase" (CEH), and a number of other alias and descriptions as will be readily available to the person ordinarily skilled in the art from information sources such as "GeneCards" (www.genecards.org). A number of natural amino acid sequences and isoforms of human BSSL have been identified from human milk (and pancreas), and a number of different amino acid sequences (typically, predicted from cDNA or genomic sequence) have been described; all of which herein are encompassed within the term "human bile-salt-stimulated lipase". For example, human bile-salt-stimulated lipase is naturally produced first as a precursor sequence including a 20 to 26 amino acid signal sequence, and the mature full-length form of the protein described as having 722 to 733 amino acids (for example see, Nilsson et al, 1990; WO 91/15234, WO 91/18923; the polypeptide predicted from cDNA sequence GenBank submission ID: X54457; GenBank ID: CAA38325.1; GeneCards entry for "CEL/BSSL"; GenBank ID: AAH42510.1; RefSeq ID: NP_001798.2; Swiss-Prot ID: P19835). In further examples, other shorter isoforms of human bile-salt-stimulated lipase are described in Venter et al (2001; Science, 291: 1304-1351); GenBnk ID: AAC71012.1; Pasqualini et al (1998; J Biol Chem, 273: 28208-28218); GenBank ID: EAW88031.1; WO 94/20610 and Blackberg et al (1995; Eur J Biochem, 228: 817-821).

In particular embodiments, the human bile-salt-stimulated lipase comprises a protein having an amino acid sequence comprising, or as shown by, SEQ ID. NO. 1. In other particular embodiments, the (recombinant) human bile-salt-stimulated lipase has an amino acid sequence of either the mature or precursor forms of BSSL selected from those disclosed in Nilsson et al, 1990; WO 91/15234, WO 91/18923; RefSeq ID: NP_001798.2; GenBank ID: AAH42510.1; GenBank ID: CAA38325.1; GeneCards entry for "CEL/BSSL"; Swiss-Prot ID: P19835. In further such embodiments, the (recombinant) human bile-salt-stimulated lipase comprises a protein with an amino acid sequence that is at least 720 consecutive amino acids of any of the sequences disclosed in the preceding references or of SEQ ID. NO. 1. In other embodiments the (recombinant) human bile-salt-stimulated lipase comprises a protein having at least the amino sequence from position 1 to 101 of that disclosed in SEQ ID. NO. 1. or WO 91/15234, or at least the amino acid sequence from position 1 to 535 of that disclosed in SEQ ID. NO, 1, such as "Variant A" disclosed in Hansson et al, 1993; J Biol Chem, 35: 26692-26698, wherein such protein has bile-salt-binding and/or bile-salt-dependent lipase activity, as for example may be determined by the methods disclosed in Blackberg et al (1995; Eur J Biochem 228: 817-821).

It will now therefore be apparent to the person ordinarily skilled in the art that in certain embodiments of the present invention one or more of these described forms of (recombinant) human bile-salt-stimulated lipase may be useful in the various aspects of the invention. Further, it will be apparent to such person that other (recombinant) proteins that have bile-salt-dependent lipolytic activity (for example, as may be determined by the methods disclosed in Blackberg et al, 1995) and that are similar in amino acid sequence to those polypeptide sequences described, defined or referred to herein may also have utility in the present invention, and hence are also encompassed by the term "human bile-salt-stimulated lipase". In certain such embodiments, a protein that shows more than 90%, 95%, 98%, 99%, 99.5% sequence identity over at least about 30, 50, 100, 250, 500, 600, 700, 711, 720, 722, 733 or 750 amino acids to a sequence described, defined or referred to herein. In other embodiments, one or more amino acid substitutions may be made to one of the BSSL polypeptide sequences disclosed, defined or referred to herein. For example, one, two, three, four, five or up to 10 amino acid substitutions, deletions or additions may be made to the sequence disclosed in SEQ ID. NO. 1. Such amino acid changes may be neutral changes (such as neutral amino acid substitutions), and/or they may affect the glycosylation, binding, catalytic activity or other properties of the protein in some (desired) manner. Proteins with such substitutions, providing they have bile-salt-dependent lipolytic activity, will also be recognized by the person ordinarily skilled in the art as being "human bile-salt-stimulated lipase" in the sense of the present invention.

In other embodiments the human bile-salt-stimulated lipase is expressible from or otherwise encoded by a nucleic acid having a suitable nucleic acid sequence. By way of non-limited example, said lipase is expressible from or otherwise encoded by a nucleic acid comprising the sequence between positions 151 and 2316 of SEQ ID. NO. 2, or that disclosed in WO 94/20610 or Nilsson et al (1990). As will also be appreciated by the person of ordinary skill, a "suitable nucleic acid sequence" will also encompass variants of the preceding nucleic acid sequences. For example, changes in one or more nucleotide bases that do not change the amino acid encoded by a triplet-codon (such as in the $3^{rd}$ codon position) will also be "suitable". Sub-fragments of such nucleic acid sequences will also be "suitable" if they encode a (short) isoform of human bile-salt-stimulated lipase as described herein. Furthermore, nucleic acid sequences that encode a protein having a variant of the amino acid sequence shown by SEQ ID. NO. 1, such as those described above, will also be "suitable". Accordingly, the present invention envisions embodiments whereby the (recombinant) human bile-salt-stimulated lipase is a protein that is expressible or otherwise encoded by a nucleic acid that hybridizes to a nucleic acid comprising the sequence between positions 151 and 2316 of SEQ ID. NO. 2 or to one comprising the sequence between positions 151 and 755, and wherein said protein has bile-salt-dependent lipolytic activity. In certain such embodiments, the hybridization is conducted at stringent conditions, such as will be known to the person of ordinary skill, and is described in general text books for example "*Molecular Cloning: A Laboratory Manual*," by Joe Sambrook and David Russell (CSHL Press).

In a particular embodiment, the (recombinant) human bile-salt-stimulated lipase is produced by expression from a nucleic acid described, defined or referred to herein.

A human bile-salt-stimulated lipase described, defined or referred to herein, in the context of the present invention is a recombinant bile-salt-stimulated lipase (rhBSSL); i.e. where said human lipase has been produced by or isolated from a non-human source, such as a non-human organism, adapted or modified (for example by recombinant genetic technology) to produce such lipase. In particular embodiments, the rhBSSL is produced using cell-free and/or in-vitro transcription-translation techniques from an isolated nucleic acid molecule described, defined or referred to herein. Alternatively, a recombinant non-human organism is used, wherein said non-human organism includes at least one copy of such a nucleic acid, and where said nucleic acid is expressible by said nonhuman organism to produce the desired protein: rhBSSL. For example, recombinant bacterial, algae, yeast or other eukaryotic cells may be used, and the rhBSSL is, in certain embodiments, produced from the culture of such recombinant cells. In other embodiments, the rhBSSL may be produced by extra-corporal culture of modified or specifically selected human cells, for example by their in-vitro culture. In yet other embodiments, rhBSSL may be produced by its isolation from the milk of transgenic animals; such as transgenic cattle, sheep, goats or rabbits. The skilled person will be aware of the numerous technologies available to produce human bile-salt-stimulated lipase using recombinant technology.

Recombinant human bile-salt-stimulated lipase has been shown to be producible from recombinant cell culture including the culture of *E. coli*, mouse and hamster (Hansson et al, 1993), and *P. pastoris* (Trimple et al, 2004; Glycobiol, 14: 265-274) cells. Recombinant human bile-salt-stimulated lipase has also been shown to be producible and isolatable from the milk of transgenic mice (Stromqvist et al, 1996; Transgen Res, 5: 475-485) and from the milk of transgenic sheep (WO 99/54443). In certain embodiments of the present invention, the recombinant human bile-salt-stimulated lipase is isolated from the culture of such recombinant cells or from the milk of such transgenic animals. In an alternative embodiment, the recombinant human bile-salt-stimulated lipase is not one isolated from the milk of a transgenic sheep or a transgenic mouse.

In a particular embodiment of the present invention, the recombinant human bile-salt-stimulated lipase is isolated from an expression product of a recombinant Chinese hamster ovary (CHO) cell line, is produced by a recombinant CHO cell line, or is expressible by, or isolatable from, a recombinant CHO cell line. Use of a recombinant CHO cell line expression system to produce such lipase can produce rhBSSL that exhibits particular structural, activity or other characteristic features, such as one or more of those described herein. By way of non-limiting example, the rhBSSL useful in the present invention may be isolated using a process and/or exhibit characteristics analogous to, or substantially as described in, the Exemplification herein.

In certain embodiments of the present invention, the recombinant human bile-salt-stimulated lipase is identified by the International Non-proprietary Name (INN) stem "bucelipase" (see WHO Drug Information, 21: 62, 2007), for example because it has the amino acid sequence shown therein. The recombinant human bile-salt-stimulated lipase, when used in the present invention may, with reference to SEQ ID. NO. 1, have one or more disulfide bridges at the locations Cys64-Cys80 and Cys246-Cys257, and/or is glycosylated at one or more of the possible glycosylation sites at Asn-187, Thr-538, Thr-549, Thr-559, Thr-576, Thr-587, Thr-598, Thr-609, Thr-620, Thr-631 and Thr-642 (in one such embodiment, schematically represented in FIG. 1.1). In certain such embodiments, the rhBSSL is in a glycoform, and may for example, have the INN of "bucelipase alfa."

In other particular of the present invention, the recombinant human bile-salt-stimulated lipase has structural, composition and/or other properties that are different to those of native human bile-salt-stimulated lipase (BSSL-MAM) and/or different from that form of recombinant bile-salt-stimulated lipase that has been produced by isolation from the milk of transgenic sheep (rhBSSL-OVI), such as described in WO 99/54443.

Accordingly, in certain such embodiments, the recombinant human bile-salt-stimulated lipase useful for the present invention is (substantially) free of other milk proteins or milk components. As will be apparent upon the disclosure of the present invention, in certain embodiments the rhBSSL is added to a milk-based infant feed before administration to the human infant. Accordingly, in such embodiments, the "free of other milk proteins or milk components" will apply to that form, composition or formulation of the recombinant bile-salt-stimulated lipase that exists shortly before (such as immediately before) addition of said lipase to said milk-based infant food. For example, in such embodiments the pharmaceutical compositions or kits components of the invention containing rhBSSL, or that amount of rhBSSL that is provided ready for addition to any infant formula and/or pasteurized breast milk, are free of such milk-based contaminates. In certain such embodiments, the rhBSSL is free of milk casein and whey proteins, such as lactoferrin, or free of other contaminates native to milk, in particular where such milk-derived proteins or other contaminates are derived from the milk of humans, sheep or mice. In these embodiments, the "free of" any particular such protein or contaminant means that no material amounts of such protein or other contaminate can be detected by routine detection methodologies. Alternatively, any such particular impurity may be present at a level of less than about 5%, such as less than about 2%, 1%, 0.5% or 0.1%, or is essentially or effectively absent, or that the total of all such milk-derived proteins or other contaminates are present at a level of less than about 5%, such as less than about 2%, 1%, 0.5% or 0.1%, or are essentially or effectively absent. As will be understood by the person ordinarily skilled in the art, recombinant human bile-salt-stimulated lipase produced & isolated from cell culture, such as from recombinant CHO cells will be considered "free of" such milk-based contaminates.

In other certain such embodiments of the present invention, the recombinant human bile-salt-stimulated lipase has purity of greater than about 70%, such as a purity of greater than about 80%, 90% or 95%. In particular such embodiments, such percentage purity is a percentage purity of total protein. As described above, in the applicable embodiments such purity measure is that of the composition comprising said lipase before addition to any infant feed or other administration medium. Such purity values may be determined by RP-HPLC, SE-HPLC or SDS-PAGE (with SyproRuby or silver staining) techniques.

In other embodiments of the invention, particularly if the recombinant human bile-salt-stimulated lipase is produced using (expressed from) recombinant CHO cells, the rhBSSL when used in the present invention may be characterized by one or more structural, activity or other properties such as those described in the following.

In further certain such embodiments of the invention, the recombinant human bile-salt-stimulated lipase has a level (overall/total) of glycosylation that is less than that of native human bile-salt-stimulated lipase (BSSL-MAM) and/or has a level (overall/total) of glycosylation that is more than that of recombinant human bile-salt-stimulated lipase isolated from the milk of transgenic sheep (rhBSSL-OVI). The levels of glycosylation, such as the level of monosaccharide and/or sialic acid content of BSSL (or sample thereof) may be measured using high pH anion exchange chromatography with pulsed amperiometric detection (HPAEC-PAD). In particular embodiments of the present invention, the total monosaccharide content of the recombinant human bile-salt-stimulated lipase (moles monosaccharide per mole rhBSSL) is between about 20 and 100, between about 25 and 65 or between about 25 and 55, such as between about 40 to 45 mole/(mole rhBSSL), In certain embodiments of the invention the total sialic acid content of the rhBSSL (moles sialic acid per mole rhBSSL) is between about 20 and 35, such as between about 25 and 30 mole/(mole rhBSSL).

In yet other such embodiments of the present invention, the recombinant human bile-salt-stimulated lipase has a glycosylation pattern, for example of O-glycans, that is different to that of BSSL-MAM and/or different to that of rhBSSL-OVI. Such differences may be detected using capillary electrophoresis with laser induced fluorescence detection (CE-LIF) and/or HPAEC-PAD. In particular embodiments of the invention, the rhBSSL may have between about 20 and 50 mole of N-acetyl neuraminic acid (NANA=Neu5Ac) per mole rhBSSL [mole/(mole rhBSSL)], such as between about 25 and 40 mole/(mole rhBSSL). The rhBSSL used in the invention may have less than about 5 mole N-glycosyl neuraminic acid (NGNA=Neu5Gc) per mole rhBSSL, such as less than about 2 mole/(mole rhBSSL), or where NGNA is essentially undetectable. The rhBSSL used in the invention may have less than about 20 mole fucose per mole rhBSSL, such as less than about 10, less than about 5, less than or about 2 mole/(mole rhBSSL), and in certain embodiments fucose is essentially undetectable. The rhBSSL used in the invention may have between about 5 and 25 mole galactosamine per mole rhBSSL, such as between about 10 and 20 or between about 15 and 18 mole/(mole rhBSSL). The rhBSSL used in the invention may have less than about 10 mole glucosamine per mole rhBSSL, such as less than about 5, less than about 3 or about 2 mole/(mole rhBSSL). The rhBSSL used in the invention may have between about 5 and 25 mole galactose per mole rhBSSL, such as between about 10 and 20 or between about 15 and 18 mole/(mole rhBSSL). The rhBSSL used in the invention may have less than about 5 mole glucose per mole rhBSSL, such as less than about 2 mole/(mole rhBSSL), or where glucose is essentially undetectable. The rhBSSL used in the invention may have between about 2 and 8 mole mannose per mole rhBSSL, such as between about 4 and 6 mole/(mole rhBSSL). In particular embodiments of the invention, the rhBSSL may have a profile of monosaccharide and/or sialic acid content about that as, or substantially as, represented in Table 1.1.

In other embodiments of the invention, the recombinant human bile-salt-stimulated lipase useful for the present invention is different from BSSL-MAM and from rhBSSL-OVI in the profile or amount of lectin binding or Lewis-antigen binding tests, such as those assays and profiles described in Blackberg et al (1995) and Landberg et al (1997) respectively. Such lectin binding or Lewis-antigen binding tests can indicate differences in glycosylation pattern between these different forms of BSSL. Other techniques may be used to identify and/or characterize recombinant human bile-salt-stimulated lipase useful for the present invention. For example, rhBSSL may be characterized (and/or differentiated from BSSL-MAM or from rhBSSL-OVI) by endoprotease Lys-C digestion followed by analysis of the resulting peptides with reverse-phase HPLC with quantitative UV detection (at 214 nm), and recording/inspection of the resulting chromatogram. Differences in the resulting chromatogram may be due to—and hence further reflect—unique features of glycosylation of specific peptides comprising the rhBSSL that have specific differences in retention time.

In yet further embodiments of the present invention, the recombinant human bile-salt-stimulated lipase has a molecular mass of between 90 KDa and 75 KDa. In particular such embodiments the molecular mass of said lipase is between about 84 and 86 KDa, such as about 85 KDa. The molecular mass may be determined by routine techniques including MALDI-MS. By way of comparison, using the same detection techniques the molecular mass of BSSL-MAM is measured as being substantially greater (for example, around 100 KDa) and that of rhBSSL-OVI is measured as being substantially smaller (for example, around 78 KDa).

In other further such embodiments of the present invention, the recombinant human bile-salt-stimulated lipase can comprise a population of recombinant human bile-salt-stimulated lipase molecules having sequences of different amino acid lengths. In certain of such embodiments, the amount of lipase molecules that are present in a form that is shorter at the C-terminal end by one, two, three, four, five or up to ten amino acids, compared to the longest or (predicted) full-length form (such as that shown by SEQ ID. NO. 1) is greater than 50% of the amount of lipase molecules present in such longest or (predicted) full-length form. In certain such embodiments, between about 100% and 500% of the amount of the longest (or predicted full-length) lipase molecule is the amount present as a shorter lipase molecule, such as by one or two amino acids from the C-terminal end. In particular such embodiments between about 200% and 400%, for example about 300%, of the amount of the longest (or predicted full-length) molecule (for example, that shown by SEQ ID. NO. 1), is the amount present as a shorter lipase molecule such as by one or two amino acids from the C-terminal end. In particular embodiments or the foregoing, less than 1% of the amount of the longest (or predicted full length) said lipase molecules is present as a lipase molecule shorter by two amino acids. In other embodiments, between two- to five-fold, such that about three-fold, the number of longest (or predicted) said lipase molecules are present in a form that are shorter than such longest (or predicted) molecule from the C-terminal end by one, two, three, four, five or up to ten amino acids.

In yet other further such embodiments of the present invention, the recombinant human bile-salt-stimulated lipase may have a specific activity that is greater than BSSL isolated from human milk and/or rhBSSL-OVI. For example, the specific activity of the rhBSSL may be between about 15% and 35% higher, such as about 20% or 25% higher specific activity than that of BSSL-MAM and/or rhBSSL-OVI (based on mass). Techniques to measure specific activity of human BSSL will be known to the person of ordinary skill and include using the 4-nitrophenyl ester butyric acid (PNPB) assay as generally described in the Exemplification herein. Other in-vitro assays for BSSL are known, for example by use of trioleoylglycerol emulsified in gum Arabic as the substrate for BSSL and sodium cholate (10 mM) as activating bile salt (for example, as described by Blackberg and Bernell, 1981; Eur J Biochem, 116: 221-225). In particular embodiments, prior to measuring specific activity, the BSSL may be purified to a high purity, such as by using the techniques of heparin-affinity chromatography and size exclusion chromatography.

As will be understood by the person of ordinary skill, the recombinant human bile-salt-stimulated lipase used in the present invention may be characterized by more than one of the distinguishing features described or defined herein, such as those above. For example, a combination of two or more (such as three, four, five or more) of such features may together characterize a particular embodiment of the recombinant human bile-salt-stimulated lipase for use in the present invention.

An increase, or otherwise an improvement or enhancement in, the absorption of or availability to the particular unsaturated fatty acid(s) by the human infant (or a population/sample of human infants) may be detected, investigated, monitored or observed by various means known in the art. For example, by inspection of the fat-balance between fat-input and fat-excretion of fatty acid quantified through the use of gravimetric analysis of fatty acids, such as used by Andersson & coworkers (2007). Alternatively, quantification of individual fatty acids may be conducted using gas chromatographic methods such as described in the Exemplification herein. Sidisky & coworkers (1996; The Reporter [Supelco/Sigma-Aldrich], 15(1):1-4) describe the properties of various capillary columns to aid the selection of appropriate columns to separate and hence detect key fatty acid methyl esters. The degree of fat absorption may be quantitatively expressed as a coefficient of fat absorption (CFA) for any specific, sub-group or group of similar or related fatty acids, or for all/overall fatty acids (i.e. the most abundant fatty acids) by appropriate summing of values for individual fatty acids, such as is described in more detail in the Exemplification below. As a further example of methodology, for an individual human infant (or group thereof), an improvement in unsaturated fatty acid absorption, such as the absorption of DHA or AA, may be investigated, monitored, followed and/or checked, for example by analysis of the absolute or relative fatty-acid content, over time or during treatment, of plasma or red blood cell membrane phospholipids (Carlson et al, 1996; Pediatr Res, 39: 882-888; Boehm et al, 1996), including the use of chromatographic (GC) separation of individual fatty acids followed by identification/quantification for example by using mass spectrometry. Methodologies to measure growth velocity are disclosed elsewhere herein.

The inventors describe herein the basis of the invention; that within clinical trials administering recombinant bile-salt-stimulated lipase to human infants, there is an increase in the coefficient of absorption by said infant of unsaturated fatty acids, and also for certain groups of, and more particularly specific, unsaturated fatty acids.

In contrast to this effect, and as described in more detail within the Exemplification below, the inventors show that in accordance with a limited and non-significant increase in overall CFA (i.e., for all or for the most abundant fatty acids), there was also only a very limited and non-significant difference in the CFA of saturated fatty acids between the treatment groups in infants of the per-protocol set (PP) of the clinical trials. Human infants when administered rhBBSL had only a LS mean increase of 2.25% of CFA (p=0.236) for saturated fatty acids compared to when they were administered placebo. Indeed, in those infants fed infant formula, there was no effective difference in the CFA of saturated fatty acids (LS mean difference 0.08%; p=0.975) between when infants were administered rhBSSL compared to when administered placebo, and nor was there a significant difference between the infants' treatments when fed with breast milk. Saturated fatty acids for this analysis are those fatty acids (independent of aliphatic chain length) that have no double bond.

The following effects further support the basis of the invention.

Firstly, in the general group of all unsaturated fatty acids, there is a significant increase in the CFA of unsaturated fatty acids by those infants in the per-protocol set (PP) of the clinical trials when administered recombinant bile-salt-stimulated lipase compared to when administered placebo. Human infants when administered rhBBSL had a LS mean increase of 4.22% of CFA (p=0.034) for unsaturated fatty acids compared to when these infants were administered placebo. Such an effect was also seen in each individual clinical trial (infants treated with infant formula or breast milk) with those infants fed breast milk having a large and significant effect upon administration with rhBSSL (LS mean difference 5.10%, p=0.044). The effect observed in those infants fed infant formula was not significant (p=0.286), but did show an increase in CFA for unsaturated fatty acids (LS mean difference 3.25%) which contributed to the overall effect and statistical significance in the combined analysis. Unsaturated fatty acids for this analysis are those fatty acids (independent of aliphatic chain length) that have at least one double bond.

Secondly, in the general sub-group of all polyunsaturated fatty acids, there also was a significant and more substantial increase in the CFA of polyunsaturated fatty acids when infants in the per-protocol set (PP) of the clinical trials were administered recombinant bile-salt-stimulated lipase compared to when administered placebo. Human infants when administered rhBBSL had a LS mean increase of 5.82% of CFA (p=0.005) for polyunsaturated fatty acids compared to when these infants were administered placebo. Such an effect was also seen in each individual clinical trial (infants treated with infant formula or breast milk) with those infants fed breast milk having a large and significant effect upon administration with rhBSSL (LS mean difference 6.92%, p=0.020). The effect observed in those infants fed infant formula was not statistically significant at the 0.05 level (p=0.093), but did show a considerable increase in CFA for unsaturated fatty acids (LS mean difference 5.05%) which contributed to the overall effect and statistical significance in the combined analysis. Polyunsaturated fatty acids for this analysis are those fatty acids (independent of aliphatic chain length) that have at least two double bonds.

Thirdly, in the specific sub-group of LCPUFAs—those fatty acids of particular importance for the developing infant as described elsewhere herein—there was an even greater increase in the CFA of LCPUFAs by those infants in the per-protocol set (PP) of the clinical trials when administered recombinant bile-salt-stimulated lipase compared to when administered placebo. Human infants when administered rhBBSL had a LS mean increase of 7.33% of CFA (p=0.002) for LCPUFAs compared to when these infants were administered placebo. Such an effect was also seen in each individual clinical trial (infants treated with infant formula or breast milk) with those infants fed breast milk having a large and significant effect upon administration with rhBSSL (LS mean difference 8.02%, p=0.012). The effect observed in those infants fed infant formula was not quite statistically significant at the 0.05 level (p=0.054), but did also show a large increase in CFA for unsaturated fatty acids (LS mean difference 7.01%) which contributed to the large overall effect and highly statistical significance in the combined analysis. LCPUFAs for this analysis are those fatty acids having at least 20 carbon atoms in the aliphatic chain and that have at least two double bonds.

Of particular unity for the present invention is that administration of recombinant bile-salt-stimulated lipase to human infants results in a large and statistically significant increase in the absorption of the conditionally essential fatty acids arachidonic acid (AA; C20:4 n-6) and docosahexaenoic acid (DHA; C22:6 n-3). Human infants when administered rhBBSL had a LS mean increase of 8.63% of CFA for AA (95% confidence interval [CI]=3.60 to 13.67) compared to when these infants were administered placebo, and a LS mean increase of 5.80% of CFA for DHA (95% CI=1.30 to 10.29). Such effects were also seen in each individual clinical trial (infants treated with infant formula or breast milk) with those infants fed breast milk having large and significant effects upon administration with rhBSSL. The effects observed in those infants fed infant formula were not statistically significant, but did also show a large increase in CFA for these fatty acids which contributed to the large overall effects and highly statistical significance in the combined analyses.

Also of particular unity for the present invention is that administration of recombinant bile-salt-stimulated lipase to human infants results in a large increase in the absorption of the essential fatty acids linoleic acid (LA; C18:2 n-6) and alpha-linolenic acid (LNA; C18:3 n-3). Human infants when administered rhBBSL had a LS mean increase of 5.79% of CFA for LA (95% CI=1.82 to 9.76) compared to when these infants were administered placebo, and LS mean increase of 3.66% of CFA for LNA (95% CI=−1.24 to 8.55). Such effects were also seen in each individual clinical trial (infants treated with infant formula or breast milk) with those infants fed breast milk having a large statistically significant effect on LA absorption upon administration with rhBSSL.

As is described in more detail in the Exemplification below, the administration of recombinant bile-salt-stimulated lipase to human infants results in an increase in the absorption of the unsaturated fatty acids eicosadienoic acid (C20:2 n-6) and dihomo-gamma-linolenic acid (C20:3 n-6)/eicosatrienoic acid (C20:3 n-3). This effect was only observed for infants fed breast milk, as the infant formula was not formulated to contain such fatty acids. As will also be observed from Table 2.14 (breast milk study), administration of recombinant bile-salt-stimulated lipase to human infants also results in a large numerical increase in the absorption of the all unsaturated fatty acids having an having at least 20 carbon atoms in the aliphatic chain.

It is also demonstrated by the inventors that the administration of recombinant bile-salt-stimulated lipase to human infants shows an increase in the absorption of the specific saturated fatty acid myristic acid (MA; C14:0). Human infants when administered rhBSSL had a LS mean increase of 4.81% of CFA for MA (95% CI=0.24 to 9.38) compared to when these infants were administered placebo.

There have been experimental suggestions that the significance of milk-BSSL in infants may be not just to aid absorption of fatty acids. For example, Miller & Lowe (2008; J Nutr 138: 927-930) observed that in CEL-(BSSL) deficient mice, only the absence of both mother's milk and pancreatic CEL (BSSL) produces fat malabsorption; the absence of only mother's milk CEL (BSSL) did not affect the efficacy of dietary fat absorption, and that even with increased fecal fats, the CEL-(BSSL) deficient mouse pups had normal weight gain. Also, and in particular, Howles and coworkers (1999; Am J Physiol, 277: G653-G661) have speculated—following experiments using CEL-(BSSL) deficient mice—that CEL (BSSL) may prevent fat-derived intestinal injury in neonatal mice, in particular due to the accumulation of excess lipid in the epithelium of the distal small intestine (see also, Lindquist et al, 2007; J Pediatr Gastroenterol Nutr 44: E335, as reported by Lindquist & Hernell, 2010). Indeed, it was observed in the clinical trials disclosed herein that infants (in the PP data set) fed with infant formula were exposed to a larger amount of total fat (and excreted more fat in their stools) between the food tracer markers of each treatment period (total fat exposure: 29.12 g fat for rhBSSL and 28.50 g fat for placebo) compared to the infants fed with breast milk (19.00 g fat for rhBSSL and 20.51 g fat for placebo) [figures not corrected for any differences in body weight]. This observed difference in total fat exposure between those infants fed formula compared to breast milk, in light of the speculated protective role of BSSL described above, could be a factor to explain the difference in CFA of particular fatty acids seen between the formula-fed and the breast-milk fed infants. There was little difference between the mean volume of milk or formula ingested between the studies and/or between the treatment periods.

In a first particular embodiment of the present invention, the unsaturated fatty acid is an essential fatty acid, such as one that humans must ingest for good health because the body requires them but cannot make them from other food components. Essential fatty acids include alpha-linolenic acid (LNA) and linoleic acid (LA). Some fatty acids such as gamma-linolenic acid (GLA), eicosapentaenoic acid (EPA), arachidonic acid (AA) and docosahexaenoic acid (DHA) are manufactured in the human body from the essential fatty acids LA and LNA. Due to limitations in the metabolism of LA and LNA, GLA, AA, EPA and DHA may become conditionally essential. During the rapid growth phase of the human brain during the last trimester of fetal life and within the first 2 years of childhood, the fatty acids GLA, EPA, AA and DHA may become limiting, in particular for pre-term infants. Accordingly, in certain such embodiments of the invention, the unsaturated fatty acid is a conditionally essential fatty acid such as GLA, EPA, AA and/or DHA.

In a second particular embodiment of the present invention, the unsaturated fatty acid is a polyunsaturated fatty acid; that is, a fatty acid that has at least two double bonds, each between an adjacent pair of carbon atoms within the fatty acid's aliphatic tail (chain). The two carbon atoms in the chain that are bound next to either side of a double bond can occur either in a cis or trans configuration. In certain embodiments of the present invention at least one of the double bonds in said polyunsaturated fatty acids is in the cis configuration, and in particular such embodiments, all double bonds of the polyunsaturated fatty acid are in the cis configuration In a third particular embodiment of the present invention, the unsaturated fatty acid has an aliphatic tail (chain) that has a length of at least twenty (20) carbon atoms.

In a fourth particular embodiment of the present invention, the unsaturated fatty acid is a polyunsaturated fatty acid (i.e. one with at least two double bonds) that has an aliphatic tail (chain) that has a length of at least twenty (20) carbon atoms. A fatty acid that has an aliphatic tail (chain) with a length of at least twenty (20) carbon atoms and at least two double bonds, each between an adjacent pair of carbons with the fatty acid's aliphatic tail (chain), is known in the various aspects and embodiments of the present invention as a "Long Chain Polyunsaturated Fatty Acid" (LCPUFA).

In certain embodiments of all aspects of the present invention, the at least one unsaturated fatty acid is one selected from the group consisting of: eicosadienoic acid (C20:2 n-6), dihomo-gamma-linolenic acid (C20:3 n-6), eicosatrienoic acid (C20:3 n-3), arachidonic acid (C20:4 n-6) and docosahexaenoic acid (C22:6 n-3), linoleic acid (C18:2 n-6) and alpha-linolenic acid (C18:3 n-3). The person of ordinary skill in the art will be readily able to recognize such fatty acids from the trivial name and/or "C:D" lipid numbers in combination with, if necessary, the "n-x" nomenclature.

In particular such embodiments, the unsaturated fatty acid(s) is arachidonic acid (C20:4 n-6) and/or docosahexaenoic acid (C22:6 n-3).

In alternative particular such embodiments, the unsaturated fatty acid(s) is linoleic acid (C18:2 n-6) and/or alpha-linolenic acid (C18:3 n-3).

In particular embodiments of the present invention, the unsaturated fatty acid is not arachidonic acid (AA; C20:4 n-6) and/or is not docosahexaenoic acid (DHA; C22:6 n-3).

In particular embodiments of all aspects of the present invention, the increase in the absorption by (or availability to) a human infant of at least one unsaturated fatty acid is concomitant with an increase an increase in the absorption by (or availability to) said infant of the saturated fatty acid myristic acid.

In a different aspect, the present invention also relates to a method to increase the absorption by a human infant of at least the saturated fatty acid myristic acid, said method comprising the step of enteral administration of recombinant human bile-salt-stimulated lipase to said infant. In an alternative aspect of the invention, enteral administration of said lipase is used in a method to increase the availability to a human infant of at least the saturated fatty acid myristic acid.

As described elsewhere herein, the inventors observed that the present invention—as exemplified by two controlled clinical trials and an analysis of combined data from these two trials—resulted in an increase in the absorption of unsaturated fatty acids, in particular of LCPUFAs, and also growth velocity, when human infants were administered recombinant bile-salt-stimulated lipase, while observing only a limited increase in the overall absorption coefficient of (i.e. all or the most abundant) fatty acids, as measured by overall CFA (co-efficient of fat absorption). As set out in more detail within the Exemplification below, infants in the per-protocol data-set (PP) showed a statistically significant increase in growth velocity upon administration of rhBSSL compared to placebo (LS mean difference of 2.08 g/Kg/day; p=0.019) but with a less pronounced and non-significant increase in overall CFA (LS mean difference of 3.56%; p=0.069). In terms of relative (%) increases of the effects (in the PP set) compared to the LS mean effects for placebo, administration of rhBSSL increased growth velocity by 13.8% (17.15 compared to 15.06 g/Kg/day), but only increased overall CFA by 5.4% (69.06 compared to 65.50% CFA). Such an observation was more pronounced in the subset of infants fed with infant formula (PP); showing a high and statistically significant increase in growth velocity upon administration of rhBSSL compared to placebo (LS mean difference of 2.30 g/Kg/day; p=0.038) but with little concomitant (and non-significant) increase in overall CFA (LS mean difference of 2.08%; p=0.462); and the relative (%) increase compared to the LS mean effects for placebo, upon administration of rhBSSL for formula-fed infant increased growth velocity by an increase of 14.9% (17.75 compared to 15.45 g/Kg/day), but with only an increase in overall CFA of 3.1% (69.46 compared to 67.38% CFA). Furthermore, and also set out in more detail within the Exemplification herein, there was very little (non-significant) correlation between intra-individual differences in growth velocity (rhBSSL-placebo) of individual infants vs their corresponding difference in overall CFA ($R^2$ linear=0.041; p=0.177), with little of the variance observed in intra-individual differences in growth velocity accounted for by variance in the corresponding individuals' increase in overall CFA values (ANOVA following linear regression).

Other analysis approaches or methodologies may be used to further investigate and/or present results from the two clinical trials disclosed herein, including analysis approaches or methodologies that investigate and/or present results related to: (i) relative absorbance by and/or availability to particular fatty acids (or sub-groups thereof); and/or (ii) the limited concomitance between an increase in growth velocity and an increase in overall CFA, in each case for infants administered recombinant bile-salt-stimulated lipase.

Also of note from clinical trials disclosed herein is that despite the average increase in growth velocity being comparable with other infant growth studies (for example, see Andersson et al, 2007), the mean overall CFA values observed are lower (mean overall CFA in the PP data set: 69.08% for rhBSSL and 65.66% for placebo) than those that have generally been observed in other infant CFA studies (for review, see Lindquist and Hernell, 2010). However, the variation in overall CFA values for individual infants (Standard Deviation in the PP of 14.68% for rhBSSL, 16.13% for placebo and 13.19% for the intra-individual difference) generally conformed to those values generally observed in other infant CFA studies (Williamson et al, 1978; Morgan et al, 1998; Acta Paediatr 87: 318-324; Andersson et al, 2007). BSSL is known as a broad spectrum lipase that can hydrolyze many kinds of lipids and lipid-like molecules (for review, see Lindquist and Hernell, 2010), and since over half of the energy available to an infant comes from hydrolyzed lipids contained in milk, it may have been expected by the person of ordinary skill in the art that the most striking result would have been an increase in overall CFA—and that any increase in growth velocity would not be as striking as (since it would have been expected to strongly depend upon) an increase in overall CFA.

Accordingly, in certain embodiments of the present invention, the increase in absorption, or availability to, the at least one unsaturated fatty acid by the human infant is achieved, observed or desired without observing and/or achieving a concomitant increase in the overall coefficient of fat absorption (i.e., for all or the most abundant fatty acids) in said infant. In particular such embodiments of the invention, said increase in absorption, or availability to, the at least one unsaturated fatty acid is not concomitant with, indicated by and/or correlated to an increase in the overall coefficient of fat absorption (i.e. for all or the most abundant fatty acids). In other particular such embodiments, the increase in absorption, or availability to, the at least one unsaturated fatty acid is not fully explainable by (or caused by) an increase in overall CFA.

Elsewhere herein is described a number of other studies from the prior art that provide substantial evidence for a causative relationship between unsaturated fatty acids (LCPUFAs in particular; especially arachidonic acid and docosahexaenoic acid) and the visual and/or cognitive development of human infants, particularly of infants born premature.

Accordingly therefore, in certain embodiments of the present invention the absorption of (or availability to) at least one of the unsaturated fatty acids described above by the human infant may result in improvement, increase or otherwise an enhancement of the visual and/or cognitive development of said infant following administration of recombinant human bile-salt-stimulated lipase to the infant. Such enhancement of the infant's visual or cognitive development may occur through a number of mechanisms, including: visual and/or neural maturation, brain and/or retinal development, neural- and/or visual-system development and/or CNS or mental development. In certain such embodiments of the invention, the enhancement of the visual and/or cognitive development results in an outcome that is measurable from the infant, either in early life or later. For example, in certain such embodiments of the present invention, the absorption of (or availability to) at least one of the unsaturated fatty acids described above by the human infant may result in an increase in an outcome that is measurable from said infant, including: visual acuity (including stereo acuity), cognitive behavior, information processing, eye-hand coordination, intelligence quotient (IQ), psychomotor development, problem solving, verbal IQ, vocabulary development, language development, production and/or comprehension, novelty preference on visual recognition, maturation of electroencephalography (EEG) patterns, memory, information processing, and/or behavioral performance; and/or a decrease in abnormal general movement scores and/or spontaneous motor behavior. There are a number of tests and/or other investigative methods that the person of ordinary skill may use to test for improvement or enhancement of on or more of such measurable outcomes, and non-limiting examples of these tests include: the Brunet-Lezine test, Bayley Psychomotor Development index, Bayley Scale of Infant Development, Kaufmann Assessment Battery for Children (K-ABC) tests. The foregoing prior art reviews and studies describe in more detail such mechanisms, measurable outcomes and testing methodologies.

In the present invention, the amount of recombinant human bile-salt-stimulated lipase enterally administered to the human infant may vary. In certain embodiments, the amount of said lipase is an effective amount, such as an amount effective to increase the absorption by said infant of at least one unsaturated fatty acid when said lipase is administered to the infant according to present invention. Suitable amounts of recombinant human bile-salt-stimulated lipase that may be administered to the infant in any given day may range from an amount per day of between 1 and 100 mg of said lipase per Kg weight of infant. In particular embodiments between 5 and 50 mg mg of said lipase per Kg weight of infant, or between 15 and 40 mg of said lipase per Kg weight of infant may be administered over a day, such as between about 22.5 and 27 mg of said lipase administered per Kg weight of infant per day. By way of non-limiting example, a 1.5 Kg infant dosed at 25 mg/Kg/day may be administered with a total of about 37.5 mg of recombinant human bile-salt-stimulated lipase per day. In certain embodiments of the present invention, the mass of rhBSSL used or referred to herein, instead of being given as an absolute mass, is given as the mass of active rhBSSL molecules. Since different production or storage batches of rhBSSL may vary in enzymatic activity, the absolute mass of rhBSSL administered may be varied in order to compensate for such variations in activity and hence to provide a more uniform amount of active rhBSSL. The activity of rhBSSL may be easily determined using the PNPB assay as described herein, with reference to an active standard BSSL molecule. Suitable masses of active rhBSSL are within the ranges of masses given above. As the molecular mass of a complex protein such as rhBSSL may vary, for example due to differences in glycosylation, the amount of said lipase may be defined in ways other than in terms of mass, such as in terms of (active) molar amounts. The skilled person will be readily able to make other conversions from specific mg amounts to the corresponding micro mole amount. Alternatively, the amount of recombinant human bile-salt-stimulated lipase may be expressed in terms of the activity of the lipase in enzyme units (U), such as defined as the amount of said lipase that catalyzes the formation of 1 micro mole of product per minute under the conditions of the assay, for example as determined in an in vitro assay for BSSL activity such as one described herein.

As will be appreciated by the person of ordinary skill, a human infant is typically (unless for example on a glucose drip) regularly fed with a nutritional base that contains a source of fat such as triglycerides. The infant may be fed the nutritional base orally or via tube-feeding. The nutritional base (feed or food) is commonly an infant formula or human breast milk. Accordingly, certain embodiments of the invention the recombinant human bile-salt-stimulated lipase is administered to a human infant that receives a nutritional base containing a source of fat such as triglycerides that contain at least one unsaturated fatty acid. In particular such embodiments said nutritional base is an infant formula and/or pasteurized breast milk; both known by the person of ordinary skill to contain a substantial proportion of fat in triglyceride form. In various such embodiments of the invention, the enteral administration of the rhBSSL may be prior to, after or concomitant to when said infant receives the nutritional base. If administered prior to or after the receiving the nutritional base, then the rhBSSL may be administered within about 1 hour of said infant receiving the nutritional base, such as within about 30 mins, 15 mins or 5 mins, or within a period of less than about 2 min of the infant receiving the nutritional base. Should the period between receiving the nutritional base be within about 1 min of administration of the rhBSSL, then this may effectively be considered administration of the rhBSSL concomitant to said infant receiving the fat-containing nutritional base (such as an infant formula and/or pasteurized breast milk). Such concomitant (or co-) administration will occur if the rhBSSL is first added to an infant formula or breast milk, which is then fed to the human infant.

As is generally known, it is preferable to exclusively feed fresh breast milk from the infant's own mother. However, for various reasons the infant may be fed pasteurized breast milk from other mothers, such as from a breast milk bank. Alternatively, the infant may be fed, as is common, infant formula instead of or in addition to (non-fresh) breast milk. That a human infant is not fed its mother's fresh milk, but one of these alternatives, may be due to one or more causes. For example: (i) the mother may not produce enough breast milk because of health reasons such as previous breast surgery or a prolactin deficiency; (ii) the mother may suffer from mastitis, eczema, or a plugged milk duct making breast feeding painful; (iii) the infant may suffer from a disorder in the mouth, such as a cleft lip or palate; (iv) the mother may not have sufficient knowledge to breastfeed, may choose not to feed fresh breast milk, such as for reasons of culture or convenience; or (v) the mother may be advised not to feed her own fresh breast milk in order to protect the infant from potentially harmful components of her own breast milk, including the transmission of infective agents such as HIV virus, CMV virus, T-cell lymphotropic virus or tuberculosis mycobacteria, dangerous medication or drugs (or their metabolites) such as from illicit drug-use, retroviral or chemotherapy drug therapy, or if the mother is undergoing radiation therapy. Finally, the infant may be too week to feed from the breast, which can be a particular problem for preterm or underweight infants.

Accordingly, in certain embodiments of the invention the human infant is not exclusively fed fresh mothers' milk, for example the infant is not exclusively fed fresh milk from its own mother such as by exclusive breastfeeding or feeding of fresh expressed breast milk. An infant that is not fed exclusively breastfed or not exclusively fed from expressed (fresh) breast milk from its own mother will receive milk from other sources, such as infant formula or pasteurized and/or (previously) frozen breast milk from a breast milk bank. In particular embodiments of the present invention, the infant is not fed fresh mother's milk, for example the infant is exclusively fed with infant formula, pasteurized and/or frozen breast milk such as from a breast milk bank. This may occur immediately upon birth, i.e. the human infant never receives its mother's fresh breast milk, or very soon thereafter such as within the first, second, third, fourth, fifth or sixth day of birth. In other embodiments, the human infant may cease to be fed its mother's fresh milk within about one week, two weeks or three weeks of birth, or within about one month, two month, three month or up to 6 months of birth.

The recombinant human bile-salt-stimulated lipase may be enterally administered according to the present invention by various means, including oral administration. For example, the administration may be performed using a paste, syrup, electuary, bolus, powder, granules, elixir, suspension, solution or other liquid form of the lipase. Oral administration may include buccal and sublingual administration of the lipase. Other forms of enteral administration may include methods that directly administer the lipase to the gastrointestinal tract, such as administering directly to the stomach by use of a gastric feeding or gastrostomy tube or placed into the small intestine using a duodenal feeding tube. For especially small, preterm or week infants such tube-based forms of administration may be more practical, or may be necessary, to administer the recombinant human bile-salt-stimulated lipase according to the instant invention.

Depending on the particular method of enteral administration, the formulation in which the recombinant human bile-salt-stimulated lipase is administered may differ. Liquid dosage forms for enteral administration of rhBSSL include pharmaceutically acceptable emulsions, microemulsions, solutions, suspensions, syrups and elixirs. In addition to the rhBSSL, the liquid dosage forms may contain inert diluents commonly used in the art, such as, for example, water or other solvents, solubilizing agents and emulsifiers, and mixtures thereof. Besides inert diluents, the compositions for enteral administration can also include additives such as wetting agents, emulsifying and suspending bulking agents and stabilizers. Suspensions, in addition to the active inhibitor(s) of the present invention, may contain suspending agents.

Whilst the most suitable means and formulation for enteral administration to a human infant for any specific circumstance may differ, a particularly suitable means of administration of the recombinant human bile-salt-stimulated lipase is to administer said lipase as part of the regular feed to said human infant, either orally or by tube-feeding. Accordingly, in a particular embodiment of the present invention the recombinant human bile-salt-stimulated lipase is first added to infant formula or to non-fresh (such as [previously] pasteurized) breast milk which is then fed to said infant. Feeding of this modified infant formula or modified non-fresh breast milk to the infant thereby provides enteral administration of said lipase. This means of administration is of particular relevance as it provides that the lipids comprised in the milk-based feed are present at the same time and location in the gastrointestinal tract as the (co)administered rhBSSL. In a certain particular embodiment of the invention, the recombinant human bile-salt-stimulated lipase is (co)administered with infant formula, such as by being first added to the formula before feeding said infant. The infant formula may have a composition analogous or substantially similar to one disclosed elsewhere herein.

As will be understood by the person of ordinary skill, the infant formula or (previously) pasteurized breast milk modified by the addition of recombinant human bile-salt-stimulated lipase will be commonly fed to said infant by use of a feeding bottle fitted with an appropriate teat or nipple to simulate the natural nipple and hence provide more effective feeding. Alternatively, the modified infant formula or modified non-fresh breast milk may be fed using other means; for example, by use of a dropper, syringe, spoon or a soaked-cloth, such as may be required if the infant has a deformity of the mouth. In certain embodiments, such as with extremely underweight, preterm or weak infants, the feeding may be made directly to the gastrointestinal tract via a gastric, gastrostomy, or duodenal tube.

In certain embodiments of the present invention, the non-fresh breast milk to which the recombinant human bile-salt-stimulated lipase is added is pasteurized breast milk. In other embodiments the breast milk has been frozen, such as after pasteurization. In particular embodiments, the breast milk used in the instant invention has come from a breast milk bank. Breast milk banks may include the National Milk Bank (NMB), a nationwide organization that collects donated human milk, ensures milk safety and quality and makes it available for infants in need, or the Human Milk Banking Association of North America (HMBANA), a non-profit association of donor human milk banks established in 1985 to set standards for and to facilitate establishment and operation of milk banks in North America.

As will be appreciated by the person of ordinary skill, it is particularly suitable that the breast milk used in the present invention is human breast milk. However, in alternative embodiments, particularly with older infants, the breast milk is obtained from a domesticated large animal such as a cow, sheep, goat or horse. Such embodiments may be practiced in certain cultures or countries that do not always feed human milk or infant formula, but may feed a human infant (at least partially) with milk obtained from such an animal. Such milks may not include sufficient animal BSSL to aid lipase digestion in a human infant—and certainly will not contain human BSSL—regardless of whether the milk has been pasteurized. Accordingly, the breast milk, when used in such an embodiment of the invention, may comprise fresh animal breast milk, i.e. milk that has not been heat-treated and/or frozen.

In yet another alternative embodiment, the recombinant human bile-salt-stimulated lipase is added to an infant formula. The skilled person will be aware of the many infant formulae that are commercially available, which include: Enfamil™, Pregestimil™, Nutramigen™, and Nutramigen AA™ (all marketed or made by Mead Johnson); Similac™, Isomil™, Alimentum™, and EleCare™ (all marketed or made by Abbott Laboratories, Ross division); Nestlé: 12%, the largest producer of formula in the world, makes Good-Start™ (marketed or made by Nestle/Gerber Products Company); Farex1™ and Farex2™ (marketed or made by Wockhardt Nutrition). For preterm infants, other infant formulae such as Similac Neosure, Entramil Premature, Similac Special Care, Cow & Gate Nutriprem 2 and Entramil Enfacare are also available Common to all infant formula is that they contain a source of lipids that are the substrates to lipases such as rhBSSL. In a particular embodiment, the infant formula has the composition (before addition of rhBSSL) generally in conformance with, or substantially as the specifications shown in Exhibit A, or as one recommended by the ESPGHAN Coordinated International Expert Group (Koletzko et al, 2005; J Ped Gastro Nutr 41: 584-599). In certain embodiments, the infant formula contains one or more of the ingredients, and at approximately the levels, shown in Exhibit B. In particularly advantageous embodiments, the infant formula contains at least 0.5% (of total fat) that is DHA and/or AA, and in further such embodiments where the concentration of AA should reach at least the concentration of DHA, and/or if eicosapentaenonic acid (C20:5 n-3) is added its concentration does not exceed the content of DHA.

For particular reasons, such as for convenience, safety and efficient distribution, the recombinant human bile-salt-stimulated lipase may be added to a bulk amount of (non-fresh) breast milk in a central location (such as at a milk bank) and then stored and/or distributed to infants. Analogously, the rhBSSL may be added to a bulk amount of infant formula at a central location, such as by a manufacturer of an infant formula, and then packaged and distributed (for example by being sold) to parents or care-providers of the human infants. This particular embodiment has particular utility when the modified formula (Including rhBSSL) can be stored and shipped as a dry powder. Alternatively, and particularly should an infant-specific dose be desired, the recombinant human bile-salt-stimulated lipase may be added to the infant formula or breast milk shortly before feeding and in amounts sufficient for such feeding, or in a ratio and amounts specific to that particular infant. For example, an appropriate amount of rhBSSL may be added to a feed-sized quantity of non-fresh breast milk or to infant formula.

A suitable ratio between the amounts of recombinant human bile-salt-stimulated lipase and the other components in the infant feed for the present invention lies wherein said lipase is added to infant formula or (previously) pasteurized and/or frozen breast milk to a final concentration of between about 0.03 and 0.5 g/L formula or milk. For example, said lipase may be added to infant formula or non-fresh breast milk to a final concentration of between about 0.05 and 0.3 g/L formula or milk. In particular embodiments the recombinant human bile-salt-stimulated lipase is added to a final concentration of between about 0.1 and 0.2 g/L formula or milk, such as around 0.15 g/L formula or milk. As will be appreciated from the description of certain earlier embodiments, suitable (absolute) concentrations may be adapted to provide a given concentration of active rhBSSL (suitable amounts being within those ranges given above), and/or such concentrations may alternatively be expressed in terms of the (active) molar (or micro mole) amounts of rhBSSL per unit volume of milk, such as the resulting molarity (M) of the rhBSSL in said milk, or in terms of the enzyme activity (U) per unit volume of milk (e.g. U/mL). In particular embodiments of the invention, the rhBSSL is administered as between about 15 and 300 units, between about 50 and 150 units rhBSSL per mL infant formula or milk (U/mL), between about 80 and 90 or about 87 U/mL infant formula or milk.

In particular embodiments of the present invention, the human infant is an underweight human infant. The human infant may be underweight upon birth, such as a Low Birth Weight (LBW) infant born weighing less than 2,500 g, a Very Low Birth Weight (VLBW) infant born weighing less than 1,500 g or an Extremely Low Birth Weight (ELBW) babies, born at less than 1000 g. Alternatively, the underweight infant may have a low birth mass (one that is below the average birth weight for a given gestational age) or is small for gestational age (SGA) (mass is below the 10th percentile of birth weight for a given gestational age). Alternatively, the infant may be underweight as it is not growing at a typical rate, such as an infant that is failing to thrive (FTT).

There are various possible causes for an infant to be (born) underweight. In particular, an infant is often underweight because it is born preterm. While not all preterm infants are underweight, preterm infants do have not fully developed their pancreas and liver functions, and can often not thrive as well as full-term babies. Accordingly, in another particular embodiment of the present invention, said human infant is a preterm human infant, i.e. one that is born before the normal pregnancy duration of about 40 weeks, or in particular is one born before about week 37 of gestation. In certain such embodiments, said preterm human infant is one born between about week 37 and about week 32 of gestation. In particular such embodiments, said preterm human infant is one born between about week 32 and about week 25 of gestation, or one born between about week 25 and about week 22 or gestation. In other particular such embodiments, said preterm infant is one born before about week 37 but after about week 21, week 22 or week 23, of gestation.

As will be appreciated by the person ordinarily skilled in the art, gestational age is commonly calculated by starting to count from the first day of the mother's last menstrual period (LMP), although in certain circumstances, such as in-vitro fertilization, gestational age can be calculated from the date of conception using a method known as fertilization age, embryonic age, conceptional age or intrauterine developmental (IUD) age. This method makes an infant appear about 2 weeks younger than if gestation was calculated by the more common LMP method.

In particular embodiments of the present invention said human infant is between 0 and 200 days of postpartum age. For example, the first administration of the recombinant human bile-salt-stimulated lipase may be made upon the day or birth, within one, two, three, four, five or six days of birth, or up to about the sixth month after birth. In certain such embodiments said human infant is less than four weeks of age, such as less than about three, two or one week of postpartum age upon first administration of recombinant human bile-salt-stimulated lipase according to the present invention. In other such embodiments, said human infant is between about one and two months or age, or is between about two and four months of age, such as about five months of age, upon first administration of recombinant human bile-salt-stimulated lipase according to the present invention.

Once first administered, in certain embodiments of the instant invention the recombinant human bile-salt-stimulated lipase is administered at least once per day (for example with at least one feed) for more than one day. For example, rhBSSL may be administered at least once per day according to the instant invention for a duration lasting at least about 4 days. In certain such embodiments, the recombinant human bile-salt-stimulated lipase is administered at least once per day (such as with at least one feed), for at least around 5 days, such as for a duration lasting at least around 7 days. In particular such embodiments, the recombinant human bile-salt-stimulated lipase is administered with (or as part of) most feeds given to said infant in any given day, for example between about 4 or 12 feeds per day, such as between about 5 and 10 feeds per day such as about 6, 7 or 8 feeds per day. In another non-limiting embodiment, the infant may be sometimes fed (such as once, twice or three-times per day) without (co)administration of the recombinant human bile-salt-stimulated lipase. In alternative such embodiments, the infant is (co)administered recombinant human bile-salt-stimulated lipase with every feed given to said infant; i.e., the infant is administered the rhBSSL for all feeds per day.

In certain embodiments the administration regimen for recombinant human bile-salt-stimulated lipase lasts for a period of time that is at least about one or two weeks. In particular such embodiments this duration is at least around 3 weeks, such as at least about 4 weeks. In alternative embodiments of the present invention, the recombinant human bile-salt-stimulated lipase is administered, such as part of a course of medical therapy, until the human infant is transferred out of intensive care, until discharged from hospital, until no longer under medical care or supervision or until said infant has absorbed a medically acceptable amount of the unsaturated fatty acid(s), such as AA and/or DHA.

In certain embodiments of the present invention, the increase in the absorption of at least one unsaturated fatty acid is concomitant with an increase in the growth velocity of said infant. As will be appreciated by the person of ordinary skill, growth of a human infant may be monitored by any common or acceptable method in order to investigate, monitor, follow and/or check for an increase, or otherwise an improvement or enhancement, of growth velocity. For example, the growth velocity of a human infant is, or may be monitored, for the purposes of the present invention by regular measurement and recording (such as daily) of head circumference, body mass (weight), body-length or leg length (such as knee-to-heel length). Other methods of measuring size and/or growth of a human infant are generally known. Such regular measurements can readily be converted to growth velocity; i.e. an amount of growth in a unit period (such as per day). In certain embodiments of the present invention, said increase in growth velocity of the human infant is, or is measured as (or otherwise monitored as), an increase in the rate of weight gain of said infant, such as a growth rate expressed as grams per day, a growth rate expressed as grams per Kg body weight per day (g/Kg/day), a growth rate expressed as grams per day per 100 Kcal energy consumed (g/day/100 kcal), or a growth rate expressed as grams per day per 100 mL milk/formula consumed (g/day/100 mL). Measuring body mass (weight) is a particular convenient method to monitor growth of an infant, and such second method of expressing growth rate (g/Kg/day) has particular utility as it seeks to normalize the absolute growth rate for different sized infants, as larger infants typically increase in weight by a larger absolute amount than smaller infants over the same period. Accordingly, in certain such embodiments, upon practice of the present invention the rate of weight gain achieved by, observed in or desired from said human infant when administered rhBSSL is between about 10 and 30 g increase in weight per Kg body weight of said infant per day (g/Kg/day). In particular such embodiments such rate of weight gain is between about 15 and 25 g/Kg/day, such as about 20 g/Kg/day or about 18 g/Kg/day.

In other embodiments of the present invention, the increase in growth velocity in the human infant administered recombinant human bile-salt-stimulated lipase is a weight gain that is between 1 g/Kg/day and 8 g/Kg/day, such as about 2, 3, 4 or 5 g/Kg/day greater than a human infant not administered rhBSSL. In an alternative embodiment of the invention, the increase in growth velocity is a weight gain that is between about 5% and 40% greater than the value of the growth velocity of a human infant not administered rhBSSL, such as between about 10% and 30% greater or 15% and 25% greater, including about 20% greater.

As will be appreciated, the weight of a human infant may fluctuate from day-to-day for various reasons, including those unrelated to administration of rhBSSL. Accordingly, the growth velocity stated herein as a per-day amount (or relative or percentage) may not be achieved by, observed in or desired from said human infant each and every day, and may only be so achieved by, observed in or desired from if measured and estimated over a number of days, such as over 3, 5 or 7 days, or for longer periods such as two, three or four weeks, or for example, over the period the infant during which the infant is being administered rhBSSL or receiving medical care such as within a NICU.

In other embodiments of the present invention, an increase in growth is measured (or otherwise monitored) as an increase in leg length; for example an increase in knee-to-heel length, as may be expressed as mm growth in a unit period, such as a week. In yet another embodiment, the growth velocity is monitored relative to its own size such as by use of the child's Weight-for-Height percentage (W/H %) or Standard Deviation (SD) score (also known as Z-score) which enables a child's growth to be monitored with reference to the Global Database on Child Growth and Malnutrition of the WHO.

As described elsewhere herein, the inventors observed that the present invention—as exemplified in two controlled clinical trials and an analysis of combined data from these two trials—resulted in an increase in the absorption, by human infants administered recombinant bile-salt-stimulated lipase, of groups, sub-groups and/or specific unsaturated fatty acids, as measured by the CFA (coefficient of fat absorption) for such group of, sub-group of and/or specific fatty acid(s). CFA can be monitored as described in the exemplification.

In certain embodiments of the present invention, the recombinant human bile-salt-stimulated lipase is administered prior to, after or concomitantly with at least one (other) food supplement and/or milk fortifier. Several such food supplements or milk fortifiers are approved, sold or otherwise used to help increase the growth of, or otherwise benefit, human infants and will be well known to the skilled person. By way of non-liming example, such food supplements and/or milk fortifiers include: Nutriprem, Milupa, Eoprotin, Enfamil Human Milk Fortifier and Similac Human Milk Fortifier In certain other embodiments of the present invention, the recombinant human bile-salt-stimulated lipase is administered prior to, after or concomitantly with at least one other lipase, such as another recombinant human lipase.

In alternative embodiments, the recombinant human bile-salt-stimulated lipase is administered without administration of additional food supplements and/or milk fortifiers (such as those described or defined herein), or without administration of any other lipase.

As will be appreciated, the relative ease at which the present invention may be practiced—in one embodiment administration merely by addition of the recombinant human bile-salt-stimulated lipase to an infant formula for oral feeding to the human infant—lends the invention to be practiced at the infant's home without medical intervention, supervision, support or advice. For example, the recombinant human bile-salt-stimulated lipase may be generally sold as a dietary supplement to aid the absorption of at least one unsaturated fatty acid(s) (such as AA and/or DHA) and/or aid the visual/cognitive development of babies. As a further non-limiting example, an infant formula may be manufactured and distributed for domestic use that already includes an appropriate amount of rhBSSL. Accordingly, in a certain aspect the invention relates to a non-medical method to increase the absorption by a human infant of at least one unsaturated fatty acid.

Alternatively, the present invention may be practiced, or instructed to be practiced, by qualified medical staff, or otherwise under or with medical intervention, supervision or advice, such as in a hospital or medical clinical, for example in an intensive care unit caring for preterm human infants. Accordingly, in such an alternative aspect of the present invention, the method relates to a medical method to increase the absorption by a human infant of and/or availability to at least one unsaturated fatty acid. In such aspect, the infant may be in medical need of at least one unsaturated fatty acid, and the amount of recombinant human bile-salt-stimulated lipase may be a therapeutically effective amount.

In a further aspect related to that above, the present invention therefore also relates to a therapeutic method to treat a human infant in need of at least one unsaturated fatty acid, said method comprising the step of enteral administration of recombinant human bile-salt-stimulated lipase to an infant in medical need thereof. Infants in particular need of such medical intervention may be premature infants, such as those before about week 37 of gestation, those small for gestational age (SGA), Low Birth Weight (LBW) infants and/or those suffering from a failure to thrive (FTT); in each case as may be described or defined elsewhere herein.

In another aspect, the present invention also relates to a method to improve the visual and/or cognitive development of a human infant, said method comprising the step of enteral administration of recombinant human bile-salt-stimulated lipase to said infant. In certain embodiments, this aspect is a non-medical method.

As will now be readily apparent to the person of ordinary skill, one or more of any of the embodiments described earlier—for example those describing the various recombinant human bile-salt-stimulated lipases, dosage amounts, administration modes and/or regimens, infant sub-populations, and also that administration with rhBSSL can result in an increase of absorption of at least one unsaturated fatty acid—may also further characterize this method to improve visual and/or cognitive development of a human infant. For example, such method to improve the visual and/or cognitive development of a human infant may use a rhBSSL isolated from an expression product of a recombinant hamster ovary cell, and/or may be administered in an amount per day of between 1 and 100 mg of said lipase per Kg weight of infant, such as administered in an infant formula to a preterm infant born before about week 37 of gestation.

In a related aspect of the present invention, the forgoing method (and any of its respective embodiments) is alternatively represented as: recombinant human bile-salt-stimulated lipase for use in improving the visual and/or cognitive development of a human infant, wherein said lipase is enterally administered. In another related aspect of the present invention, the forgoing method (and any of its respective embodiments) may be also represented as: a use of recombinant human bile-salt-stimulated lipase in the manufacture of a pharmaceutical composition for use in improving the visual and/or cognitive development of a human infant, wherein said lipase is enterally administered.

In certain embodiments of the present invention, the recombinant human bile-salt-stimulated lipase is provided in a form that is suitable for storage, distribution and/or incorporation into the modified infant formula or modified milk of the present invention. For example, in certain embodiments said lipase is provided as a lyophilized formulation. Typically, the lyophilized formulation of said lipase will be provided in a conveniently sized container such as in a vial, and may comprise an appropriate quantity of recombinant human bile-salt-stimulated lipase. In certain such embodiments the container is a sterile container, including being a sterile vial. When provided as a lyophilized formulation, the rhBSSL may be solubilized, such as with sterile water, prior to addition to the infant formula or milk, or alternatively the lyophilized formulation of rhBSSL may be solubilized directly in said infant formula or milk.

For convenience or other reasons, such as for sterility or safety, in certain embodiments of the present invention the recombinant human bile-salt-stimulated lipase is provided as a unit dose. A unit dose may provide sufficient (or slightly more) rhBSSL as is required for a single administration in a discrete unit or container. Alternatively, a small number of such discrete units or containers together, such as between 2 and 5 such discrete units or containers, provides sufficient (or slightly more) rhBSSL as is required for a single administration. In certain such embodiments, the unit dose form comprises an amount of recombinant human bile-salt-stimulated lipase that is between 1.5 and 75 mg lipase. In particular such embodiments the amount of rhBSSL is between 5 and 45 mg, or about 20 mg of said lipase.

In another embodiment, the recombinant human bile-salt-stimulated lipase is provided as a solution. The concentration of rhBSSL in such solution may be between 1.5 and 150 mg/mL, and in certain such embodiments may be at a concentration of between 7.5 and 30 mg/mL, such as at a concentration of about 15 mg/mL.

In particular embodiments of the present invention, the recombinant human bile-salt-stimulated lipase is provided as a composition or as a pharmaceutical formulation, such as a lyophilized or solution composition, that includes one or more pharmaceutically acceptable carriers as well as the rhBSSL. Suitable pharmaceutically acceptable carriers, if required, will be known the person of ordinary skill and include those described elsewhere herein.

In certain embodiments of the invention, a modified infant formula (containing rhBSSL) is already prepared for feeding. In other embodiments, said modified infant formula is subjected to processing before being fed to said infant. For example, the formula may be dissolved in water and/or warmed to an appropriate temperature for feeding such as 37° C. In particular such embodiments the modified infant formula is provided as a power or granules, or as a ready-to-use liquid or as a concentrated suspension or solution.

In certain embodiments of the invention, a modified breast milk (containing rhBSSL) is already prepared for feeding. In other embodiments, the modified breast milk is subjected to processing before being fed to said infant. For example, the modified breast milk may be thawed from a frozen state and/or warmed to an appropriate temperature for feeding such as 37° C.

A particularly practical aspect of the instant invention relates to a kit for the preparation of a modified infant formula or modified breast milk for use in: (a) increasing the absorption by a human infant of at least one unsaturated fatty acid; and/or for use in (b) improving the visual and/or cognitive development of a human infant; said kit comprising the components:
  a. at least one first container that includes a first amount of recombinant human bile-salt-stimulated lipase, such as in a lyophilized or solution formulation; and
  b. at least one second container, which is distinct from the first container, that includes a second amount of unmodified infant formula or unmodified pasteurized and/or frozen breast milk,
where said lipase and said unmodified infant formula, or unmodified pasteurized breast milk, are each in an amount sufficient to prepare a modified infant formula or modified pasteurized breast milk, respectively, that includes an amount of said lipase effective to: (a) increase the absorption of said unsaturated fatty acid by said infant; and/or to (b) improve the visual and/or cognitive development of said infant; when said modified infant formula or modified pasteurized breast milk is fed to said infant, such as is fed to said infant for at least one feed per day over at least around 4 days, for at least one feed per day over at least around 5 days, or for at least one feed per day over at least around 7 days;

In certain embodiments, the kit further comprises instructions. Such instructions may describe: (A) that said infant is in need of, or shall be in need of: (a) at least one unsaturated fatty acid; and/or in need of (b) improvement of visual and/or cognitive development. In alternative such embodiments, the instructions may describe: (B) that recombinant human bile-salt-stimulated lipase has been shown to be efficacious and safe in a clinical trial and to increase the absorption by a human infant (or otherwise increase the availability to a human infant) of at least one unsaturated fatty acid, such as the fatty acids AA and/or DHA.

In further certain embodiments of the present invention, the instructions in the kit may describe the steps of:
  i. preparing a modified infant formula or modified pasteurized breast milk that includes an amount of recombinant human bile-salt-stimulated lipase, such as by adding an amount of said lipase to an unmodified infant formula or unmodified pasteurized breast milk so as to form a modified infant formula or modified pasteurized breast milk, respectively; and
  ii. feeding said modified infant formula or modified pasteurized breast milk to a human infant for at least one feed per day over an administration regimen as described or defined herein.

In another aspect, the instant invention relates to a method to: (a) increase the absorption by a human infant of at least one unsaturated fatty acid; and/or to (b) improve the visual and/or cognitive development a human infant; said method comprising the steps of:
  i. preparing or otherwise providing a modified infant formula or a modified pasteurized breast milk in each case comprising rhBSSL or as prepared by the method or by using the kit above;
  ii. feeding the modified infant formula or modified pasteurized breast milk so prepared or otherwise provided to said infant; and
  iii. repeating the preceding steps over an administration regimen as described or defined herein.

Of particular utility for the medical or therapeutic applications provided herein by the present invention is a yet further aspect that relates to a packaged-pharmaceutical-product comprising a pharmaceutical composition that includes an amount of recombinant human bile-salt-stimulated lipase, wherein said packaged-pharmaceutical-product further comprises instructions that describe the steps of:
  i. preparing a modified infant formula or modified pasteurized breast milk that contains an amount of said lipase; and
  ii. enteral administration of said amount of lipase by feeding said modified infant formula or modified pasteurized breast milk to a human infant, such as for at least one feed per day over an administration regimen as described or defined herein;
  wherein said instructions describe that said: (A) infant is in need of, or shall be in need of: (a) at least one unsaturated fatty acid; and/or in need of (b) improvement of visual and/or cognitive development; and/or wherein said instructions describe: (B) that recombinant human bile-salt-stimulated lipase has been shown to be efficacious and safe in a clinical trial and to increase the absorption by a human infant (or otherwise increase the availability to a human infant) of at least one unsaturated fatty acid, such as the fatty acids AA and/or DHA.

In other embodiments of the present invention, the packaged-pharmaceutical-product further comprises an infant formula or pasteurized breast milk. Said infant formula or pasteurized breast milk may be included in the packaged-pharmaceutical-product as a separate component to the recombinant human bile-salt-stimulated lipase; i.e. it may be an unmodified infant formula or unmodified pasteurized breast milk. In an alternative such embodiment, the packaged-pharmaceutical-product may include the infant formula or pasteurized breast milk already comprising the recombinant human bile-salt-stimulated lipase; i.e. it may be a modified infant formula or unmodified pasteurized breast milk. In either of such embodiments, the infant formula may be provided as dried granulate or powder for solubilizing, or may be provided as a liquid (either at an appropriate concentration or as a concentrate) in a suitable container or as a frozen sample.

In certain embodiments of this packaged-pharmaceutical-product, the pharmaceutical composition is one described or defined elsewhere herein.

In yet further embodiments of the present invention, the pharmaceutical composition in the packaged-pharmaceutical-product comprises a unit dose that includes between 0.1 and 100 mg of recombinant human bile-salt-stimulated lipase. A unit dose will be readily understood by the person skilled in the art, and includes for example, those described or defined elsewhere herein. In certain embodiments of such aspect, the unit dose includes between 1.5 and 75 mg of rhBSSL. In particular such embodiments, the unit dose includes between 5 and 45 mg of said rhBSSL, such as about 10, 15, 20 or 25 mg of said lipase.

As will be appreciated from the discussion on enzyme amounts above, in certain embodiments of the invention, the unit dose of recombinant human bile-salt-stimulated lipase may be expressed in various ways, including in terms of the absolute mass of rhBSSL, or in terms of the mass of active rhBSSL. Alternatively (or in addition), the amount of rhBSSL may be expressed in terms of units (U) of enzyme. Accordingly, in particular embodiments the unit dose includes an amount of between about 2,000 and 20,000 units of rhBSSL (U), between about 5,000 and about 15,000, such as between about 7,000 and 10,000 units of rhBSSL.

In a further aspect, the present invention also relates to recombinant human bile-salt-stimulated lipase for use in: (a) increasing the absorption by a human infant of at least one unsaturated fatty acid; and/or for use in (b) improving the visual and/or cognitive development of a human infant. In a related aspect for therapeutic purposes, the present invention also relates to a pharmaceutical composition comprising recombinant human bile-salt-stimulated lipase, said pharmaceutical composition for use in: (a) increasing the absorption by a human infant of at least one unsaturated fatty acid and/or for us in (b) improving the visual and/or cognitive development of a human infant.

As will now be readily apparent to the person of ordinary skill, one or more of any of the embodiments described earlier—for example those describing the various recombinant human bile-salt-stimulated lipases, dosage amounts, administration modes and/or regimens, infant sub-populations, and also that administration with rhBSSL can result in an increase of absorption of at least one unsaturated fatty acid—may also further characterize these aspects. For example, such aspects for: (a) increasing the absorption by a human infant of at least one unsaturated fatty acid; and/or for (b) improving the visual and/or cognitive development of a human infant; may use a rhBSSL isolated from an expression product of a recombinant hamster ovary cell, and/or may be administered in an amount per day of between 1 and 100 mg of said lipase per Kg weight of infant, such as administered in an infant formula to a preterm infant born before about week 37 of gestation.

In certain embodiments of such aspects the recombinant human bile-salt-stimulated lipase or the pharmaceutical composition of the invention is in a unit dose, such as one described above.

In certain embodiments, the recombinant human bile-salt-stimulated lipase or the pharmaceutical composition of the invention is adapted for enteral administration, and/or for administration to a human infant, such as wherein said unit dose is specifically adapted for enteral administration to a human infant. For example, said unit dose is a lyophilized, solubilized or frozen amount of recombinant human bile-salt-stimulated lipase in an amount and/or formulation suitable for addition to or preparation as an infant formula or breast milk feed. In other embodiments, the unit dose may be provided in a form, container or amount of rhBSSL as described or defined elsewhere herein.

In particular embodiments of these aspects, the recombinant human bile-salt-stimulated lipase or the pharmaceutical composition of the invention is comprised in an infant formula or comprised in pasteurized breast milk.

As will now be appreciated by the person of ordinary skill, the recombinant human bile-salt-stimulated lipase that comprises the any of the kits or pharmaceutical compositions, or used in any of the methods, may be any of the recombinant human bile-salt-stimulated lipases described or defined elsewhere herein.

With regards to the present invention, in any of its methods requiring the preparation or provision of a modified infant formula or modified pasteurized breast milk, or its kits or packaged-pharmaceutical-product including instructions that describe such a preparation or provision, in certain embodiments of such aspects it may be required that and the recombinant human bile-salt-stimulated lipase and/or the unmodified infant formula or unmodified pasteurized breast milk is to be thawed and/or solubilized before the modified infant formula or modified pasteurized breast milk is prepared. Such preparation or provision may include that the recombinant human bile-salt-stimulated lipase is added to an unmodified infant formula (for example, provided as a dried-premix) or unmodified pasteurized frozen breast milk. In other embodiments, such preparation or provision may include that that a modified infant formula or modified pasteurized breast milk is first thawed and/or warmed to an appropriate temperature for feeding to a human infant, for example to 37° C. In other embodiments, an unmodified frozen breast milk is first thawed, the rhBSSL is then added, and then for example solubilized if said lipase is provides as in lyophilized power or granulate form.

As will be appreciated by the person of ordinary skill upon the disclosure of the present invention herein, the modified infant formula or modified pasteurized breast milk of the invention, or the kit, packaged-pharmaceutical-product, rhBSSL or pharmaceutical composition do not have to be in a quantity, size or amount to fulfill the needs of an entire treatment regimen. For example, a fresh quantity of modified infant formula or modified pasteurized breast milk may be prepared, such as from a kit, or pharmaceutical compositions of the present invention for each administration to the human infant, such that multiple kits or pharmaceutical compositions are utilized during the course of the treatment regimen.

It is to be understood that application of the teachings of the present invention to a specific problem or environment will be within the capabilities of one having ordinary skill in the art in light of the teachings contained herein. Examples of the products, compositions, packages or kits of the present invention and representative methods or processes for their preparation or use appear in the following.

All references, patents, and publications cited herein are hereby incorporated by reference in their entirety.

EXEMPLIFICATION

The following exemplification, including the experiments conducted and results achieved, also illustrate various presently particular embodiments of the present invention, and are provided for illustrative purposes only and are not to be construed as limiting the present invention.

Section 1: Drug Substance, its Characterization and Preparation of Investigational Drug Product.

The drug substance, human bile-salt-stimulated lipase, having a predicted amino acid sequence as shown in SEQ ID. NO. 1, was produced by expression from recombinant Chinese hamster ovary (CHO) cells containing a nucleic acid expression system comprising the nucleotide sequence encoding human BSSL according to standard procedures. Briefly, the 2.3 Kb cDNA sequence encoding full-length hBSSL including the leader sequence (as described by Nilsson et al, 1990; Eur J Biochem, 192: 543-550) was obtained from pS146 (Hansson et al, 1993; J Biol Chem, 268: 26692-26698) and cloned into the expression vector pAD-CMV 1 (Boehringer Ingelheim)—a pBR-based plasmid that includes CMV promoter/SV40 polyA signal for gene expression and the dhfr gene for selection/amplification—to form pAD-CMV-BSSL. pAD-CMV-BSSL was then used for transfection of DHFR-negative CHOss cells (Boehringer Ingelheim)—together with co-transfection of plasmid pBR3127SV/Neo pA coding for neomycin resistance to select for geneticin (G418) resistance—to generate DHFR-positive BSSL producing CHO cells. The resulting CHO cells were cultured under conditions and scale to express larger quantities of rhBSSL. For example, cells from the master cell bank (MCB) are thawed, expanded in shaker flasks using Ex-Cell 302 medium without glutamine and glucose (SAFC) later supplemented with glutamine and glucose, followed by growth in 15 and 100 L bioreactors, before inoculating the 700 L production bioreactor where BSSL is constitutively expressed and produced in a fed-batch process. The culture is harvested as a single batch and the mature rhBSSL polypeptide (i.e., without the leader sequence) is purified from cells, cell debris and other contaminates via a number of downstream steps, including an anion exchange chromatography step. Contaminating viruses may be inactivated by low pH treatment and a dry heat treatment step. The rhBSSL Drug Substance (DS) bulk is diafiltered and concentrated to the appropriate formulation. After formulation, the material is divided in one to three batches for lyophilization and heat treatment, generating one to three DS batches.

Production of rhBSSL in this mammalian-cell expression system produces rhBSSL having a predicted amino acid sequence as shown in SEQ ID. NO. 1 and a structure as schematically represented in FIG. 1.1, also marking the potential glycosylation sites.

This form of rhBSSL appears to exhibit glycosylation that is different to native hBSSL found in human milk (BSSL-MAM) and also to rhBSSL-OVI (produced from transgenic sheep). For example, using high pH anion exchange chromatography with pulsed amperiometric detection (HPAEC-PAD), the monosaccharide and sialic acid glycosylation level was determined for the CHO-derived rhBSSL produced and used for the clinical trials described herein (rhBSSL-CHO), and is found to have a total glycosylation level that is lower than BSSL-MAM, but higher than rhBSSL-OVI (see Table 1.1). These overall levels of glycosylation correlated to the overall molecular masses of each form of BSSL which, determined by MALDI-MS are found to be about 85 KDa for rhBSSL-CHO compared to 100 KDa and 78 KDa for BSSL-MAM and rhBSSL-OVI, respectively. As shown in Table 1.1, the pattern or profile of glycosylation (monosaccharide and sialic acid) on the possible glycosylation sites, particularly that of O-glycans, differs for rhBSSL-CHO compared to rhBSSL-MAM and to rhBSSL-OVI (detection using capillary electrophoresis with laser induced fluorescence detection [CE-LIF] and/or HPAEC-PAD).

TABLE 1.1

Monosaccharide and Sialic Acid content [mole/(mole BSSL)] for rhBSSL-CHO, rhBSSL-OVI and hBSSL-MAM

| | rhBSSL-CHO | hBSSL-MAM | rhBSSL-OVI |
|---|---|---|---|
| Monosaccharide content | | | |
| Fucose | 2.0 | 30.6 | 1.3 |
| Galactosamine | 16.6 | 15.8 | 3.0 |
| Glucosamine | 2.1 | 37.6 | 0.0* |
| Galactose | 17.5 | 51.8 | 3.4 |
| Glucose | 0.0 | 0.0 | 0.0 |
| Mannose | 5.0 | 9.8 | 2.5 |
| Total | 43.2 | 145.6 | 10.2** |

TABLE 1.1-continued

Monosaccharide and Sialic Acid content [mole/(mole BSSL)] for rhBSSL-CHO, rhBSSL-OVI and hBSSL-MAM

|  | rhBSSL-CHO | hBSSL-MAM | rhBSSL-OVI |
|---|---|---|---|
| Sialic acid content | | | |
| N-Acetyl neuraminic acid | 27.9 | 16.4 | 0.5 |
| N-Glycosyl neuraminic acid | 0.0 | 0.0 | 5.0 |
| Total | 27.9 | 16.4 | 5.5 |

*When analyzing for glucosamine in the rhBSSL-OVI material, a small peak in the chromatogram was seen. However no value was reported since such low amount was calculated as a negative value due to a greater intersection point of the calibration curve, which was subtracted. An estimated absolute/uncorrected value was 1.8 mole glucoseamine/mole BSSL.
**The total sum including (absolute/uncorrected) glucosamine was 12 mole/mole BSSL.

Not only is the degree and distribution of glycosylation for rhBSSL-CHO different to that of BSSL-MAM and to that of rhBSSL-OVI, but it is found that by C-terminal amino acid sequence (determined for example, by endoprotein Glu-C peptide mapping and sequence identification using liquid chromatography in combination with electrospray ionization mass spectrometry [LC-ESI-MS-MS]) that a large proportion of the lipase molecules are shortened by one (occasionally two) amino acids compared to the (predicted) full length polypeptide molecules. For every molecule with a full-length C-terminus sequenced, there are detected about three molecules having a C-terminus truncated by the last amino acid. A small proportion of C-terminal sequences are detected that were truncated by the last 2 amino acids. For example, of this population of (near full-length) lipase molecules, about 25% are full length, around 75% are shorter by one amino and less than 1% are shorter by two amino acids.

Differences in functional properties are observed between rhBSSL-CHO and BSSL-MAM and from rhBSSL-OVI. The specific activity of rhBSSL-CHO is observed to be higher than that of the other forms of BSSL. The specific activities of BSSL-MAM and rhBSSL-OVI are only 80% of that of rhBSSL-CHO based on mass. Each sample is specifically purified by HA-HPLC and SE-HPLC before determination of specific activity. Specific activity is determined using 4-nitrophenyl ester butyric acid (PNPB) as a substrate for BSSL, and detection of the release of 4-nitrophenol. Briefly, a dilution series of rhBSSL (for example, from 20 to 160 ng activity/mL) is prepared in PBS with 0.1% BSA. 200 µl of these rhBSSL solutions is added to 25 µl of an activation solution containing 20 mM sodium cholate (as bile-salt activator) in PBS with 0.1% BSA. These solutions are preincubated in a spectrophotometer at 27° C. for 5 minutes. Just before measuring, 25 µl of a well-mixed substrate solution containing 5 mM PNPB in PBS-Tween is added. The formation of 4-nitrophenol can be detected by its absorbance at 400 nm and the increase in absorbance is measured during 90 seconds. The active amount of BSSL is determined using a standard curve of an rhBSSL reference standard.

The investigational medicinal product was prepared from lyophilized Drug Substance that is dissolved in water for injection. The solution is pre-filtered (10 µm), and adjusted to the final (active) concentration with water for injection. The product is filtered through a 0.22 µm filter and filled into pre-sterilized 10 mL glass vials. The vials are stoppered with sterilized stoppers and sealed with aluminium caps.

Section 2: Abbreviated Report on Combined Data from Two Phase II Studies with rhBSSL
Protocol Number: BVT.BSSL-020
EUDRACT Number: 2007-002423-33
Clinicaltrials.gov identifier: NCT00658905
A prospective, randomized, double-blind crossover study comparing 0.15 g/L rhBSSL added to infant formula versus placebo during one week of treatment in preterm infants born before week 32 of gestational age And
Protocol Number: BVT.BSSL-021
EUDRACT Number: 2007-002434-10
Clinicaltrials.gov identifier: NCT00659243
A prospective, randomized, double-blind crossover study comparing 0.15 g/L rhBSSL added to pasteurized breast milk versus placebo during one week of treatment in preterm infants born before week 32 of gestational age

LIST OF ABBREVIATIONS

AA Arachidonic Acid
AE Adverse Event
ANCOVA Analysis of Covariance
ANOVA Analysis of Variance
BSSL Bile-salt-stimulated Lipase
CFA Coefficient of Fat Absorption
CRF Case Report Form
DHA Docosahexaenoic Acid
FA Fatty acid
FAS Full Analysis Set
g Gram
ICH International Conference on Harmonization
kg Kilogram
MedDRA Medical Dictionary for Regulatory Activities
mm Millimeter
N/A Not Applicable
PP Per-Protocol
PT Preferred Term
rhBSSL Recombinant human bile-salt-stimulated lipase
SAE Serious Adverse Event
SAP Statistical Analysis Plan
SAS® Statistical Analysis Software
SD Standard Deviation
SOC System Organ Class
TEAE Treatment-Emergent Adverse Event
TLFs Tables, Data Listings, and Figures

1 INTRODUCTION

Two phase II studies have been performed with rhBSSL in preterm infants, studies BVT.BSSL-020 and -021. The primary objective in both studies was to compare the fat absorption (coefficient of fat absorption, CFA) in preterm infants following treatment with rhBSSL to that with placebo when administered in formula (study-020) or pasteurized breast milk (study-021). Secondary objectives were to compare the length and body weight in preterm infants following treatment with rhBSSL to that in placebo when administered in infant formula/pasteurized breast milk, and to study the safety of rhBSSL when administered in infant formula pasteurized breast milk.

The sample size estimation in each study was based on an estimated 10% difference in CFA units between treatment periods and a standard deviation of 15%, with a power of 90% and a significance level of 5%. It was anticipated that a 10% difference in CFA would result in a 2 g/kg/day difference in growth velocity. However, none of the studies was expected to have a sufficient power to demonstrate an improvement in growth, due to the small number of patients (32) in each study and the short duration of treatment (1 week). Therefore, a pre-defined combined analysis of the two studies, with the primary objective to demonstrate improved growth following treatment with rhBSSL as compared to placebo when administered in infant formula or pasteurized breast milk was described in a separate statistical analysis plan (SAP). The SAP for the combined data was developed and finalized prior to database lock and unblinding of the clinical database in either of the two studies.

In addition, some post hoc analyses, not described in any SAP, have also been performed and are reported here.

The present report is a summary of the design and results from the two studies, focusing on the combined analysis but also in many cases presenting results by study. It is based on information given in the individual study reports, the statistical report of the combined analysis, and on a statistical report of the post hoc analysis.

Both studies were conducted according to ICH GCP guidelines and the Declaration of Helsinki. Both trials were approved by the appropriate Independent Ethics Committees and informed consent was signed by the guardians of all included patients.

2 ANALYSIS OBJECTIVES OF THE COMBINED ANALYSIS

2.1 Primary Objective

The primary objective of the combined analysis was to demonstrate improved growth following treatment with recombinant human bile-salt-stimulated lipase (rhBSSL) as compared to placebo when administered in infant formula or pasteurized breast milk.

2.2 Secondary Objectives

The secondary objectives were as follows:
To demonstrate improved fat absorption in preterm infants following treatment with rhBSSL as compared to placebo when administered in infant formula or pasteurized breast milk.
To compare the knee-to-heel length in preterm infants following treatment with rhBSSL to that in placebo when administered in infant formula or pasteurized breast milk.
To evaluate safety and tolerability of rhBSSL in preterm infants when administered in infant formula or pasteurized breast milk.

2.3 Exploratory Efficacy Objectives

The exploratory efficacy objectives were to explore the absorption of the long-chain polyunsaturated fatty acids (LCPUFAs) that were present in both formula and breast milk—docosahexaenoic Acid (DHA) and arachidonic acid (AA)—in preterm infants following treatment with rhBSSL to that with placebo when administered in infant formula or pasteurized breast milk.

3 STUDY DESIGN

The study designs and procedures of the two studies were the same with the exception of the feeding regimen (formula was used in study BVT.B SSL-020 and pasteurized milk in study BVT.B SSL-021), thus the combining of the data from the two studies is appropriate. Each study planned to enroll 32 patients in order to obtain 26 evaluable patients.

Patients were randomized to infant formula/pasteurized breast milk supplemented with rhBSSL at a final concentration of 0.15 g/L, or to infant formula/pasteurized breast milk "supplemented" with sterile water for injection (as placebo) for the first 7 days. After a washout period of 2 days, the patient was "crossed over" to the other treatment regimen during a second 7-day treatment period. Collection of feces samples for CFA assessment were performed during the last 3 days (72 hours) of each treatment period.

Patients were enrolled and randomized into these studies at the neonatal intensive care unit, after fulfilling all of the inclusion and none of the exclusion criteria. Infants who were receiving other infant formula prior to enrollment in the 020 study were to be switched from their current formula to the study formula on the day of enrollment. For patients in the 021 study who were receiving milk fortifiers other than Eoprotin, it was required to discontinue the milk fortification and/or switch to Eoprotin at least 2 days before the first dose.

The study design is presented in FIG. 2.1.

The schedule of study assessments is provided below in Table 2.1.

TABLE 2.1

Schedule of Study Assessments

| | 1* Screening | 2* Baseline | 3 | 4 | 5 | 6 | 7 | 8 | 9 WO Day | 10 WO | 11 | 12 | 13 | 14 | 15 | 16 | 17 | 18 F-Up |
|---|---|---|---|---|---|---|---|---|---|---|---|---|---|---|---|---|---|---|
| | −7 to −1 | 1 | 2 | 3 | 4 | 5 | 6 | 7 | 8 | 9 | 10 | 11 | 12 | 13 | 14 | 15 | 16[##] | 23 ± 3 |
| Informed consent | x | | | | | | | | | | | | | | | | | |
| Medical history | x | | | | | | | | | | | | | | | | | |
| Inclusion/Exclusion | x | | | | | | | | | | | | | | | | | |
| Demographic data | x | | | | | | | | | | | | | | | | | |
| Routine Laboratory, if available[#] | x[#] | x[#] | x[#] | x[#] | x[#] | x[#] | x[#] | x[#] | x[#] | x[#] | x[#] | x[#] | x[#] | x[#] | x[#] | x[#] | x[#] | x[#] |
| Physical examination | x | | | | | | | x | | x | | | | | | | x | x |
| Randomization | | x | | | | | | | | | | | | | | | | |
| Body weight (gram) | x | x | x | x | x | x | x | x | x | x | x | x | x | x | x | x | x | x |
| Growth-knee-to-heel (millimeter) | x | x | x | x | x | x | x | x | x | x | x | x | x | x | x | x | x | x |
| Body temperature | x | x | x | x | x | x | x | x | x | x | x | x | x | x | x | x | x[####] | x |
| Blood Pressure/Heart rate | x | x | x | x | x | x | x | x | x | x | x | x | x | x | x | x | x[####] | x |
| ECG, if available[#] | x[#] | x[#] | x[#] | x[#] | x[#] | x[#] | x[#] | x[#] | x[#] | x[#] | x[#] | x[#] | x[#] | x[#] | x[#] | x[#] | x[#] | x[#] |
| Check for nappy rash | | x | x | x | x | x | x | x | x | x | x | x | x | x | x | x | x | x |
| Concomitant medication | x | x | x | x | x | x | x | x | x | x | x | x | x | x | x | x | x | x |
| Administration of study drug | | x | x | x | x | x | x | x | | | x | x | x | x | x | x | x | |

TABLE 2.1-continued

Schedule of Study Assessments

| | Visit | | | | | | | | | | | | | | | | | |
|---|---|---|---|---|---|---|---|---|---|---|---|---|---|---|---|---|---|---|
| | 1*<br>Screening | 2*<br>Baseline | 3 | 4 | 5 | 6 | 7 | 8 | 9<br>WO<br>Day | 10<br>WO | 11 | 12 | 13 | 14 | 15 | 16 | 17 | 18<br>F-Up |
| | −7 to −1 | 1 | 2 | 3 | 4 | 5 | 6 | 7 | 8 | 9 | 10 | 11 | 12 | 13 | 14 | 15 | 16## | 23 ± 3 |
| Documentation of food intake | | x | x | x | x | x | x | x | | | x | x | x | x | x | x | x | |
| Weighing of vomiting | | | | | x | x | x | x | | | | | | x | x | x | x | |
| Tracer dye | | | | | x | | | x | | | | | | x | | | x | |
| Stool collection** | | | | | x | x | x | x | | | | | | x | x | x | x | |
| Tolerability assessments (stool consistency/color, regurgitation) | x | x | x | x | x | x | x | x | x | x | x | x | x | x | x | x | x | |
| Adverse Event | | x | x | x | x | x | x | x | x | x | x | x | x | x | x | x | x | x |

*Visit 1 and visit 2 could take place at the same time. All baseline assessments were to be performed and documented in the CRF prior to study drug administration
**Collection of stool began with the appearance of the first dye and continued until the second dye appeared. The stool containing the second marker was not collected.
***Study formula or milk intake continued until the second dye appeared in stool.
Only recorded when available within routine care. No extra blood samples or ECG taken for the study.
Visit 17 extended beyond Day 16 if necessary, until second tracer dye appears.
Vital signs collected daily until second dye appeared

4 PATIENT SELECTION

Patients selected for these studies were infants born before week 32 of gestational age and who were ≤32 weeks and 6 days of gestation (extrapolated age) at the time of enrollment. Infants enrolled in these studies did not receive parenteral nutrition (except glucose).

4.1 Inclusion Criteria

A patient must fulfill the following criteria in order to be included in the study:
1. Preterm infants born before week 32 of gestation and who were ≤32 weeks and 6 days of gestation (extrapolated age) at the time of enrollment
2. Preterm infants appropriate for gestational age (each site should use its own growth curves or procedures and keep a copy of those used in the investigator's file. The same growth curve should be used for all patients at one site)
3. Preterm infants receiving infant formula whose mothers are not intending to provide breast milk
4. Preterm infants receiving oral or enteral nutrition (bottle or nasal tube)

4.2 Exclusion Criteria

The presence of any of the following will exclude a patient from inclusion in the study:
1. Infants receiving parenteral nutrition (except glucose)
2. For BVT.BSSL-020: Infants receiving milk fortifiers (e.g., Enfamil, Nutriprem, Milupa Eoprotin®)
   Otherwise eligible infants who are receiving milk fortifiers may be enrolled if the use of fortifiers is discontinued 2 days before the first dose
   For BVT.BSSL-021: Infants receiving milk fortifiers other than Eoprotin® (e.g., Enfamil, Nutriprem).
   Otherwise eligible infants who received milk fortifiers than Eoprotin® could be enrolled if the use of fortifiers was discontinued 2 days before the first dose;
3. Infants requiring mechanical ventilation
4. Infants small for their gestational age (SGA)
5. Infants requiring ≥30% $O_2$
6. Infants receiving phototherapy (babies who have completed phototherapy and otherwise qualify for the study may be admitted)
7. Infants with severe brain disease including grade III or IV periventricular or intra ventricular hemorrhage, meningitis or hydrocephalus, intracranial hemorrhage of grade III or IV, periventricular leukomalacia
8. Major dysmorphology or congenital abnormalities that can affect growth and development
9. Infants with hemodynamically significant persistent ductus arteriosus (PDA)
10. Clinical evidence of sepsis (including low or high white cell count and/or low platelet count, and bacteriologically proven evidence of systemic infection)
11. Documented congenital infection (e.g. CMV)
12. Presence of necrotizing enterocolitis
13. Hemorrhagic pulmonary events
14. Prior or concomitant treatment with corticosteroids, except hydrocortisone
15. Any condition which in the opinion of the investigator makes the patient unsuitable for inclusion
16. Enrollment in another concurrent clinical study within 2 days of the screening visit through the completion of the follow-up visit

4.3 Removal of Subjects from Therapy or Assessment

A patient was to be withdrawn from the study drug if in the opinion of the investigator, it was medically necessary, or if it were the wish of the patient's parents or legal guardian. Other reasons for withdrawal from treatment could include the following:
  incorrect entry in the study
  major protocol violation
  adverse event

5 TREATMENTS

5.1 Treatments Administered

The amount of formula or milk given was based on the patient's body weight as recorded on the CRF each morning. The concentration of rhBSSL in the formula or pasteurized breast milk remained constant at 0.15 g/L. Patients received formula (study 020) or pasteurized breast milk (study 021) with or without rhBSSL for 7 days depending on the randomization schedule. A matching amount of sterile water for injection (WFI) was added to the pasteurized breast milk without rhBSSL when the patient was assigned to placebo. The amount of formula/milk given each day was recorded on the CRF.

| Treatment | Drug | Dosage Form | Route | rhBSSL dose in formula/milk | Feeding regimen |
|---|---|---|---|---|---|
| A BSSL | rhBSSL | Liquid solution | Oral | 0.15 g/L* | According to body weight* |
| B Placebo | Sterile water for injection | Liquid solution | Oral | Volume to match rhBSSL | According to body weight* |

*Infants were to receive approximately 150 to 180 mL milk/kg body weight per day. The feeding amount on a mL/kg basis for a particular infant was to remain constant for both treatment periods.

5.2 Identity of Investigational Product

Recombinant human BSSL drug substance and the investigational medicinal product (IMP) was prepared as described in Section 1 of the Exemplification (above).

Recombinant human BSSL was delivered as a frozen oral solution in a 10 mL glass vial. The strength was 15 mg/mL and the fill volume 1.3 mL. The study drug had to be stored frozen (−25° C. to −15° C.) at the study centre in a place inaccessible to unauthorized persons.

Before administration, the frozen solution was thawed and a 0.9 mL aliquot of the rhBSSL solution was transferred to 90 mL of formula (study 020) or pasteurized breast milk (study 021) to give a final concentration in the feed of 0.15 g/L. The placebo formula/milk was prepared in the same way, where 0.9 mL of sterile water was substituted for rhBSSL solution.

Two lots of IMP were used in both these studies.

The addition of the fortifier Eoprotin® as supplement was only allowed throughout study 021 (breast milk); however, the amount of Eoprotin® had to remain constant during the treatment phase.

5.3 Selection of Concentration

The concentration of rhBSSL to be added to pasteurized milk and formula has been selected based on the levels normally present in breast milk which is in the range of 0.1-0.2 g/L.

5.4 Blinding

The randomization schedules were maintained in a secure, locked location by Biovitrum's designee and were not revealed to any hospital personnel, investigators, Biovitrum personnel, or parents until after the database locks had been achieved. The addition of rhBSSL/placebo to formula or pasteurized breast milk was performed by a pharmacist or designee who was unblinded to the treatment assignment and was not involved in the evaluation of the patients.

5.5 Prior and Concomitant Therapy

Other therapy considered necessary for the patient's welfare could be given at the discretion of the Investigator. All such therapies were to be recorded on the CRF. The concomitant administration of parenteral nutrition (except glucose), milk fortifiers (with the exception of Eoprotin in study 021, as described above) within 2 days of the first dose of study medication through 2 days following the last dose, and corticosteroids, except hydrocortisone, was prohibited during the study. No other drug under investigation was to be used concomitantly with the study drug. The patients were not allowed to participate concurrently in another clinical study.

Preterm infants often experience complications that need therapeutic intervention. This was acceptable as long as the medication did not interfere with feeding. If concomitant medication resulted in the need for parenteral feeding, the patient was to be withdrawn from the study. Similarly, the development of complications that affect the absorption of enteral nutrition, such as necrotizing enterocolitis or abdominal obstruction, required that the patient discontinue participation in the study.

The use of ointments for the treatment of skin irritation was prohibited during the 72-hour fecal collection period. Diapers were to be changed frequently during the 72-hour collection period to keep the skin dry. Patients with skin rash severity leading to discontinuation of the stool collection were to be withdrawn from the study.

6 STUDY ASSESSMENTS FOR ANALYSIS ON COMBINED DATA

6.1 Efficacy Assessments in Each Study 6.1.1 Body Weight

The patient's weight in grams was recorded each day using a scale with an accuracy of at least +/−5 grams and entered on the CRF. To the extent possible, body weight was measured at approximately the same time each day.

6.1.2 Sample Collection

In study BVT.BSSL-021, aliquots of the breast milk were taken prior to addition of rhBSSL or placebo on Days 4-7 and Days 13-16.

The collection of feces for the determination of CFA was performed over a period corresponding to the fat, i.e., formula or milk, ingestion during 72 hours toward the end of each treatment period. Diapers supplied to each site were used for feces collection. During the two treatment periods, a carmine red tracer dye was given as a marker together with a meal (approximately at noon) on Day 4 and Day 13, respectively, and collection of stool commenced with the appearance of the first carmine red marker in the stool. The stool containing the first marker was collected and the date and time of the first stool collected was recorded on the CRF. At 72 hours following administration of the first red marker, the second carmine marker was given, and stool collection continued until the second carmine marker appeared. The stool containing the second marker was not collected, but the date and time of the appearance of the second marker was recorded on the CRF. Diapers were weighed before placement and after removal and the difference in weight was recorded on the CRF. The times of each collection and the elapsed duration of the entire collection period was also recorded on the CRF. The use of ointments for the treatment of skin irritation was prohibited during the stool collection period. Diapers were to be changed frequently during the collection period to keep the skin dry. Patients with skin rash severity leading to discontinuation of the stool collection were to be withdrawn from the study. Specific collection methods were provided in a separate laboratory manual. If applicable, vomit from the stool collection periods of both treatment periods was weighed. A small cloth/linen was weighed and placed under the head of each infant. When the cloth/linen was soiled with vomit, it was removed and re-weighed. If an additional cloth was used to remove vomit from the infant, that cloth was also weighed before and after use. The weight of vomit (total weight minus the weight of the cloth/linen) was recorded on the CRF. All other feed losses, e.g., formula or milk left in bottle, were measured and the amount accounted for in the calculation of the volume of formula consumed at each feeding.

All diapers and paper napkins used during each collection period were collected. They were placed in a sealed bag, labeled with patient ID and date and time and stored at −20° C. until shipment to the analytical laboratory.

6.1.3 Sample Analysis

Feces samples, the formula (study 020) and the milk aliquots (study 021) were analyzed by a central laboratory. Individual fatty acids, including the long-chain polyunsaturated fatty acids DHA and AA, were quantified in feces and feed by a gas chromatographic method following extraction by the Folch method. In both studies, the Omegawax 250 column (Supelco) was used for separation of the fatty acids. However, due to co-elution of DHA with nervonic acid (C24:1), which was only present in the breast milk, samples from patients of the per-protocol analysis set from study 021 were also analyzed using a SP-2380 column (Supelco) in order to quantify DHA for those samples from study 021. This column provides good separation of DHA and C24:1, but is less suitable for overall separation of other fatty acids in the formula and milk; hence individual fatty acids from these samples from study 021 (breast milk) were separated and analyzed using (separately) the SP-2380 column (for DHA) and the Omegawax 250 column (for all other fatty acids). Total lipids were calculated as the sum of the individual fatty acids. (See Section 7.5.1). The same analytical principle was used to determine lipids in each of the batches of formula and aliquots of breast milk used in the study.

6.1.4 Knee-to-Heel Length

The length of the patient's leg was measured from the knee to the heel using a knemometer provided to the sites. Knee-to-heel length was recorded in millimeters on the CRF. To the extent possible, length was measured at approximately the same time each day and by the same person. Three measurements were made and the mean value was entered on the CRF.

6.2 Safety Assessments: Adverse Events

The adverse event (AE) reporting period in each study began upon administration of the first dose (Day 1) of investigational medication and ended at the Follow-up Visit (1 week±3 days after the last dose of study drug intake). All AEs that occurred in a patient during the adverse event reporting period were to be reported, whether or not the event was considered medication/product related. In addition, any known untoward event that occurred subsequent to the AE reporting period that the investigator assessed as possibly, probably, or definitely related to the investigational product were also to be reported as an AE.

7 STATISTICAL METHODOLOGY 7.1 Analysis Populations

Safety Analysis Set: All randomized patients who received at least one dose of randomized study medication (rhB-SSL or placebo). The analysis of safety variables was performed using the safety analysis set.

Full Analysis Set (FAS): All randomized patients who received at least one dose of randomized study medication, and had a baseline and at least one post-baseline weight assessment in both treatment periods.

Per-Protocol Analysis Set (PP): All patients included in FAS who had reasonable compliance and no other major protocol violations.

The assessment of patients who qualified for the PP analysis set within each study was performed prior to database lock and unblinding of the respective study. For both FAS and PP, the combined datasets included exactly the same patients as in the individual studies.

7.2 Statistical Objective of the Combined Analysis 7.2.1 Primary Efficacy Objective and Hypothesis The primary objective of the analysis on the combined data from the two studies was to demonstrate improved growth following treatment with rhBSSL as compared to placebo when administered in infant formula or pasteurized breast milk.

The null hypothesis presupposed no difference between the treatments with respect to growth velocity.

The alternative hypothesis was as follows: rhBSSL improves growth velocity as compared to placebo when administered in infant formula or pasteurized breast milk.

7.2.2 Secondary Efficacy Objectives

The secondary efficacy objectives of the analysis on the combined data from the two studies were as follows:

To demonstrate improved fat absorption in preterm infants following treatment with rhBSSL as compared to placebo when administered in infant formula or pasteurized breast milk.

To compare the knee-to-heel length in preterm infants following treatment with rhBSSL to that in placebo when administered in infant formula or pasteurized breast milk.

With respect to CFA, the null hypothesis presupposed no difference between the treatments.

The alternative hypothesis was as follows: rhBSSL improves fat absorption as compared to placebo when administered in infant formula or pasteurized breast milk.

No statistical hypothesis test has been performed with respect to the knee-to-heel length.

7.2.3 Exploratory Efficacy Objectives

Exploratory efficacy objectives of the analysis on the combined data from the two studies were to explore the absorption of DHA and AA in preterm infants following treatment with rhBSSL to that with placebo when administered in infant formula or pasteurized breast milk.

7.2.4 Safety Objective

Safety objectives of the analysis on the combined data from the two studies were to evaluate safety and tolerability of rhBSSL in preterm infants when administered in infant formula or pasteurized breast milk.

7.3 Patient Disposition

Patient disposition was summarized by treatment sequence and was based on all patients randomized in both studies. The summary table included the number of patients randomized, the number (%) of patients who completed each study, the number (%) of patients who discontinued from each study, and the number (%) of patients for each reason for discontinuation. The summary table also reported the number (%) of patients included in the safety, FAS, and PP analysis sets, and the number (%) of patients who completed each treatment period.

7.4 Patient Demographic and Baseline Characteristics

Demographic characteristics included actual age and extrapolated gestational age on the day of first dose of study medication, gestational age at birth, gender, race, and ethnicity. Baseline characteristics included knee-to-heel length and body weight. Two summary tables were provided for demographic and baseline characteristics. The first table provided a summary of combined data by treatment sequence, and the second table provided summaries of demographic and baseline characteristics by study. Continuous variables were summarized by the number of patients, mean, standard deviation (SD), median, minimum, and maximum values. Categorical variables were summarized by the number and percentage of patients in each category.

7.5 Analysis of Efficacy

All efficacy data collected in these two studies were summarized for each study and for the combined analysis using descriptive statistics. Efficacy analyses for the individual trials were conducted in accordance with their efficacy objectives, as described in the Introduction (results of these analyses are not presented in this Report).

The primary analysis of the analysis on the combined data from the two studies was based on a 2-sided test using an alpha level of significance of 0.05. A stepwise sequential testing procedure was used to ensure a multiple level of significance of 0.05.

- $1^{st}$ step: The null hypothesis of no difference between the treatments with respect to growth velocity was tested using an alpha level of significance of 0.05. If the null hypothesis was rejected, then the $2^{nd}$ step of the sequential testing procedure was to be performed.
- $2^{nd}$ step: The null hypothesis of no difference between the treatments with respect to CFA was tested using an alpha level of significance of 0.05. If the null hypothesis was rejected, then a confirmatory claim was also to be made with respect to CFA.

This multiple comparison procedure controls that the multiple level of significance is no more than 5%.

Primary and secondary efficacy analyses and exploratory analyses reported point estimates and 95% confidence intervals around the estimates for each treatment and the estimated difference between treatments accompanied with the corresponding 95% confidence interval. No hypothesis testing was performed for variables other than growth velocity and CFA as stated above.

Continuous variables were summarized using n, mean, SD, median, minimum, and maximum values. Categorical variables were summarized using the number and percentage of patients in each category.

If a final assessment was not available when calculating the growth velocity during a period, the growth velocity was calculated at the last available assessment and carried forward to the final day. Otherwise, no imputation of missing data was performed.

7.5.1 Efficacy Variables for Analysis

The Primary Efficacy Variable was:
- Growth velocity (g/kg/day): Growth velocity was defined as, for the first period, (the weight at the last assessment in the first period minus the weight at Day 1) divided by [the weight at Day 1 and (the day of the last assessment in the first period minus 1)], and for the second period, (the weight at the last assessment in the second period minus the weight at Day 10) divided by [the weight at Day 10 and (the day of the last assessment in the second period minus 10)].

The Secondary Efficacy Variables were:
- CFA measured in food and feces samples collected between the tracer markers during the final 3 days (72 hours) of each treatment period.
- CFA was calculated as [Fat (g/period) in food—Fat (g/period) in stool]/[Fat (g/period) in food]*100.
- Fat in food was calculated as ([Food (mL)−Vomit (mL)]* [Fat Content in Food (g/100 mL)]/100. This formula was based on the following assumptions: (a) fat content in vomit is the same as the fat content in food; (b) density of vomit is the same as density of food.
- Fat content of food (formula or pasteurized breast milk) was determined using the same method as for the stool analysis and was performed by the same lab. Food (mL) and Vomit (mL) were calculated as the total amount of food or vomit recorded on or after the first tracer ingestion and prior to the second tracer ingestion. Vomit was recorded in grams on the CRF. Therefore, Vomit (mL) was calculated as Vomit (g)/Density.
- There was one difference in the calculation of fat (g/period) in stool and fat content in food (g/100 mL) between the two studies. That difference relates to different contents of fatty acids in milk and formula, as described below:

BVT.BSSL-020:
- Fat (g/period) in stool was calculated as a sum of the following fatty acids divided by 1000, since each fatty acid was provided in mg by the lab: C12:0, C14:0, C16:0, C18:0, C18:1, C18:2 n-6, C18:3 n-3, C20:4 n-6, and C22:6 n-3.
- Each fatty acid in food was provided in g/100 mL. Fat content in food (g/100 mL) was calculated as the sum of the same fatty acids as in the stool.

BVT.BSSL-021:
- Fat (g/period) in stool was calculated as a sum of the following fatty acids divided by 1000, since each fatty acid was provided in mg by the lab: C12:0, C14:0, C16:0, C16:1, C18:0, C18:1, C18:2 n-6, C18:3 n-3, C18:3 n-6, C20:1, C20:2 n-3, C20:3 n-6, C20:4 n-6, C22:6 n-3 and C24:1.
- Each fatty acid in food was provided in g/100 mL. Fat content in food (g/100 mL) was calculated as the sum of the same fatty acids as in the stool.

Combined Analysis:
- The combined statistical analysis of CFA data used the overall CFA values as calculated for each infant/treatment-period from each of the two individual studies.
- Change in length (mm): Change in length was defined as the change in length from knee to heel from Day 1 to Day 7 in the first period and Day 10 to Day 16 in the second period.

The Exploratory Efficacy Variables were:
- Absorption of DHA and AA: Coefficients of absorption of DHA (C22:6 n-3) and AA (C20:4 n-6) measured in feces samples collected during the final 3 days (72 hours) of each treatment period.
- Coefficients of absorption of DHA and AA were calculated using the same approach as used for CFA calculations, but using only the amounts of the individual (C22:6 n-3) and (C20:4 n-6) in samples for DHA and AA, respectively.

7.5.2 Efficacy Analysis Methodology

The primary and secondary efficacy analyses were based on the FAS of the combined data from the two studies. Supportive efficacy analyses were based on the PP analysis set of combined data from the two studies. In addition, analyses of each efficacy variable were provided by study for the FAS and for the PP analysis set.

The primary efficacy outcome, growth velocity, was analyzed by an analysis of variance (ANOVA) with treatment, regimen (pasteurized breast milk or infant formula), period, sequence, and patient nested within regimen and sequence as factors. All main effects were tested against the residual mean square from the ANOVA model.

The normality assumption of growth velocity distribution based on the combined data was tested using the Shapiro-Wilk test. If the normality assumption was not met, then the ranked values were to be used for the ANOVA.

The secondary efficacy outcome, CFA from the last three days of each treatment period, was analyzed in the same way as growth velocity by an analysis of variance (ANOVA) with treatment, regimen (pasteurized breast milk or infant formula), period, sequence, and patient nested within regimen and sequence as factors.

Descriptive statistics for the total amount of fat in food and the total amount of fat in stool were provided by treatment.

Another secondary efficacy outcome, change in knee-to-heel length, was analyzed by an analysis of covariance (ANCOVA) with treatment, regimen, period, sequence, and patient nested within regimen and sequence as factors using the baseline value as a covariate.

7.6 Analysis of Safety: Adverse Events

All adverse events (AE) analyses were based on the safety analysis set of the combined data from both studies. Results were presented using descriptive statistics. No hypothesis testing was performed.

MedDRA dictionary version 10.0 was used to classify all AEs reported during either study by system organ class (SOC) and preferred term (PT). All summary tables included counts of patients with treatment-emergent adverse events (TEAEs). The assessment of TEAEs was made in each individual study. TEAEs were defined as those AEs that either had an onset on or after the start of study drug and no more than 14 days (30 days for serious AEs) after the last dose of study drug, or were ongoing at the time of study drug initiation and increased in severity or became closer in relationship to study drug during the treatment period. All TEAEs, treatment related TEAEs (definite, probable, and possible), SAEs, and TEAEs leading to withdrawal of study drug were summarized by MedDRA SOC, PT, and treatment. Both the incidence (proportion of patients) and number of each TEAE were summarized. Additionally, TEAEs were summarized by maximum severity (mild, moderate, or severe). An overall summary of TEAEs was presented by treatment sequence and total and presented the number (%) of patients with TEAEs for each treatment sequence allocated to (1) BSSL only; (2) Placebo only; (3) Both BSSL and placebo; and (4) Neither Treatment.

7.7 Changes to the Analyses in the Statistical Analysis Plan

Because of the unexpected statistically significant effect of rhBSSL on the absorption of the two LCPUFAs, DHA and AA (see Section 8.4.3), despite no statistically significant effect on CFA for the sum of all measured fatty acids (see Section 8.4.2), a post hoc analysis of the coefficient of absorption of each individual fatty acid (FA), as well as analyses of the coefficient of absorption for the sum of all saturated FAs (all FAs, independent of chain length, with no double bonds), the sum of all unsaturated FAs (all FAs, independent of chain length, with at least one double bond), the sum of all polyunsaturated FAs (PUFAs, all FAs, independent of chain length, with at least two double bonds), and the sum of all LCPUFAs (all PUFAs with a chain length of at least 20 carbon atoms) were performed. Calculations were the same as for CFA for total fat. These analyses were not defined in the SAP. No correction for multiple comparisons has been performed, and p-values can only be considered to be descriptive.

8 RESULTS

8.1 Disposition of Patients

A summary of disposition of patients in the two studies by treatment sequence is shown in Table 2.2. Patient disposition by study was also collected and summarized (not shown in this Report).

TABLE 2.2

Patient Disposition

| | rhBSSL/Placebo | Placebo/rhBSSL | Total |
|---|---|---|---|
| Number of Patients Randomized | 32 | 33 | 65 |
| Safety Analysis Set[a] | 31 (100.0%) | 32 (100.0%) | 63 (100.0%) |
| Full Analysis Set (FAS)[b] | 30 (96.8%) | 30 (93.8%) | 60 (95.2%) |
| Per-Protocol Analysis Set (PP)[c] | 24 (77.4%) | 22 (68.8%) | 46 (73.0%) |
| Completed Period 1[d] | 30 (96.8%) | 31 (96.9%) | 61 (96.8%) |
| Completed Period 2[d] | 29 (93.5%) | 30 (93.8%) | 59 (93.7%) |
| Completed the study | 29 (93.5%) | 30 (93.8%) | 59 (93.7%) |
| Discontinued the Study | 2 (6.5%) | 2 (6.3%) | 4 (6.3%) |
| Adverse Event(s) | 2 (6.5%) | 2 (6.5%) | 4 (6.3%) |
| Protocol Violation(s) | 0 | 0 | 0 |
| Withdrew Consent | 0 | 0 | 0 |
| Lost to Follow-up | 0 | 0 | 0 |
| Sponsor's Request | 0 | 0 | 0 |
| Principal Investigator Decision | 0 | 0 | 0 |
| Other | 0 | 0 | 0 |

[a]The safety analysis set includes all patients who received at least one dose of randomized study medication.
[b]The full analysis set includes all randomized patients who received at least one dose of randomized study medication and had a baseline and at least one post-baseline weight assessment in both treatment periods.
[c]The per-protocol analysis set includes patients in the FAS who had reasonable compliance and no other major protocol violations.
[d]Completed period defined as patients who received study medication for 7 days in the treatment period.

A total of 65 patients were randomized across both studies: 33 patients in BVT.BSSL-020 and 32 patients in BVT.BSSL-021. A total of 63 patients received at least one dose of randomized study medication and were included in the safety analysis set: 33 patients in BVT.BSSL-020 and 30 in BVT-.BSSL-021. The FAS included a total of 60 patients who were in the safety analysis set and who had a baseline and at least one post-baseline weight assessment in both treatment periods: 33 patients in BVT.BSSL-020 and 27 patients in BVT.BSSL-021. A total of 46 patients were included in the PP analysis set: 26 patients in BVT.BSSL-020 and 20 patients in BVT.BSSL-021. There were 14 patients who were not included in the PP analysis set due to incomplete or incorrect stool collection.

Of the 63 patients in the safety analysis set, 31 patients were randomized to the rhBSSL/Placebo treatment sequence and 32 patients to Placebo/rhBSSL. A total of 61 patients completed Period 1, and a total of 59 patients completed Period 2. All but four patients completed the studies; these four patients discontinued due to AEs.

8.2 Demographic and Baseline Characteristics

Demographic and baseline characteristics for the combined data in the two studies by treatment sequence are shown below in Table 2.3. Demographic and baseline characteristics by study were also collected and summarized (not shown in this Report).

A difference in mean age on the day of first dose was also noticeable between the two studies: the mean age was lower for patients in BVT.BSSL-020 (3.39 weeks) compared to the mean age in BVT.BSSL-021 (4.39 weeks). Mean gestational age at birth was about one week higher in BVT.BSSL-020 (29.18 weeks) versus BVT.BSSL-021 (28.13 weeks). However, the gestational age on the day of first dose was similar in the two studies. A difference in ethnicity was also observed between the two studies: the percentage of Hispanic or Latino patients was higher in BVT.BSSL-020 (63.6%) compared to BVT.BSSL-021 (16.7%). Other demographic and baseline characteristics were comparable between the studies.

TABLE 2.3

Demographics and Baseline Characteristics

| Characteristic | rhBSSL/Placebo (N = 31) | Placebo/rhBSSL (N = 32) | Total (N = 63) |
|---|---|---|---|
| Age (Weeks)[a] | | | |
| N | 31 | 32 | 63 |
| Mean (SD) | 4.14 (1.553) | 3.60 (1.393) | 3.87 (1.487) |
| Gestational Age at Birth (Weeks) | | | |
| N | 31 | 32 | 63 |
| Mean (SD) | 28.39 (1.575) | 28.96 (1.542) | 28.68 (1.572) |
| Extrapolated Gestational Age (Weeks)[a] | | | |
| N | 31 | 32 | 63 |
| Mean (SD) | 32.53 (.447) | 32.58 (.541) | 32.56 (.494) |
| Gender | | | |
| Male | 15 (48.4%) | 18 (56.3%) | 33 (52.4%) |
| Female | 16 (51.6%) | 14 (43.8%) | 30 (47.6%) |
| Ethnicity | | | |
| Hispanic or Latino | 13 (41.9%) | 13 (40.6%) | 26 (41.3%) |
| Not Hispanic or Latino | 18 (58.1%) | 19 (59.4%) | 37 (58.7%) |
| Race | | | |
| White | 25 (80.6%) | 27 (84.4%) | 52 (82.5%) |
| Black | 1 (3.2%) | 2 (6.3%) | 3 (4.8%) |
| Asian | 1 (3.2%) | 1 (3.1%) | 2 (3.2%) |
| Native Hawaiian or Other Pacific Islander | 1 (3.2%) | 0 | 1 (1.6%) |
| Other | 3 (9.7%) | 2 (6.3%) | 5 (7.9%) |
| Knee-to-heel Length (mm)[b] | | | |
| N | 31 | 32 | 63 |
| Mean (SD) | 100.09 (5.490) | 99.78 (6.573) | 99.93 (6.017) |
| Weight (g) | | | |
| N | 31 | 32 | 63 |
| Mean (SD) | 1463.4 (169.28) | 1469.6 (216.25) | 1466.6 (193.02) |

[a]Age on the day of first dose.
[b]Measured with a knemometer.

In the combined analysis, the mean age on the day of first dose was higher for patients randomized to rhBSSL/Placebo (4.14 weeks) compared to the mean age for patients randomized to Placebo/rhBSSL (3.60 weeks). Other demographic and baseline characteristics were comparable between treatment sequences.

8.3 Treatment Compliance

Treatment compliance in study BVT.BSSL-020 is summarized below in Table 2.4 and for study BVT.BSSL-021 in Table 2.5.

TABLE 2.4

Treatment Compliance by Treatment Study BVT.BSSL.020

|  | Variable Statistics | |
|---|---|---|
|  | rhBSSL (N = 33) | Placebo (N = 33) |
| n | 33 | 33 |
| Treatment Compliance (%) | | |
| <60 | 0 | 0 |
| ≥60, <70 | 0 | 0 |
| ≥70, <80 | 0 | 1 (3.0%) |
| ≥80, <90 | 0 | 1 (3.0%) |
| ≥90, <100 | 28 (84.8%) | 25 (75.8%) |
| ≥100 | 5 (15.2%) | 6 (18.2%) |
| Mean | 98.79 | 97.24 |
| Std Dev | 1.639 | 4.967 |
| Median | 99.34 | 98.56 |
| Minimum | 92.6 | 73.0 |
| Maximum | 100.7 | 101.8 |

TABLE 2.5

Treatment Compliance by Treatment Study BVT.BSSL.021

|  | Variable Statistics | |
|---|---|---|
|  | rhBSSL (N = 28) | Placebo (N = 29) |
| n | 28 | 29 |
| Treatment Compliance (%) | | |
| <60 | 0 | 0 |
| ≥60, <70 | 1 (3.6%) | 0 |
| ≥70, <80 | 0 | 0 |
| ≥80, <90 | 2 (7.1%) | 1 (3.4%) |

TABLE 2.5-continued

Treatment Compliance by Treatment Study BVT.BSSL.021

|  | Variable Statistics | |
|---|---|---|
|  | rhBSSL (N = 28) | Placebo (N = 29) |
| ≥90, <100 | 16 (57.1%) | 19 (65.5%) |
| ≥100 | 9 (32.1%) | 9 (31.0%) |
| Mean | 95.97 | 97.52 |
| Std Dev | 7.033 | 3.820 |
| Median | 98.17 | 97.75 |
| Minimum | 66.7 | 87.2 |
| Maximum | 101.8 | 103.7 |

8.4 Efficacy Analysis 8.4.1 Primary Efficacy Variable

The primary efficacy variable in the combined analysis was the growth velocity. Combined results for growth velocity based on the combined analyses of the two clinical studies in the FAS and PP analysis sets are shown in Table 2.6. Growth velocity analysis results by study based on the FAS and PP analysis sets are shown in Tables 2.7a and 2.7b respectively.

TABLE 2.6

Analysis of Growth Velocity (g/kg/day) in the FAS and PP Analysis Sets

|  | Study Analysis Set and Statistics | | | |
|---|---|---|---|---|
|  | FAS Analysis Set | | PP Analysis Set | |
|  | rhBSSL (N = 60) | Placebo (N = 60) | rhBSSL (N = 46) | Placebo (N = 46) |
| N | 60 | 60 | 46 | 46 |
| Mean (SD) | 16.92 (4.540) | 14.00 (5.942) | 17.08 (4.424) | 15.04 (5.048) |
| Median | 16.84 | 14.95 | 16.84 | 15.09 |
| Minimum | 7.5 | −4.5 | 8.3 | 0.0 |
| Maximum | 26.5 | 26.4 | 26.5 | 26.4 |
| LS Mean | 16.86 | 13.93 | 17.15 | 15.06 |
| 95% CI | (15.73, 17.98) | (12.80, 15.05) | (15.92, 18.38) | (13.83, 16.29) |
| LS Mean Difference (rhBSSL − Placebo) | 2.93 | | 2.08 | |
| 95% CI of LS Mean Difference | (1.35, 4.51) | | (0.36, 3.81) | |
| p-value for LS Mean Difference | <0.001 | | 0.019 | |

The combined results of the two clinical studies showed a significant increase in growth velocity during rhBSSL treatment compared to during placebo treatment in both the FAS and PP analysis sets. In the FAS, the growth velocity LS means were 16.86 g/kg/day with rhBSSL and 13.93 g/kg/day with placebo. The difference in growth velocity between rhBSSL and placebo was statistically significant: LS mean difference (rhBSSL−Placebo) was 2.93 g/kg/day (p<0.001). In the PP analysis set, the LS mean difference (rhBSSL−Placebo) of 2.08 g/kg/day was also statistically significant (p=0.019).

Table 2.7a below displays the growth velocity results in the FAS analysis set for each of the two clinical studies, and Table 2.7b displays the same for the PP analysis set.

TABLE 2.7a

Analysis of Growth Velocity (g/kg/day) by Study in the FAS Analysis Set

| | Statistics | | | |
|---|---|---|---|---|
| | BVT.BSSL-020 | | BVT.BSSL-021 | |
| | rhBSSL (N = 33) | Placebo (N = 33) | rhBSSL (N = 27) | Placebo (N = 27) |
| N | 33 | 33 | 27 | 27 |
| Mean (SD) | 18.06 (3.964) | 14.29 (6.493) | 15.54 (4.880) | 13.63 (5.292) |
| Median | 18.39 | 15.51 | 15.95 | 13.98 |
| Minimum | 9.2 | −4.5 | 7.5 | −3.1 |
| Maximum | 25.5 | 23.3 | 26.5 | 26.4 |
| LS Mean | 18.05 | 14.31 | 15.58 | 13.63 |
| 95% CI | (16.52, 19.58) | (12.78, 15.84) | (13.82, 17.33) | (11.87, 15.39) |
| LS Mean Difference (rhBSSL − Placebo) | 3.74 | | 1.95 | |
| 95% CI of LS Mean Difference | (1.58, 5.90) | | (−0.54, 4.43) | |
| p-value for LS Mean Difference | 0.001 | | 0.119 | |

The improvement in growth velocity during rhBSSL treatment compared to placebo was more pronounced in study BVT.BSSL-020 than in study BVT.BSSL-021. Based on the FAS, in the BVT.BSSL-020 study, the LS mean difference (rhBSSL−Placebo) was 3.74 g/kg/day (p=0.001) whereas in the BVT.BSSL-021 study, it was 1.95 g/kg/day (p=0.119). Similar results by study were observed in the PP analysis set (see Table 2.7b).

Wilk test. The test for normality was significant in the FAS (p-value<0.001), indicating that the normality assumption was not met. (A similar result was seen for the PP analysis set.) Therefore, an analysis of growth velocity using the ranked values was also performed. The result of this sensitivity analysis was consistent with the primary analysis with a resulting p-value of <0.001, demonstrating a significant improvement in growth during rhBSSL treatment as compared to placebo.

TABLE 2.7b

Analysis of Growth Velocity (g/kg/day) by Study in the PP Analysis Set

| | Statistics | | | |
|---|---|---|---|---|
| | BVT.BSSL-020 | | BVT.BSSL-021 | |
| | rhBSSL (N = 26) | Placebo (N = 26) | rhBSSL (N = 20) | Placebo (N = 20) |
| N | 26 | 26 | 20 | 20 |
| Mean (SD) | 17.79 (4.013) | 15.39 (5.412) | 16.16 (4.856) | 14.59 (4.630) |
| Median | 17.98 | 16.08 | 16.80 | 14.95 |
| Minimum | 9.2 | 0.0 | 8.3 | 3.4 |
| Maximum | 24.0 | 23.3 | 26.5 | 24.6 |
| LS Mean | 17.75 | 15.45 | 16.47 | 14.76 |
| 95% CI | (16.22, 19.28) | (13.92, 16.98) | (14.23, 18.71) | (12.51, 17.00) |
| LS Mean Difference (rhBSSL − Placebo) | 2.30 | | 1.71 | |
| 95% CI of LS Mean Difference | (0.14, 4.47) | | (−1.46, 4.88) | |
| p-value for LS Mean Difference | 0.038 | | 0.271 | |

Another observation from Table 2.7a was that patients on formula gained weight more rapidly than patients on pasteurized breast milk. In the FAS, the mean growth velocity during rhBSSL treatment was 18.06 and 15.54 g/kg/day in BVT.BSSL-020 and BVT.BSSL-021 respectively, and during placebo treatment it was 14.29 and 13.63 g/kg/day in the respective studies. Similar results were observed in the PP analysis set (see Table 2.7b).

The normality assumption of growth velocity distribution based on the combined data was tested using the Shapiro- 8.4.2 Secondary Efficacy Variables The secondary efficacy variables were CFA, and change in knee-to-heel length between the start and end of each treatment period.

CFA: Only patients in the PP analysis set had complete/correct stool collection, essential for the determination of CFA. Therefore, the presentation in the present report is limited to data for the PP analysis set, with the exception of Table 2.8a below that shows CFA results of the combined analysis of the two clinical studies for both the FAS and the PP analysis set. The CFA analysis results by study based on the PP analysis sets are provided in Table 2.8b.

TABLE 2.8a

Analysis of CFA (%) in the FAS and PP Analysis Sets

| | Study Analysis Set and Statistics | | | |
|---|---|---|---|---|
| | FAS Analysis Set | | PP Analysis Set | |
| | rhBSSL (N = 60) | Placebo (N = 60) | rhBSSL (N = 46) | Placebo (N = 46) |
| N | 59* | 59* | 46 | 46 |
| Mean (SD) | 67.80 (16.663) | 64.06 (16.319) | 69.08 (14.683) | 65.66 (16.126) |
| Median | 71.09 | 66.50 | 71.83 | 67.15 |
| Minimum | 11.7 | 25.7 | 31.2 | 25.7 |
| Maximum | 93.2 | 93.0 | 93.2 | 93.0 |
| LS Mean | 7.78 | 4.08 | 9.06 | 5.50 |
| 95% CI | (64.73, 70.83) | (61.03, 67.13) | (66.31, 71.80) | (62.75, 68.25) |
| LS Mean Difference (rhBSSL – Placebo) | 3.70 | | 3.56 | |
| 95% CI of LS Mean Difference | (−0.60, 8.00) | | (−0.29, 7.40) | |
| p-value for LS Mean Difference | 0.090 | | 0.069 | |

*One patient in study 020 withdrawn before stool collection period.

The combined results of the two clinical studies showed a numerical increase in CFA in rhBSSL compared to placebo in both the FAS and PP analysis sets. In the PP analysis set, the LS mean CFA were 69.1% during rhBSSL treatment and 65.5% for placebo; the LS mean difference (rhBSSL–Placebo) was 3.56% (p=0.069).

The improvement in CFA during rhBSSL treatment compared to placebo was higher in BVT.BSSL-021 compared to BVT.BSSL-020. In the PP, the LS mean difference (rhBSSL–Placebo) was 4.86% (p=0.073) in BVT.BSSL-021 and 2.08% (p=0.462) in BVT.BSSL-020. Similar results were observed in the FAS analysis set by study (see Table 2.8b).

TABLE 2.8b

Analysis of CFA (%) by Study in the PP Analysis Set

| | Statistics | | | |
|---|---|---|---|---|
| | BVT.BSSL-020 | | BVT.BSSL-021 | |
| | rhBSSL (N = 26) | Placebo (N = 26) | rhBSSL (N = 20) | Placebo (N = 20) |
| N | 26 | 26 | 20 | 20 |
| Mean (SD) | 69.55 (14.452) | 67.07 (14.849) | 68.46 (15.333) | 63.82 (17.875) |
| Median | 70.99 | 67.15 | 75.41 | 67.09 |
| Minimum | 36.8 | 25.7 | 31.2 | 35.9 |
| Maximum | 89.0 | 93.0 | 93.2 | 91.3 |
| LS Mean | 69.46 | 67.38 | 68.56 | 63.70 |
| 95% CI | (65.40, 73.53) | (63.31, 71.45) | (64.78, 72.35) | (59.92, 67.49) |
| LS Mean Difference (rhBSSL – Placebo) | 2.08 | | 4.86 | |
| 95% CI of LS Mean Difference | (−3.67, 7.84) | | (−0.50, 10.22) | |
| p-value for LS Mean Difference | 0.462 | | 0.073 | |

Table 2.9a provides the total amount of fat in food consumed between food tracer markers and the total amount of fat in stool from stool samples collected between tracer markers in stools by study in the combined analysis (PP analysis set). Data by treatment for the combined analysis are provided in Table 2.9b.

TABLE 2.9a

Total Amount of Fat in Food and Total Amount of
Fat in Stool by Study in the PP Analysis Set.

|  | Statistics | | | |
| --- | --- | --- | --- | --- |
|  | BVT.BSSL-020 | | BVT.BSSL-021 | |
|  | rhBSSL (N = 26) | Placebo (N = 26) | rhBSSL (N = 20) | Placebo (N = 20) |
| Total Amount of Fat in Food (g) | | | | |
| N | 26 | 26 | 20 | 20 |
| Mean (SD) | 29.12 (5.037) | 28.50 (5.047) | 19.00 (5.110) | 20.51 (6.718) |
| Median | 29.11 | 27.98 | 18.27 | 18.70 |
| Minimum | 21.1 | 17.7 | 12.1 | 13.3 |
| Maximum | 44.0 | 39.3 | 29.1 | 43.7 |
| Total Amount of Fat in Stool (g) | | | | |
| N | 26 | 26 | 20 | 20 |
| Mean (SD) | 8.53 (3.416) | 8.97 (3.278) | 6.16 (3.550) | 7.56 (4.785) |
| Median | 8.63 | 9.06 | 4.99 | 6.09 |
| Minimum | 3.2 | 2.0 | 0.9 | 2.0 |
| Maximum | 15.0 | 14.7 | 13.3 | 18.0 |

Patients on formula consumed more fat from food than patients on pasteurized breast milk. In the PP, the mean total amount of fat in food consumed during rhBSSL treatment (72-hour collection period) was 29.12 g and 19.00 g in BVT-.BSSL-020 and BVT.BSSL-021 respectively, and during placebo treatment it was 28.50 g and 20.51 g in the respective studies. Patients on formula also excreted more fat in stool than patient on pasteurized breast milk. The mean total amount of fat excreted in stool during rhBSSL treatment was 8.53 g and 6.16 g in BVT.BSSL-020 and BVT.BSSL-021 respectively, and during placebo it was 8.97 g and 7.56 g in the respective studies.

Table 2.9b summarizes the total amount of fat in food and the total amount of fat in stool, during the 72-hour collection interval, for the combined results in the PP and analysis set. Fat intake and fat excretion were comparable for the two treatments. In the combined data from the two studies, in the PP, the mean amount of fat in food consumed during rhBSSL treatment was 24.72 g, and the mean amount consumed during placebo was 25.03 g. The amount of fat excreted in stool was 7.50 g and 8.36 g, respectively.

TABLE 2.9b

Total Amount of Fat in Food and Total Amount of Fat
in Stool, combined data, in the PP Analysis Set.

|  | Statistics PP Analysis Set | |
| --- | --- | --- |
|  | rhBSSL (N = 46) | rhBSSL (N = 46) |
| Total Amount of Fat in Food (g) | | |
| n | 46 | 46 |
| Mean (SD) | 24.72 (7.133) | 25.03 (7.018) |
| Median | 25.28 | 24.35 |
| Minimum | 12.1 | 13.3 |
| Maximum | 44.0 | 43.7 |
| Total Amount of Fat in Stool (g) | | |
| n | 46 | 46 |
| Mean (SD) | 7.50 (3.635) | 8.36 (4.018) |
| Median | 7.05 | 8.34 |

TABLE 2.9b-continued

Total Amount of Fat in Food and Total Amount of Fat
in Stool, combined data, in the PP Analysis Set.

|  | Statistics PP Analysis Set | |
| --- | --- | --- |
|  | rhBSSL (N = 46) | rhBSSL (N = 46) |
| Minimum | 0.9 | 2.0 |
| Maximum | 15.0 | 18.0 |

There was little difference between the mean volume of infant formula or breast milk ingested between the different studies, or the volume ingested between treatment periods with rhBSSL or with placebo.

Correlation Between Growth Velocity and Fat Absorption

FIG. 2.2 presents the difference in growth velocity (rhBSSL–placebo) vs. the difference in CFA (rhBSSL–placebo) in the combined analysis of data from the PP analysis sets from the two studies.

As seen in this graph, there was no statistically significant correlation (p-value 0.177) between the effect of rhBSSL on growth velocity and fat absorption (CFA).

Chante in Knee-to-Heel Length

The results of change in knee-to-heel length for the combined analysis from the two studies in the FAS and PP analysis were collected and summarized (not shown in this Report).

No noticeable differences were observed between treatments with respect to mean change in knee-to-heel length measurements in either the FAS or PP analysis sets in the combined data from both studies, or by study.

8.4.3 Exploratory Efficacy Variables

Just as for the presentation of CFA for total fat, the presentation of the exploratory efficacy variables is limited in this report to data for the PP analysis set, with the exception of Table 2.10. and Table 2.11. below that show results for both the FAS and the PP analysis set.

The exploratory efficacy variables were the coefficients of absorption of the two long-chain polyunsaturated fatty acids, docosahexaenoic acid (DHA, C22:6 n-3) and arachidonic acid (AA, C20:4, n-6), that were present in both formula and breast milk.

DHA: The results of DHA for the combined analysis from the two studies in the FAS and the PP analysis sets are shown in Table 2.10. The results of DHA by study in the PP analysis set were collected and are summarized in the applicable cells of Tables 2.13 and 2.14.

observed in the FAS analysis set from the combined analysis of the two studies. Noticeably higher coefficients of absorption of DHA and AA for rhBSSL compared to placebo were also observed in each study (see the applicable cells in Tables 2.13 and 2.14.

TABLE 2.10

Analysis of Coefficient of Absorption of DHA (%) in the FAS and PP Analysis Sets

| | Study Analysis Set and Statistics | | | |
|---|---|---|---|---|
| | FAS Analysis Set | | PP Analysis Set | |
| | rhBSSL (N = 60) | Placebo (N = 60) | rhBSSL (N = 46) | Placebo (N = 46) |
| N | 59 | 59 | 46 | 46 |
| Mean (SD) | 77.97 (16.251) | 71.70 (17.668) | 79.76 (14.075) | 74.00 (16.197) |
| Median | 81.22 | 71.69 | 82.90 | 73.35 |
| Minimum | 26.8 | 24.7 | 42.2 | 24.7 |
| Maximum | 100.0 | 98.3 | 100.0 | 98.3 |
| LS Mean | 77.91 | 71.67 | 79.83 | 74.03 |
| 95% CI | (74.55, 81.26) | (68.32, 75.03) | (76.62, 83.04) | (70.82, 77.24) |
| LS Mean Difference (rhBSSL − Placebo) | 6.24 | | 5.80 | |
| 95% CI of LS Mean Difference | (1.50, 10.97) | | (1.30, 10.29) | |
| p-value for LS Mean Difference | 0.011 | | 0.013 | |

AA: The results of AA for the combined analysis from the two studies in the FAS and PP analysis sets are shown in Table 2.11. The results of AA by study in the PP analysis set were collected and are summarized in the applicable cells of Tables 2.13 and 2.14.

TABLE 2.11

Analysis of Coefficient of Absorption of AA (%) in the FAS and PP Analysis Sets

| | Study Analysis Set and Statistics | | | |
|---|---|---|---|---|
| | FAS Analysis Set | | PP Analysis Set | |
| | rhBSSL (N = 60) | Placebo (N = 60) | rhBSSL (N = 46) | Placebo (N = 46) |
| N | 59 | 59 | 46 | 46 |
| Mean (SD) | 77.88 (17.628) | 69.16 (22.015) | 78.01 (16.881) | 69.42 (22.389) |
| Median | 81.28 | 71.29 | 81.01 | 70.92 |
| Minimum | 26.6 | −3.0 | 26.6 | −3.0 |
| Maximum | 100.0 | 97.8 | 100.0 | 97.8 |
| LS Mean | 77.60 | 68.90 | 77.36 | 68.73 |
| 95% CI | (73.98, 81.23) | (65.27, 72.52) | (73.76, 80.96) | (65.13, 72.32) |
| LS Mean Difference (rhBSSL − Placebo) | 8.70 | | 8.63 | |
| 95% CI of LS Mean Difference | (3.59, 13.82) | | (3.60, 13.67) | |
| p-value for LS Mean Difference | 0.001 | | 0.001 | |

The coefficients of absorption of both DHA and AA in the combined results from the two studies were noticeably higher for rhBSSL than for placebo. In the PP, the LS mean coefficient of absorption of DHA was 79.83% during rhBSSL treatment compared to 74.03% for placebo; the LS mean difference (rhBSSL−Placebo) was 5.80% (p=0.013). The LS mean coefficient of absorption of AA was 77.36% with rhBSSL and 68.73% with placebo; the LS mean difference (rhBSSL−Placebo) was 8.63% (p=0.001). Similar results were 8.4.4 Post Hoc Analyses Individual FAs: The results for the coefficient of absorption for each FA that was present in both formula and pasteurized milk were collected and summarized (Data for C20:4 [AA] and C22:6 [DHA] are presented in Section 8.4.3 above.). The results are summarized below in Table 2.12. The corresponding results are presented by study and summarized below in Table 2.13. (study 020) and Table 2.14 (study 021). Table 2.14 also contains data on the FAs that were only present in the milk and therefore not included in the combined analyses.

TABLE 2.12

CFA for individual fatty acids present in both formula and pasteurized breast milk. Combined analysis. Per-protocol Analysis Set.

| No. double bonds | | No. of carbon atoms | | | | | |
|---|---|---|---|---|---|---|---|
| | | 12 | 14 | 16 | 18 | 20 | 22 |
| 0 | rhBSSL | 88.86 | 76.15 | 55.49 | 44.28 | | |
| | Placebo | 86.44 | 71.34 | 52.88 | 42.76 | | |
| | Difference | 2.42 | 4.81* | 2.61 | 1.51 | | |
| | 95% CI | −0.21, 5.05 | 0.24, 9.38 | −2.15, 7.38 | −3.87, 6.90 | | |
| 1 | rhBSSL | | | | 73.66 | | |
| | Placebo | | | | 70.02 | | |
| | Difference | | | | 3.65 | | |
| | 95% CI | | | | −0.47, 7.76 | | |
| 2 n-6 | rhBSSL | | | | 77.49 | | |
| | Placebo | | | | 71.70 | | |
| | Difference | | | | 5.79* | | |
| | 95% CI | | | | 1.82, 9.76 | | |
| 3 n-3 | rhBSSL | | | | 76.31 | | |
| | Placebo | | | | 72.65 | | |
| | Difference | | | | 3.66 | | |
| | 95% CI | | | | −1.24, 8.55 | | |
| 4 n-6 | rhBSSL | | | | | 77.36 | |
| | Placebo | | | | | 68.73 | |
| | Difference | | | | | 8.63* | |
| | 95% CI | | | | | 3.60, 13.67 | |
| 6 n-3 | rhBSSL | | | | | | 79.83 |
| | Placebo | | | | | | 74.03 |
| | Difference | | | | | | 5.80* |
| | 95% CI | | | | | | 1.30, 10.29 |

*P < 0.05

TABLE 2.13

CFA for individual fatty acids, study BVT.BSSL-020 (infant formula). Per-protocol Analysis Set.

| No. double bonds | | No. of carbon atoms | | | | | |
|---|---|---|---|---|---|---|---|
| | | 12 | 14 | 16 | 18 | 20 | 22 |
| 0 | rhBSSL | 89.70 | 76.56 | 46.95 | 42.20 | | |
| | Placebo | 88.52 | 73.37 | 46.50 | 43.30 | | |
| | Difference | 1.18 | 3.19 | 0.45 | −1.10 | | |
| | 95% CI | −2.34, 4.70 | −3.91, 10.30 | −6.62, 7.51 | −8.64, 6.45 | | |
| 1 | rhBSSL | | | | 76.24 | | |
| | Placebo | | | | 73.88 | | |
| | Difference | | | | 2.37 | | |
| | 95% CI | | | | −4.22, 8.95 | | |
| 2 n-6 | rhBSSL | | | | 83.91 | | |
| | Placebo | | | | 78.93 | | |
| | Difference | | | | 4.99 | | |
| | 95% CI | | | | −0.98, 10.95 | | |
| 3 n-3 | rhBSSL | | | | 87.79 | | |
| | Placebo | | | | 83.37 | | |
| | Difference | | | | 4.42 | | |
| | 95% CI | | | | −1.09, 9.93 | | |
| 4 n-6 | rhBSSL | | | | | 82.96 | |
| | Placebo | | | | | 75.83 | |
| | Difference | | | | | 7.14 | |
| | 95% CI | | | | | −0.03, 14.30 | |
| 6 n-3 | rhBSSL | | | | | | 81.15 |
| | Placebo | | | | | | 74.31 |
| | Difference | | | | | | 6.85 |
| | 95% CI | | | | | | −0.84, 14.54 |

TABLE 2.14

CFA for individual fatty acids, study BVT.BSSL-021 (pasteurized breast milk) Per-protocol Analysis Set.

| No. double bonds | | No. of carbon atoms | | | | | | |
|---|---|---|---|---|---|---|---|---|
| | | 12 | 14 | 16 | 18 | 20 | 22 | 24 |
| 0 | rhBSSL | 87.94 | 75.49 | 63.88 | 46.11 | | | |
| | Placebo | 84.44 | 69.55 | 59.42 | 42.47 | | | |
| | Difference | 3.50 | 5.94* | 4.46 | 3.63 | | | |
| | 95% CI | −0.78, 7.78 | 0.31, 11.57 | −2.07, 11.00 | −4.39, 11.65 | | | |
| 1 | rhBSSL | | | 96.24 | 71.01 | 52.09 | | 36.85 |
| | Placebo | | | 95.80 | 66.24 | 43.57 | | 29.17 |
| | Difference | | | 0.45 | 4.77 | 8.53 | | 7.68 |
| | 95% CI | | | −0.06, 0.95 | −0.15, 9.68 | −2.73, 19.78 | | −4.95, 20.31 |
| 2 n-6 | rhBSSL | | | | 71.26 | 53.09 | | |
| | Placebo | | | | 64.28 | 44.72 | | |
| | Difference | | | | 6.98* | 8.37* | | |
| | 95% CI | | | | 1.21, 12.75 | 0.69, 16.06 | | |
| 3 n-3 | rhBSSL | | | | 64.39 | § | | |
| | Placebo | | | | 62.35 | | | |
| | Difference | | | | 2.04 | | | |
| | 95% CI | | | | −7.60, 11.67 | | | |
| 3 n-6 | rhBSSL | | | | 63.94 | 67.39§ | | |
| | Placebo | | | | 58.12 | 58.48 | | |
| | Difference | | | | 5.82 | 8.91* | | |
| | 95% CI | | | | −3.34, 14.99 | 1.40, 16.42 | | |
| 4 n-6 | rhBSSL | | | | | 72.10 | | |
| | Placebo | | | | | 61.28 | | |
| | Difference | | | | | 10.82* | | |
| | 95% CI | | | | | 2.85, 18.79 | | |
| 6 n-3 | rhBSSL | | | | | | 78.49 | |
| | Placebo | | | | | | 73.77 | |
| | Difference | | | | | | 4.72* | |
| | 95% CI | | | | | | 0.59, 8.85 | |

*P < 0.05

§The C20:3 species monitored during the study were C20:3 n-6 and C20:3 n-3, commonly named dihomo-gamma-linolenic acid (DGLA; C20:3 n-6) and eicosatrienoic acid (ETA; C20:3 n-3). As these two fatty acids could not be fully quantified separately these results in the cell "C20:3 n-6" are the sum of both species; between both of them, C20:3 n-6 (DGLA) is the most abundant.

Groups of FAs: An inspection of Tables 2.12 to 2.14 indicates that the effect of rhBSSL on fat absorption is especially low for the two saturated FAs, C16:0 and C18:0, and that the effect overall seems to increase with chain length and degree of unsaturation. Therefore, an analysis of the coefficient of fat absorption for the sum of all saturated and unsaturated FAs, respectively, was performed, and also analyses for the sum of all polyunsaturated FAs as well as the sum of all LCPUFAs (not only DHA and AA). The results for the combined analysis and by study, were collected and are summarized below in Tables 2.15 to 2.18.

TABLE 2.15

Coefficient of absorption of the sum of all saturated* fatty acids (%), per-protocol analysis set

| | BVT.BSSL-020 Formula N = 26 | | BVT.BSSL-021 Pasteurized milk N = 20 | | BVT.BSSL-020 and 021 Combined N = 46 | |
|---|---|---|---|---|---|---|
| | rhBSSL | Placebo | rhBSSL | Placebo | rhBSSL | Placebo |
| LS mean | 61.4 | 61.4 | 66.1 | 61.7 | 63.8 | 61.5 |
| 95% CI | 57.9, 65.0 | 57.8, 64.9 | 61.8, 70.4 | 57.4, 66.05 | 61.2, 66.5 | 58.8, 64.2 |
| LS mean difference (rhBSSL-Placebo) | 0.08 | | 4.36 | | 2.25 | |
| 95% CI of LS mean difference | −4.95, 5.10 | | −1.74, 10.46 | | −1.52, 6.02 | |
| p-value for LS mean difference | 0.975 | | 0.150 | | 0.236 | |

*FAs, independent of chain length, with no double bond.

TABLE 2.16

Coefficient of absorption of the sum of all unsaturated* fatty acids (%), per-protocol analysis set

|  | BVT.BSSL-020 Formula N = 26 | | BVT.BSSL-021 Pasteurized milk N = 20 | | BVT.BSSL-020 and 021 Combined N = 46 | |
| --- | --- | --- | --- | --- | --- | --- |
|  | rhBSSL | Placebo | rhBSSL | Placebo | rhBSSL | Placebo |
| LS mean | 78.8 | 75.5 | 70.6 | 65.5 | 74.7 | 70.5 |
| 95% CI | 74.4, 83.1 | 71.2, 79.9 | 67.08, 74.09 | 61.98, 68.99 | 71.9, 77.5 | 67.7, 73.3 |
| LS mean difference (rhBSSL-Placebo) | 3.25 | | 5.10 | | 4.22 | |
| 95% CI of LS mean difference | −2.90, 9.41 | | 0.14, 10.05 | | 0.32, 8.12 | |
| p-value for LS mean difference | 0.286 | | 0.044 | | 0.034 | |

*FAs, independent of chain length, with at least 1 double bond.

TABLE 2.17

Coefficient of absorption of the sum of all polyunsaturated* fatty acids (%), per-protocol analysis set

|  | BVT.BSSL-020 Formula N = 26 | | BVT.BSSL-021 Pasteurized milk N = 20 | | BVT.BSSL-020 and 021 Combined N = 46 | |
| --- | --- | --- | --- | --- | --- | --- |
|  | rhBSSL | Placebo | rhBSSL | Placebo | rhBSSL | Placebo |
| LS mean | 84.0 | 79.0 | 70.7 | 63.7 | 77.3 | 71.5 |
| 95% CI | 79.8, 88.3 | 74.8, 83.2 | 66.6, 74.7 | 59.7, 67.8 | 74.5, 80.1 | 68.6, 74.3 |
| LS mean difference (rhBSSL-Placebo) | 5.05 | | 6.92 | | 5.82 | |
| 95% CI of LS mean difference | −0.92, 11.02 | | 1.21, 12.62 | | 1.86, 9.77 | |
| p-value for LS mean difference | 0.093 | | 0.020 | | 0.005 | |

*FAs, independent of chain length, with at least 2 double bonds.

TABLE 2.18

Coefficient of absorption of the sum of all LCPUFAs* (%), per-protocol analysis set

|  | BVT.BSSL-020 Formula N = 26 | | BVT.BSSL-021 Pasteurized milk N = 20 | | BVT.BSSL-020 and 021 Combined N = 46 | |
| --- | --- | --- | --- | --- | --- | --- |
|  | rhBSSL | Placebo | rhBSSL | Placebo | rhBSSL | Placebo |
| LS mean | 82.2 | 75.2 | 70.2 | 62.2 | 76.1 | 68.8 |
| 95% CI | 77.1, 87.25 | 70.1, 80.2 | 65.9, 74.5 | 57.9, 66.4 | 72.8, 79.4 | 65.5, 72.0 |
| LS mean difference (rhBSSL-Placebo) | 7.01 | | 8.02 | | 7.33 | |
| 95% CI of LS mean difference | −0.15, 14.16 | | 2.00, 14.05 | | 2.77, 11.89 | |
| p-value for LS mean difference | 0.054 | | 0.012 | | 0.002 | |

*FAs with at least 20 carbon atoms and at least 2 double bonds.

The analyses presented in Tables 2.15 to 2.18 confirm these aspects of the invention, that the effect of rhBSSL on fat absorption increases with the degree of unsaturation, at the same time as the p-values decrease, from an LS mean for the difference in the combined analysis for the saturated FAs of 2.25% (p=0.236), to 4.22% (p=0.034) for the entire group of unsaturated FAs, and further to 5.82% (p=0.005) for the polyunsaturated FAs, and 7.33% (p=0.002) for the LCPUFAs.

8.5 Analysis of Safety: Adverse Events

8.5.1 Extent of Exposure

A summary of treatment exposure, as number of days on treatment, is provided in Table 2.19 below.

TABLE 2.19

Extent of Treatment Exposure-Safety Analysis Set

| | Variable Statistic | |
|---|---|---|
| Number of Days on Treatment [1] | rhBSSL (N = 61) | Placebo (N = 62) |
| 1 | 0 | 0 |
| 2 | 0 | 0 |
| 3 | 1 (1.6%) | 1 (1.6%) |
| 4 | 0 | 0 |
| 5 | 0 | 0 |
| 6 | 0 | 1 (1.6%) |
| 7 | 60 (98.4%) | 60 (96.8%) |
| n | 61 | 62 |

TABLE 2.19-continued

Extent of Treatment Exposure-Safety Analysis Set

| | Variable Statistic | |
|---|---|---|
| Number of Days on Treatment [1] | rhBSSL (N = 61) | Placebo (N = 62) |
| Mean | 6.9 | 6.9 |
| Std Dev | 0.51 | 0.52 |
| Median | 7.0 | 7.0 |
| Minimum | 3 | 3 |
| Maximum | 7 | 7 |

[1] Number of days on treatment = Last day of treatment period − First day of treatment period + 1.

The extent of treatment exposure was comparable between treatments. 98.4% of patients had 7 days of rhBSSL treatment and 96.8% of patients had 7 days of placebo treatment. One patient discontinued from BVT.BSSL-020 after 3 days of placebo treatment during the second period. Three (3) patients in BVT.BSSL-021 discontinued during the first treatment period: 2 patients discontinued after 6 and 7 days of placebo treatment, respectively, and one patient discontinued after 3 days of rhBSSL treatment.

A summary exposure to of rhBSSL is provided in Table 2.20 below.

TABLE 2.20

Extent of Exposure to rhBSSL -Safety Analysis Set

| | Variable Statistic |
|---|---|
| Total amount of rhB SSL (g) [1] | Total (N = 63) |
| n | 61 |
| Mean | 0.2717 |
| Std Dev | 0.05172 |
| Median | 0.2682 |
| Minimum | 0.063 |
| Maximum | 0.397 |

[1] Total amount of rhBSSL (g) = 0.15 g/L*(Total amount of food (L) ingested during rhBSSL treatment period − Total amount of vomit (L) during rhBSSL treatment period). Vomit was not collected on Days 1, 2, 3, 10, 11, and 12.
Note:
Concentration of rhBSSL in food is 0.15 g/L according to the protocols.

In the combined analysis results, the mean (SD) amount of rhBSSL consumed was 0.27 g (0.052 g).

8.5.2 Brief Summary of Adverse Events

The overall incidence rate of TEAEs is shown below in Table 2.21.

TABLE 2.21

Overall Summary of Treatment-emergent Adverse Events-Safety Analysis Set

| | rhBSSL (N = 61) | | Placebo (N = 62) | | Total (N = 63) | |
|---|---|---|---|---|---|---|
| | n (%) of Patients | Total AEs (n) | n (%) of Patients | Total AEs (n) | n (%) of Patients | Total AEs (n) |
| Patients with any TEAE | 29 (47.5%) | 56 | 32 (51.6%) | 78 | 45 (71.4%) | 134 |
| Patients with any serious TEAE | 0 | 0 | 2 (3.2%) | 2 | 2 (3.2%) | 2 |
| Patients with any TEAE leading to discontinuation from the study | 1 (1.6%) | 1 | 3 (4.8%) | 3 | 4 (6.3%) | 4 |
| Patients with any related TEAE | 5 (8.2%) | 6 | 4 (6.5%) | 6 | 8 (12.7%) | 12 |
| Patients with any severe TEAE | 1 (1.6%) | 1 | 6 (9.7%) | 16 | 6 (9.5%) | 17 |
| Patients who died | 0 | 0 | 1 (1.6%) | 1 | 1 (1.6%) | 1 |

Related includes definitely, probably, or possibly study medication related.

A total of 134 treatment-emergent adverse events (TEAEs) were experienced by 45 of 63 (71.4%) patients in these two studies. There was no noticeable difference observed in the proportion of patients with TEAEs between treatments. The proportions of patients with TEAEs were comparable between the studies: 23 (69.7%) patients experienced AEs in BVT.BSSL-020 and 22 (73.3%) in BVT.BSSL-021. However, the total number of TEAEs were higher in BVT.BSSL.021 (81 events) compared to BVT.BSSL.020 (53 events). (Tabulated data by study not shown in this report.)

Across the two studies, 2 (3.2%) patients reported one serious TEAE during placebo treatment, 4 (6.3%) patients reported one TEAE leading to discontinuation from the study (1 patient during rhBSSL treatment and 3 patients during placebo treatment), 8 (12.7%) patients reported at least one TEAE considered treatment related (5 patients had during rhBSSL treatment, 4 patients during placebo treatment, where one of these patients had a related TEAE during both periods), and one patient died during placebo treatment.

8.5.3 Display of Adverse Events

A summary of the most commonly reported TEAEs (reported in >=4% of the patients) is provided below in Table 2.22. A summary of all reported TEAEs was collected and summarized (not shown in this Report).

TABLE 2.22

Most Commonly Reported Treatment-Emergent Adverse Events-Safety Analysis Set

| Preferred Term | rhBSSL (N = 61) | | Placebo (N = 62) | | Total (N = 63) | |
|---|---|---|---|---|---|---|
| | n (%) of Patients | Total AEs (n) | n (%) of Patients | Total AEs (n) | n (%) of Patients | Total AEs (n) |
| Dermatitis diaper | 13 (21.3%) | 20 | 13 (21.0%) | 15 | 21 (33.3%) | 35 |
| Anemia | 3 (4.9%) | 3 | 6 (9.7%) | 6 | 8 (12.7%) | 9 |
| Cardiac murmur | 4 (6.6%) | 4 | 2 (3.2%) | 2 | 6 (9.5%) | 6 |
| Bradycardia | 1 (1.6%) | 2 | 5 (8.1%) | 15 | 5 (7.9%) | 17 |
| Hypokalemia | 3 (4.9%) | 3 | 2 (3.2%) | 2 | 5 (7.9%) | 5 |
| Anemia neonatal | 2 (3.3%) | 2 | 1 (1.6%) | 1 | 3 (4.8%) | 3 |
| Thrombocythemia | 0 | 0 | 3 (4.8%) | 3 | 3 (4.8%) | 3 |
| Urinary tract infection | 1 (1.6%) | 1 | 2 (3.2%) | 2 | 3 (4.8%) | 3 |

Note:
This table includes AEs reported in >=4% of patients. If a patient had more than one count for a particular preferred term, the patient was counted once for that preferred term.

The most common TEAE in the combined results for the two studies was dermatitis diaper reported by 21 (33.3%) patients. The incidence of this event was comparable between treatments. Other most commonly reported TEAEs were anemia in 8 (12.7%) patients, cardiac murmur in 6 (9.5%) patients, bradycardia and hypokalemia each reported by 5 (7.9%) patients, and anemia neonatal, thrombocythemia, and urinary tract infection each reported by 3 (4.8%) patients. All of the most common TEAEs were reported in both treatments, with the exception of thrombocythemia which was reported in placebo only. In addition, all of the most common TEAEs were reported in both studies, with the exception of urinary tract infection which was reported in BVT.BSSL-020 only and hypokalemia which was reported in BVS.BSSL-021 only.

9 CONCLUSIONS

The results of the combined analysis are consistent with the results of the individual studies supporting the following conclusions:
- rhBSSL significantly improves growth as compared to placebo in preterm infants receiving pasteurized breast milk or infant formula.
- There is a numerical but not significant improvement in fat absorption following rhBSSL treatment as compared to placebo.
- No difference with respect to the change in knee-to-heel length was observed after one week of rhBSSL treatment as compared to placebo.
- rhBSSL added to infant formula or pasteurized breast milk was well tolerated.
- No apparent difference in the safety profile during rhBSSL treatment as compared to placebo was observed.
- Patients on formula consumed more fat and gained more weight than patients on pasteurized breast milk.
- rhBSSL significantly improves the absorption of DHA and AA.
- rhBSSL significantly improves the absorption of unsaturated fatty acids, and especially the LCPUFAs.
- The effect of rhBSSL on fat absorption increases with chain length and with degree of unsaturation of the fatty acids.

Exhibit A

Proposed compositional requirements of infant formula—ESPGHAN recommended standards (adapted from Koletzko et al 2005):

| Component | Unit | Minimum | Maximum |
|---|---|---|---|
| Energy | kcal/100 ml | 60 | 70 |
| Proteins | | | |
| Cows' milk protein | g/100 kcal | 1.8* | 3 |
| Soy protein isolates | g/100 kcal | 2.25 | 3 |
| Hydrolyzed cows' milk protein | g/100 kcal | 1.8† | 3 |
| Lipids | g/100 kcal | | |
| Total fat | g/100 kcal | 4.4 | 6 |
| Linoleic acid | g/100 kcal | 0.3 | 1.2 |
| a-linolenic acid | mg/100 kcal | 50 | NS |
| Ratio linoleic/a-linolenic acids | | 5:1 | 15:1 |
| Lauric + myristic acids | % of fat | NS | 20 |
| Trans fatty acids | % of fat | NS | 3 |
| Erucic acid | % of fat | NS | 1 |
| Carbohydrates | | | |
| Total carbohydrates‡ | g/100 kcal | 9 | 14 |
| Vitamins | | | |
| Vitamin A | ug RE/100 kcal§ | 60 | 180 |
| Vitamin D3 | ug/100 kcal | 1 | 2.5 |
| Vitamin E | mg a-TE/100 kcal& | 0.5{ | 5 |
| Vitamin K | ug/100 kcal | 4 | 25 |
| Thiamin | ug/100 kcal | 60 | 300 |
| Riboflavin | ug/100 kcal | 80 | 400 |
| Niacin# | ug/100 kcal | 300 | 1500 |
| Vitamin B6 | ug/100 kcal | 35 | 175 |
| Vitamin B12 | ug/100 kcal | 0.1 | 0.5 |
| Pantothenic acid | ug/100 kcal | 400 | 2000 |
| Folic acid | ug/100 kcal | 10 | 50 |
| Vitamin C | mg/100 kcal | 8 | 30 |
| Biotin | ug/100 kcal | 1.5 | 7.5 |
| Minerals and trace elements | | | |
| Iron (formula based on cows' milk protein and protein hydrolysate) | mg/100 kcal | 0.3** | 1.3 |
| Iron (formula based on soy protein isolate) | mg/100 kcal | 0.45 | 2 |
| Calcium | mg/100 kcal | 50 | 140 |
| Phosphorus (formula based on cows' milk protein and protein hydrolysate) | mg/100 kcal | 25 | 90 |
| Phosphorus (formula based on soy protein isolate) | mg/100 kcal | 30 | 100 |
| Ratio calcium/phosphorus | mg/mg | 1:1 | 2:1 |
| Magnesium | mg/100 kcal | 5 | 15 |
| Sodium | mg/100 kcal | 20 | 60 |
| Chloride | mg/100 kcal | 50 | 160 |
| Potassium | mg/100 kcal | 60 | 160 |
| Manganese | ug/100 kcal | 1 | 50 |
| Fluoride | ug/100 kcal | NS | 60 |
| Iodine | ug/100 kcal | 10 | 50 |

| Component | Unit | Minimum | Maximum |
|---|---|---|---|
| Selenium | ug/100 kcal | 1 | 9 |
| Copper | ug/100 kcal | 35 | 80 |
| Zinc | mg/100 kcal | 0.5 | 1.5 |
| Other substances | | | |
| Choline | mg/100 kcal | 7 | 50 |
| Myo-inositol | mg/100 kcal | 4 | 40 |
| L-carnitine | mg/100 kcal | 1.2 | NS |

*The determination of the protein content of formulae based on non-hydrolyzed cows' milk protein with a protein should be based on measurement of true protein content between 1.8 and 2.0 g/100 kcal ([total N minus NPN] × 6.25)
†Formula based on hydrolyzed milk protein with a protein content less than 2.25 g/100 kcal should be clinically tested.
‡Sucrose (saccharose) and fructose should not be added to infant formula.
§1 mg RE (retinol equivalent) = 1 mg all-trans retinol = 3.33 IU vitamin A. Retinol contents shall be provided by preformed retinol, while any contents of carotenoids should not be included in the calculation and declaration of vitamin A activity.
&1 mg a-TE (a-tocopherol equivalent) = 1 mg d-a-tocopherol.
{Vitamin E content shall be at least 0.5 mg a-TE per g PUFA, using the following factors of equivalence to adapt the minimal vitamin E content to the number of fatty acid double bonds in the formula: 0.5 mg a-TE/g linoleic acid (18:2n − 6); 0.75 mg a-TE/g a-linolenic acid (18:3n − 3); 1.0 mg a-TE/g arachidonic acid (20:4n − 6); 1.25 mg a-TE/g eicosapentaenoic acid (20:5n − 3); 1.5 mg a-TE/g docosahexaenoic acid (22:6n − 3).
Niacin refers to preformed niacin.
**In populations where infants are at risk of iron deficiency, iron contents higher than the minimum level of 0.3 mg/100 kcal may be appropriate and recommended at a national level.
NS, not specified.

Exhibit B

Proposed levels of optional ingredients, if added—ESPGHAN recommended standards (adapted from Koletzko et al 2005):

| Optional ingredients | Unit | Minimum | Maximum |
|---|---|---|---|
| Taurine | mg/100 kcal | 0 | 12 |
| Total added nucleotides | mg/100 kcal | 0 | 5 |
| Cytidine 5#-monophosphate (CTP) | mg/100 kcal | 0 | 1.75 |
| Uridine 5#-monophosphate (UMO) | mg/100 kcal | 0 | 1.5 |
| Adenosine 5#-monophosphate (AMP) | mg/100 kcal | 0 | 1.5 |
| Guanosine 5#-monophosphate (GMP) | mg/100 kcal | 0 | 0.5 |
| Inosine 5#-monophosphate (IMP) | mg/100 kcal | 0 | 1 |
| Phospholipids | mg/100 kcal | 0 | 300 |
| Docosahexaenoic acid* | % of fat | 0 | 0.5 |

*If docosahexaenoic acid (22:6n − 3) is added to infant formula, arachidonic acid (20:4n − 6) contents should reach at least the same concentration as DHA. The content of eicosapentaenoic acid (20:5n − 3) should not exceed the content of docosahexaenoic acid.

TABLE 3

SEQUENCE LISTING

SEQ ID. NO. 1:

| | | | | | |
|---|---|---|---|---|---|
| AKLGAVYTEG | GFVEGVNKKL | GLLGDSVDIF | KGIPFAAPTK | ALENPQPHPG | 50 |
| WQGTLKAKNF | KKRCLQATIT | QDSTYGDEDC | LYLNIWVPQG | RKQVSRDLPV | 100 |
| MIWIYGGAFL | MGSGHGANFL | NNYLYDGEEI | ATRGNVIVVT | FNYRVGPLGF | 150 |
| LSTGDANLPG | NYGLRDQHMA | IAWVKRNIAA | FGGDPNNITL | FGESAGGASV | 200 |
| SLQTLSPYNK | GLIRRAISQS | GVALSPWVIQ | KNPLFWAKKV | AEKVGCPVGD | 250 |
| AARMAQCLKV | TDPRALTLAY | KVPLAGLEYP | MLHYVGFVPV | IDGDFIPADP | 300 |
| INLYANAADI | DYIAGTNNMD | GHIFASIDMP | AINKGNKKVT | EEDFYKLVSE | 350 |
| FTITKGLRGA | KTTFDVYTES | WAQDPSQENK | KKTVVDFETD | VLFLVPTEIA | 400 |
| LAQHRANAKS | AKTYAYLFSH | PSRMPVYPKW | VGADHADDIQ | YVFGKPFATP | 450 |
| TGYRPQDRTV | SKAMIAYWTN | FAKTGDPNMG | DSAVPTHWEP | YTTENSGYLE | 500 |
| ITKKMGSSSM | KRSLRTNFLR | YWTLTYLALP | TVTDQEATPV | PPTGDSEATP | 550 |
| VPPTGDSETA | PVPPTGDSGA | PPVPPTGDSG | APPVPPTGDS | GAPPVPPTGD | 600 |
| SGAPPVPPTG | DSGAPPVPPT | GDSGAPPVPP | TGDSGAPPVP | PTGDAGPPPV | 650 |
| PPTGDSGAPP | VPPTGDSGAP | PVTPTGDSET | APVPPTGDSG | APPVPPTGDS | 700 |
| EAAPVPPTDD | SKEAQMPAVI | RF | | | 722 |

TABLE 4

SEQUENCE LISTING

SEQ ID. NO. 2:

```
  1 accttctgta tcagttaagt gtcaagatgg aaggaacagc agtctcaaga taatgcaaag 61 agtttattca tccagaggct gatgctcacc atgggcgcc tgcaactggt tgtgttgggc
                         ***
121 ctcacctgct gctgggcagt ggcgagtgcc gcgaagctgg gcgccgtgta cacagaaggt
```

TABLE 4-continued

SEQUENCE LISTING

SEQ ID. NO. 2:

```
 181 gggttcgtgg aaggcgtcaa taagaagctc ggcctcctgg gtgactctgt ggacatcttc
 241 aagggcatcc ccttcgcagc tcccaccaag gccctggaaa atcctcagcc acatcctggc
 301 tggcaaggga ccctgaaggc caagaacttc aagaagagat gcctgcaggc caccatcacc
 361 caggacagca cctacgggga tgaagactgc ctgtacctca acatttgggt gccccagggc
 421 aggaagcaag tctcccggga cctgcccgtt atgatctgga tctatggagg cgccttcctc
 481 atggggtccg gccatgggc caacttcctc aacaactacc tgtatgacgg cgaggagatc
 541 gccacacgcg gaaacgtcat cgtggtcacc ttcaactacc gtgtcggccc ccttgggttc
 601 ctcagcactg gggacgccaa tctgccaggt aactatggcc ttcgggatca gcacatggcc
 661 attgcttggg tgaagaggaa tatcgcggcc ttcgggggg accccaacaa catcacgctc
 721 ttcggggagt ctgctggagg tgccagcgtc tctctgcaga ccctctcccc ctacaacaag
 781 ggcctcatcc ggcgagccat cagccagagc ggcgtggccc tgagtccctg ggtcatccag
 841 aaaaacccac tcttctgggc caaaaaggtg gctgagaagg tgggttgccc tgtgggtgat
 901 gccgccagga tggcccagtg tctgaaggtt actgatcccc gagccctgac gctggcctat
 961 aaggtgccgc tggcaggcct ggagtacccc atgctgcact atgtgggctt cgtccctgtc
1021 attgatggag acttcatccc cgctgacccg atcaacctgt acgccaacgc cgccgacatc
1081 gactatatag caggcaccaa caacatggac ggccacatct cgccagcat cgacatgcct
1141 gccatcaaca agggcaacaa gaaagtcacg gaggaggact tctacaagct ggtcagtgag
1201 ttcacaatca ccaaggggct cagaggcgcc aagacgacct ttgatgtcta caccgagtcc
1261 tgggcccagg acccatccca ggagaataag aagaagactg tggtggactt tgagaccgat
1321 gtcctcttcc tggtgcccac cgagattgcc ctagcccagc acagagccaa tgccaagagt
1381 gccaagacct acgcctacct gttttcccat ccctctcgga tgcccgtcta ccccaaatgg
1441 gtggggccg accatgcaga tgacattcag tacgttttcg ggaagccctt cgccacccc
1501 acgggctacc ggcccaaga caggacagtc tctaaggcca tgatcgccta ctggaccaac
1561 tttgccaaaa caggggaccc caacatgggc gactcggctg tgcccacaca ctgggaaccc
1621 tacactacgg aaaacagcgg ctacctggag atcaccaaga agatgggcag cagctccatg
1681 aagcggagcc tgagaaccaa cttcctgcgc tactggaccc tcacctatct ggcgctgccc
1741 acagtgaccg accaggaggc cacccctgtg ccccccacag gggactccga ggccactccc
1801 gtgcccccca cggtgactc cgagaccgcc ccgtgccgc cacgggtga ctccggggcc
1861 cccccgtgc cgcccacggg tgactccggg gccccccg tgccgccac gggtgactcc
1921 ggggcccccc ccgtgccgcc cacgggtgac tccggggccc ccccgtgcc gcccacgggt
1981 gactccgggg cccccccgt gccgcccacg ggtgactccg ggcccccc cgtgccgccc
2041 acgggtgact ccggcgcccc cccgtgccg cccacgggtg acgccgggcc ccccccgtg
2101 ccgcccacgg gtgactccgg cgcccccccc gtgccgccca cggtgactc cggggccccc
2161 cccgtgaccc cacgggtga ctccgagacc gccccgtgc cgcccacggg tgactccggg
2221 gcccccctg tgccccccac gggtgactct gaggctgccc ctgtgcccc cacagatgac
2281 tccaaggaag ctcagatgcc tgcagtcatt aggttttagc gtcccatgag ccttggtatc
```
§§§

TABLE 4-continued

SEQUENCE LISTING

SEQ ID. NO. 2:

2341 aagaggccac aagagtggga ccccaggggc tccctccca tcttgagctc ttcctgaata 2401 aagcctcata ccctaaaaa aaaaaaaa The start and stop codons are marked (underneath) with "***" and "§§§" respectively. The leader sequence is underlined.

The invention claimed is:

1. A method to increase the absorption by a preterm human infant of at least one unsaturated fatty acid from infant formula or pasteurized human milk, said method comprising:
enteral administration of 1 to 100 mg per kg of infant of a recombinant human bile-salt-stimulated lipase to said preterm infant, wherein said infant is from about 21 to 37 weeks of gestation.

2. The method of claim 1, wherein said at least one unsaturated fatty acid is selected from the group consisting of:
a. an essential fatty acid;
b. a polyunsaturated fatty acid;
c. an unsaturated fatty acid that has an aliphatic chain of 20 or more carbon atoms; and
d. a polyunsaturated fatty acid that has an aliphatic chain of 20 or more carbon atoms (long chain polyunsaturated fatty acid—LCPUFA).

3. The method of claim 1, wherein said at least one unsaturated fatty acid is one selected from the group consisting of: eicosadienoic acid (C20:2 n-6), dihomo-gamma-linolenic acid (C20:3 n-6), eicosatrienoic acid (C20:3 n-3), arachidonic acid (C20:4 n-6) and docosahexaenoic acid (C22:6 n-3), linoleic acid (C18:2 n-6) and alpha-linolenic acid (C18:3 n-3).

4. The method of claim 1, wherein the visual and/or cognitive development of said infant is improved following administration of said lipase.

5. The method of claim 1, wherein said infant is not fed fresh mother's milk.

6. The method of claim 1, wherein said lipase is first added to infant formula or pasteurized breast milk which is then fed to said infant, thereby enterally administering said lipase.

7. The method of claim 1, wherein said human infant is a preterm human infant, one born between week 32 and week 37 of gestation, between week 25 and week 37 of gestation, or between week 22 and week 25 of gestation.

8. The method of claim 1, wherein said lipase is administered with at least one feed per day over at least 5 days, or with at least one feed per day over at least 7 days, preferably wherein said lipase is administered with most or for all feeds per day.

9. The method of claim 1, wherein said increase in the absorption of at least one unsaturated fatty acid is concomitant with an increase in the growth velocity of said infant, preferably wherein said increase in growth velocity is an increase in the rate of weight gain of said infant, and most preferably wherein the rate of weight gain of the human infant is between 10 and 30 g increase in weight per Kg body weight of said infant per day (g/Kg/day), between 15 and 25 g/Kg/day, or 20 g/Kg/day or 18 g/Kg/day.

10. The method of claim 1, wherein said lipase is further defined by one or more features selected from:
a. said lipase is free of other milk proteins or milk components, such as milk casin and whey proteins, such as lactoferrin, or free of other contaminates native to milk, in particular where such milk-derived proteins or other contaminates are derived from the milk of humans, sheep or mice;
b. said lipase has a purity of greater than about 70%;
c. said lipase has a level of glycosylation that is less than that of BSSL-MAM and/or
greater than that of rhBSSL-OVI;
d. said lipase has a glycosylation pattern that is different to that of BSSL-MAM and/or different to that of rhBSSL-OVI;
e. said lipase has a molecular mass of between 90 KDa and 75 KDa, between about 84 and 86 KDa, or about 85 KDa; and/or
f. the amount of lipase molecules that are present in a form that is shorter at the C-terminal end by 1 or 2 amino acids compared to the full-length form represented by the sequence shown in SEQ ID. NO. 1 is greater than 50% of the amount of lipase molecules present in the full-length form represented by the sequence shown in SEQ ID. NO. 1.

\* \* \* \* \*

SEQUENCE LISTING

<160> NUMBER OF SEQ ID NOS: 2

<210> SEQ ID NO 1
<211> LENGTH: 722
<212> TYPE: PRT
<213> ORGANISM: Homo sapiens

<400> SEQUENCE: 1

```
Ala Lys Leu Gly Ala Val Tyr Thr Glu Gly Gly Phe Val Glu Gly Val
1               5                   10                  15

Asn Lys Lys Leu Gly Leu Leu Gly Asp Ser Val Asp Ile Phe Lys Gly
            20                  25                  30

Ile Pro Phe Ala Ala Pro Thr Lys Ala Leu Glu Asn Pro Gln Pro His
        35                  40                  45

Pro Gly Trp Gln Gly Thr Leu Lys Ala Lys Asn Phe Lys Lys Arg Cys
    50                  55                  60

Leu Gln Ala Thr Ile Thr Gln Asp Ser Thr Tyr Gly Asp Glu Asp Cys
65                  70                  75                  80

Leu Tyr Leu Asn Ile Trp Val Pro Gln Gly Arg Lys Gln Val Ser Arg
                85                  90                  95

Asp Leu Pro Val Met Ile Trp Ile Tyr Gly Gly Ala Phe Leu Met Gly
            100                 105                 110

Ser Gly His Gly Ala Asn Phe Leu Asn Asn Tyr Leu Tyr Asp Gly Glu
        115                 120                 125

Glu Ile Ala Thr Arg Gly Asn Val Ile Val Val Thr Phe Asn Tyr Arg
    130                 135                 140

Val Gly Pro Leu Gly Phe Leu Ser Thr Gly Asp Ala Asn Leu Pro Gly
145                 150                 155                 160

Asn Tyr Gly Leu Arg Asp Gln His Met Ala Ile Ala Trp Val Lys Arg
                165                 170                 175

Asn Ile Ala Ala Phe Gly Gly Asp Pro Asn Asn Ile Thr Leu Phe Gly
            180                 185                 190

Glu Ser Ala Gly Gly Ala Ser Val Ser Leu Gln Thr Leu Ser Pro Tyr
        195                 200                 205

Asn Lys Gly Leu Ile Arg Arg Ala Ile Ser Gln Ser Gly Val Ala Leu
    210                 215                 220

Ser Pro Trp Val Ile Gln Lys Asn Pro Leu Phe Trp Ala Lys Lys Val
225                 230                 235                 240

Ala Glu Lys Val Gly Cys Pro Val Gly Asp Ala Ala Arg Met Ala Gln
                245                 250                 255

Cys Leu Lys Val Thr Asp Pro Arg Ala Leu Thr Leu Ala Tyr Lys Val
            260                 265                 270

Pro Leu Ala Gly Leu Glu Tyr Pro Met Leu His Tyr Val Gly Phe Val
        275                 280                 285
```

-continued

Pro Val Ile Asp Gly Asp Phe Ile Pro Ala Asp Pro Ile Asn Leu Tyr
290                 295                 300

Ala Asn Ala Ala Asp Ile Asp Tyr Ile Ala Gly Thr Asn Asn Met Asp
305                 310                 315                 320

Gly His Ile Phe Ala Ser Ile Asp Met Pro Ala Ile Asn Lys Gly Asn
                325                 330                 335

Lys Lys Val Thr Glu Glu Asp Phe Tyr Lys Leu Val Ser Glu Phe Thr
            340                 345                 350

Ile Thr Lys Gly Leu Arg Gly Ala Lys Thr Thr Phe Asp Val Tyr Thr
        355                 360                 365

Glu Ser Trp Ala Gln Asp Pro Ser Gln Glu Asn Lys Lys Thr Val
    370                 375                 380

Val Asp Phe Glu Thr Asp Val Leu Phe Leu Val Pro Thr Glu Ile Ala
385                 390                 395                 400

Leu Ala Gln His Arg Ala Asn Ala Lys Ser Ala Lys Thr Tyr Ala Tyr
                405                 410                 415

Leu Phe Ser His Pro Ser Arg Met Pro Val Tyr Pro Lys Trp Val Gly
                420                 425                 430

Ala Asp His Ala Asp Asp Ile Gln Tyr Val Phe Gly Lys Pro Phe Ala
                435                 440                 445

Thr Pro Thr Gly Tyr Arg Pro Gln Asp Arg Thr Val Ser Lys Ala Met
    450                 455                 460

Ile Ala Tyr Trp Thr Asn Phe Ala Lys Thr Gly Asp Pro Asn Met Gly
465                 470                 475                 480

Asp Ser Ala Val Pro Thr His Trp Glu Pro Tyr Thr Thr Glu Asn Ser
                485                 490                 495

Gly Tyr Leu Glu Ile Thr Lys Lys Met Gly Ser Ser Met Lys Arg
            500                 505                 510

Ser Leu Arg Thr Asn Phe Leu Arg Tyr Trp Thr Leu Thr Tyr Leu Ala
        515                 520                 525

Leu Pro Thr Val Thr Asp Gln Glu Ala Thr Pro Val Pro Pro Thr Gly
    530                 535                 540

Asp Ser Glu Ala Thr Pro Val Pro Pro Thr Gly Asp Ser Glu Thr Ala
545                 550                 555                 560

Pro Val Pro Pro Thr Gly Asp Ser Gly Ala Pro Pro Val Pro Pro Thr
                565                 570                 575

Gly Asp Ser Gly Ala Pro Pro Val Pro Pro Thr Gly Asp Ser Gly Ala
            580                 585                 590

Pro Pro Val Pro Pro Thr Gly Asp Ser Gly Ala Pro Pro Val Pro Pro
        595                 600                 605

Thr Gly Asp Ser Gly Ala Pro Pro Val Pro Pro Thr Gly Asp Ser Gly
    610                 615                 620

Ala Pro Pro Val Pro Pro Thr Gly Asp Ser Gly Ala Pro Pro Val Pro
625                 630                 635                 640

Pro Thr Gly Asp Ala Gly Pro Pro Val Pro Pro Thr Gly Asp Ser
                645                 650                 655

Gly Ala Pro Pro Val Pro Pro Thr Gly Asp Ser Gly Ala Pro Pro Val
            660                 665                 670

Thr Pro Thr Gly Asp Ser Glu Thr Ala Pro Val Pro Pro Thr Gly Asp
        675                 680                 685

Ser Gly Ala Pro Pro Val Pro Pro Thr Gly Asp Ser Glu Ala Ala Pro
    690                 695                 700

Val Pro Pro Thr Asp Asp Ser Lys Glu Ala Gln Met Pro Ala Val Ile
705                 710                 715                 720

Arg Phe

<210> SEQ ID NO 2
<211> LENGTH: 2428
<212> TYPE: DNA
<213> ORGANISM: Homo sapiens

<400> SEQUENCE: 2

| | | | | | |
|---|---|---|---|---|---|
| accttctgta | tcagttaagt | gtcaagatgg | aaggaacagc | agtctcaaga | taatgcaaag | 60 |
| agtttattca | tccagaggct | gatgctcacc | atggggcgcc | tgcaactggt | tgtgttgggc | 120 |
| ctcacctgct | gctgggcagt | ggcgagtgcc | gcgaagctgg | gcgccgtgta | cacagaaggt | 180 |
| gggttcgtgg | aaggcgtcaa | taagaagctc | ggcctcctgg | gtgactctgt | ggacatcttc | 240 |
| aagggcatcc | ccttcgcagc | tcccaccaag | gccctggaaa | tcctcagcc | acatcctggc | 300 |
| tggcaaggga | ccctgaaggc | caagaacttc | aagaagagat | gcctgcaggc | caccatcacc | 360 |
| caggacagca | cctacgggga | tgaagactgc | ctgtacctca | catttgggt | gccccagggc | 420 |
| aggaagcaag | tctcccggga | cctgcccgtt | atgatctgga | tctatggagg | cgccttcctc | 480 |
| atggggtccg | gccatggggc | caacttcctc | aacaactacc | tgtatgacgg | cgaggagatc | 540 |
| gccacacgcg | gaaacgtcat | cgtggtcacc | ttcaactacc | gtgtcggccc | ccttgggttc | 600 |
| ctcagcactg | gggacgccaa | tctgccaggt | aactatggcc | ttcgggatca | gcacatggcc | 660 |
| attgcttggg | tgaagaggaa | tatcgcggcc | ttcggggggg | accccaacaa | catcacgctc | 720 |
| ttcgggagt | ctgctggagg | tgccagcgtc | tctctgcaga | ccctctcccc | ctacaacaag | 780 |
| ggcctcatcc | ggcgagccat | cagccagagc | ggcgtggccc | tgagtccctg | ggtcatccag | 840 |
| aaaaacccac | tcttctgggc | caaaaaggtg | gctgagaagg | tgggttgccc | tgtgggtgat | 900 |
| gccgccagga | tggcccagtg | tctgaaggtt | actgatcccc | gagccctgac | gctggcctat | 960 |
| aaggtgccgc | tggcaggcct | ggagtacccc | atgctgcact | atgtgggctt | cgtccctgtc | 1020 |
| attgatggag | acttcatccc | cgctgacccg | atcaacctgt | acgccaacgc | cgccgacatc | 1080 |
| gactatatag | caggcaccaa | caacatggac | ggccacatct | tcgccagcat | cgacatgcct | 1140 |
| gccatcaaca | agggcaacaa | gaaagtcacg | gaggaggact | tctacaagct | ggtcagtgag | 1200 |
| ttcacaatca | ccaagggggct | cagaggcgcc | aagacgacct | tgatgtcta | caccgagtcc | 1260 |
| tgggcccagg | acccatccca | ggagaataag | aagaagactg | tggtggactt | tgagaccgat | 1320 |
| gtcctcttcc | tggtgcccac | cgagattgcc | ctagcccagc | acagagccaa | tgccaagagt | 1380 |
| gccaagacct | acgcctacct | gtttttcccat | ccctctcgga | tgcccgtcta | ccccaaatgg | 1440 |
| gtgggggccg | accatgcaga | tgacattcag | tacgttttcg | ggaagccctt | cgccacccc | 1500 |
| acgggctacc | ggccccaaga | caggacagtc | tctaaggcca | tgatcgccta | ctggaccaac | 1560 |
| tttgccaaaa | caggggaccc | caacatgggc | gactcggctg | tgcccacaca | ctgggaaccc | 1620 |
| tacactacgg | aaaacagcgg | ctacctggag | atcaccaaga | agatgggcag | cagctccatg | 1680 |
| aagcggagcc | tgagaaccaa | cttcctgcgc | tactggacccc | tcacctatct | ggcgctgccc | 1740 |
| acagtgaccg | accaggaggc | cacccctgtg | cccccacag | gggactccga | ggccactccc | 1800 |
| gtgcccccca | cggtgactc | cgagaccgcc | cccgtgccgc | ccacgggtga | ctccggggcc | 1860 |
| cccccgtgc | cgcccacggg | tgactccggg | gccccccccg | tgccgcccac | gggtgactcc | 1920 |
| ggggcccccc | ccgtgccgcc | cacgggtgac | tccggggccc | ccccgtgcc | gcccacgggt | 1980 |

```
gactccgggg cccccccgt gccgcccacg ggtgactccg gggcccccc cgtgccgccc    2040 acgggtgact ccggcgcccc ccccgtgccg cccacgggtg acgccgggcc cccccccgtg    2100
ccgcccacgg gtgactccgg cgcccccccc gtgccgccca cgggtgactc cggggccccc    2160
cccgtgaccc ccacgggtga ctccgagacc gccccgtgc cgcccacggg tgactccggg    2220
gccccccctg tgcccccac gggtgactct gaggctgccc ctgtgccccc cacagatgac    2280
tccaaggaag ctcagatgcc tgcagtcatt aggttttagc gtcccatgag ccttggtatc    2340
aagaggccac aagagtggga ccccaggggc tcccctccca tcttgagctc ttcctgaata    2400
aagcctcata cccctaaaaa aaaaaaaa                                      2428
```